US012268690B2

(12) United States Patent
Tyner et al.

(10) Patent No.: US 12,268,690 B2
(45) Date of Patent: Apr. 8, 2025

(54) TREATMENTS FOR MUTATIONS IN ACUTE MYELOID LEUKEMIA

(71) Applicant: OREGON HEALTH & SCIENCE UNIVERSITY, Portland, OR (US)

(72) Inventors: Jeffrey W Tyner, Portland, OR (US); Cristina Tognon, Portland, OR (US); Brian J Druker, Portland, OR (US); Daniel Bottomly, Beaverton, OR (US); Beth Wilmot, Portland, OR (US); Stephen Kurtz, Portland, OR (US); Samantha Savage Stevens, Portland, OR (US); Nicola Long, Portland, OR (US); Anna Reister Schultz, Beaverton, OR (US); Elie Traer, Portland, OR (US); Shannon K McWeeney, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 1048 days.

(21) Appl. No.: 17/263,531

(22) PCT Filed: Jul. 26, 2019

(86) PCT No.: PCT/US2019/043759
§ 371 (c)(1),
(2) Date: Jan. 26, 2021

(87) PCT Pub. No.: WO2020/023921
PCT Pub. Date: Jan. 30, 2020

(65) Prior Publication Data
US 2021/0235374 A1 Jul. 29, 2021
US 2024/0033265 A2 Feb. 1, 2024

Related U.S. Application Data

(60) Provisional application No. 62/711,452, filed on Jul. 27, 2018.

(51) Int. Cl.
*A61K 31/519* (2006.01)
*C12Q 1/6886* (2018.01)

(52) U.S. Cl.
CPC .......... *A61K 31/519* (2013.01); *C12Q 1/6886* (2013.01); *C12Q 2600/106* (2013.01); *C12Q 2600/156* (2013.01); *C12Q 2600/158* (2013.01)

(58) Field of Classification Search
CPC ............... A61K 31/519; C12Q 1/6886; C12Q 2600/106; C12Q 2600/156; C12Q 2600/158
USPC .................................................... 514/262.1
See application file for complete search history.

(56) References Cited

U.S. PATENT DOCUMENTS

| 10,111,882 B2 | 10/2018 | Abella |
| 2016/0166579 A1 | 6/2016 | Di Paolo |
| 2017/0157132 A1 | 6/2017 | Wu |
| 2017/0232030 A1 | 8/2017 | Klaus |
| 2018/0117031 A1 | 5/2018 | Jain |
| 2018/0153975 A1 | 6/2018 | Fritsch |
| 2020/0054639 A1 | 2/2020 | Tyner |
| 2020/0338088 A1 | 10/2020 | Nesterovitch |

FOREIGN PATENT DOCUMENTS

| WO | WO-2016065674 A1 * | 5/2016 | ........... A61K 31/519 |
| WO | WO-2018081830 A9 * | 6/2018 | ............ A61K 31/44 |

OTHER PUBLICATIONS

English translation of WO 2016/065674 A1 (Year: 2016).*
The PCT Search Report and Written Opinion mailed Oct. 11, 2019 for PCT application No. PCT/US2019/043759, 20 pages.
Kottaridis, P. D. et al. The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials. Blood 98, 1752-1759 (2001).
Dohner, K. et al. Mutant nucleophosmin (NPM1) predicts favorable prognosis in younger adults with acute myeloid leukemia and normal cytogenetics: interaction with other gene mutations. Blood 106, 3740-3746, doi:10.1182/blood-2005-05-2164 (2005).
Falini, B. et al. Acute myeloid leukemia carrying cytoplasmic/mutated nucleophosmin (NPMc+ AML): biologic and clinical features. Blood 109, 874-885, doi:10.1182/blood-2006-07-012252 (2007).
Huang, Q. et al. A rapid, one step assay for simultaneous detection of FLT3/ITD and NPM1 mutations in AML with normal cytogenetics. Br J Haematol 142, 489-492, doi:10.1111/j.1365-2141.2008.07205.x (2008).
Wouters, B. J. et al. Double CEBPA mutations, but not single CEBPA mutations, define a subgroup of acute myeloid leukemia with a distinctive gene expression profile that is uniquely associated with a favorable outcome. Blood 113, 3088-3091, doi:10.1182/blood-2008-09-179895 (2009).
Kurtz, S. E. et al. Molecularly targeted drug combinations demonstrate selective effectiveness for myeloid- and lymphoid-derived hematologic malignancies. Proc Natl Acad Sci U S A 114, E7554-E7563, doi:10.1073/pnas.1703094114 (2017).
Papaemmanuil, E. et al. Genomic Classification and Prognosis in Acute Myeloid Leukemia. N Engl J Med 374, 2209-2221, doi:10.1056/NEJMoa1516192 (2016).
Arber, D. A. et al. The 2016 revision to the World Health Organization classification of myeloid neoplasms and acute leukemia. Blood 127, 2391-2405, doi:10.1182/blood-2016-03-643544 (2016).
Dohner, H. et al. Diagnosis and management of AML in adults: 2017 ELN recommendations from an international expert panel. Blood 129, 424-447, doi:10.1182/blood-2016-08-733196 (2017).
TCGA. Genomic and epigenomic landscapes of adult de novo acute myeloid leukemia. N Engl J Med 368, 2059-2074, doi:10.1056/NEJMoa1301689 (2013).

(Continued)

*Primary Examiner* — Kristin A Vajda

(57) ABSTRACT

The present invention relates to useful methods of treating Acute Myeloid Leukemia (AML) in a human. in the presence of gene mutations.

5 Claims, 8 Drawing Sheets

(56) References Cited

OTHER PUBLICATIONS

Patel, J. P. et al. Prognostic relevance of integrated genetic profiling in acute myeloid leukemia. N Engl J Med 366, 1079-1089, doi:10.1056/NEJMoa1112304 (2012).

Lundberg, P. et al. Clonal evolution and clinical correlates of somatic mutations in myeloproliferative neoplasms. Blood 123, 2220-2228, doi:10.1182/blood-2013-11-537167 (2014).

Genovese, G. et al. Clonal hematopoiesis and blood-cancer risk inferred from blood DNA sequence. N Engl J Med 371, 2477-2487, doi:10.1056/NEJMoa1409405 (2014).

Tse, K. F. et al. Constitutive activation of FLT3 stimulates multiple intracellular signal transducers and results in transformation. Leukemia 14, 1766-1776 (2000).

Yamamoto, Y. et al. Activating mutation of D835 within the activation loop of FLT3 in human hematologic malignancies. Blood 97, 2434-2439 (2001).

Yokota, S. et al. Internal tandem duplication of the FLT3 gene is preferentially seen in acute myeloid leukemia and myelodysplastic syndrome among various hematological malignancies. A study on a large series of patients and cell lines. Leukemia 11, 1605-1609 (1997).

Knapper, S. et al. A phase 2 trial of the FLT3 inhibitor lestaurtinib (CEP701) as first-line treatment for older patients with acute myeloid leukemia not considered fit for intensive chemotherapy. Blood 108, 3262-3270, doi:blood-2006-04-015560 [pii]10.1182/blood-2006-04-015560 (2006).

Ofarrell, A. M. et al. An innovative phase I clinical study demonstrates inhibition of FLT3 phosphorylation by SU11248 in acute myeloid leukemia patients. Clin Cancer Res 9, 5465-5476 (2003).

Smith, B. D. et al. Single-agent CEP-701, a novel FLT3 inhibitor, shows biologic and clinical activity in patients with relapsed or refractory acute myeloid leukemia. Blood 103, 3669-3676, doi:10.1182/blood-2003-11-37752003-11-3775 [pii] (2004).

Deangelo, D. J. et al. Phase 1 clinical results with tandutinib (MLN518), a novel FLT3 antagonist, in patients with acute myelogenous leukemia or high-risk myelodysplastic syndrome: safety, pharmacokinetics, and pharmacodynamics. Blood 108, 3674-3681, doi:10.1182/blood-2006-02-005702 (2006).

Stone, R. M. et al. Midostaurin plus Chemotherapy for Acute Myeloid Leukemia with a FLT3 Mutation. N Engl J Med 377, 454-464, doi:10.1056/NEJMoa1614359 (2017).

Smith, C. C. et al. Validation of ITD mutations in FLT3 as a therapeutic target in human acute myeloid leukaemia. Nature 485, 260-263, doi:nature11016 [pii]10.1038/nature11016 (2012).

Shih, A. H. et al. Mutational cooperativity linked to combinatorial epigenetic gain of function in acute myeloid leukemia. Cancer Cell 27, 502-515, doi:10.1016/j.ccell.2015.03.009 (2015).

Sato, T. et al. FLT3 ligand impedes the efficacy of FLT3 inhibitors in vitro and in vivo. Blood 117, 3286-3293, doi:10.1182/blood-2010-01-266742 (2011).

Traer, E. et al. FGF2 from Marrow Microenvironment Promotes Resistance to FLT3 Inhibitors in Acute Myeloid Leukemia. Cancer Res, doi:10.1158/0008-5472.can-15-3569 (2016).

Welch, J. S. et al. TP53 and Decitabine in Acute Myeloid Leukemia and Myelodysplastic Syndromes. N Engl J Med 375, 2023-2036, doi:10.1056/NEJMoa1605949 (2016).

Konopleva, M. et al. Efficacy and Biological Correlates of Response in a Phase II Study of Venetoclax Monotherapy in Patients with Acute Myelogenous Leukemia. Cancer Discov 6, 1106-1117, doi:10.1158/2159-8290.cd-16-0313 (2016).

Dinardo, C. D. et al. Safety and preliminary efficacy of venetoclax with decitabine or azacitidine in elderly patients with previously untreated acute myeloid leukaemia: a non-randomised, open-label, phase 1b study. Lancet Oncol, doi:10.1016/S1470-2045(18)30010-X (2018).

Tyner, J. W. et al. Kinase Pathway Dependence in Primary Human Leukemias Determined by Rapid Inhibitor Screening. Cancer Res 73, 285-296, doi:0008-5472.CAN-12-1906 [pii]10.1158/0008-5472.CAN-12-1906 (2013).

Puissant, A. et al. SYK is a critical regulator of FLT3 in acute myeloid leukemia. Cancer Cell 25, 226-242, doi:10.1016/j.ccr.2014.01.022 (2014).

Brinda, B. et al. The rocky road to personalized medicine in acute myeloid leukaemia. J Cell Mol Med. Mar. 2018;22(3):1411-1427. doi: 10.1111/jcmm.13478.

Choschzick, M. et al. Immunohistochemistry and molecular analyses in myeloid sarcoma of the breast in a patient with relapse of NPM1-mutated and FLT3-mutated AML after allogeneic stem cell transplantation. J Clin Pathol. Jun. 2010;63(6):558-61. doi: 10.1136/jcp.2009.071357.

Guenounou, S. et al. Sorafenib plus all-trans retinoic acid for AML patients with FLT3-ITD and NPM1 mutations. Eur J Haematol. Dec. 2014;93(6):533-6. doi: 10.1111/ejh.12334.

Heath, E. M. et al. Biological and clinical consequences of NPM1 mutations in AML. Leukemia. Apr. 2017;3(4):798-807. doi: 10.1038/leu.2017.30.

Hou, H. A. et al. DNMT3A mutations in acute myeloid leukemia: stability during disease evolution and clinical implications. Blood. Jan. 12, 2012;119(2):559-68. doi: 10.1182/blood-2011-07-369934.

Kurtz, et al. Identification of effective combinations of targeted drugs for DNMT3A and NPM1 mutated acute myeloid leukemia. Blood 2017; 130(1): 2068.

Nybakken, G. E. et al. Quizartinib elicits differential responses that correlate with karyotype and genotype of the leukemic clone. Leukemia. Jun. 2016;30(6):1422-5. doi: 10.1038/leu.2015.320.

Ley, T. J. et al. DNMT3A mutations in acute myeloid leukemia. N Engl J Med. Dec. 16, 2010;363(25):2424-33. doi: 10.1056/NEJMoa1005143.

Nonami, A. et al. Identification of novel therapeutic targets in acute leukemias with NRAS mutations using a pharmacologic approach. Blood. May 14, 2015;125(20):3133-43. doi: 10.1182/blood-2014-12-615906.

Hing, Z. A. et al. Next-generation XPO1 inhibitor shows improved efficacy and in vivo tolerability in hematological malignancies. Leukemia. Dec. 2016;30(12):2364-2372. doi: 10.1038/leu.2016.136.

Jain, N. et al. Phase II study of the oral MEK inhibitor selumetinib in advanced acute myelogenous leukemia: a University of Chicago phase II consortium trial. Clin Cancer Res. Jan. 15, 2014;20(2):490-8. doi: 10.1158/1078-0432. CCR-13-1311.

Pemovska, T. et al. Individualized systems medicine strategy to tailor treatments for patients with chemorefractory acute myeloid leukemia. Cancer Discov. Dec. 2013;3(12):1416-29. doi: 10.1158/2159-8290.CD-13-0350.

Zhang, W. et al. Evaluation of apoptosis induction by concomitant inhibition of MEK, mTOR, and Bcl-2 in human acute myelogenous leukemia cells. Mol Cancer Ther. Jul. 2014;13(7):1848-59. doi: 10.1158/1535-7163.MCT-13-0576.

Milella, M. et al. MEK blockade converts AML differentiating response to retinoids into extensive apoptosis. Blood. Mar. 1, 2007;109(5):2121-9. doi: 10.1182/blood-2006-05-024679.

Wei, C.R. et al. MEK inhibitor CI-1040 induces apoptosis in acute myeloid leukemia cells in vitro. Eur Rev Med Pharmacol Sci. May 2016;20(10):1961-8.

\* cited by examiner

TREATMENTS FOR MUTATIONS IN ACUTE MYELOID LEUKEMIA

RELATED APPLICATIONS

This application is the National Stage entry under 35 U.S.C. § 371 of International Application No. PCT/US2019/043759, entitled "TREATMENTS FOR MUTATIONS IN ACUTE MYELOID LEUKEMIA," filed Jul. 26, 2019, which claims priority to U.S. Provisional Patent Application No. 62/711,452, entitled "TREATMENTS FOR MUTATIONS IN ACUTE MYELOID LEUKEMIA," filed on Jul. 27, 2018, each of which is incorporated herein by reference in its entirety.

FEDERALLY SPONSORED RESEARCH OR DEVELOPMENT

This invention was made with government support under U01 CA217862, U54 CA224019, and P30 CA069533 awarded by the National Institutes of Health. The government has certain rights in the invention.

TECHNICAL FIELD

The present invention relates to useful methods of treating Acute Myeloid Leukemia (AML) in a human. Particularly, the invention relates to useful methods of treatment for AML in the presence of gene mutations.

BACKGROUND OF THE INVENTION

Approximately 21,000 people are diagnosed with acute myeloid leukemia (AML) with over 10,000 AML-related deaths annually in the United States[1,2]. Cytogenetic and sequencing analyses have revealed at least 11 genetic classes of AML[3] and over 20 subsets can be assigned when also considering cell differentiation states of the leukemic blasts[4,5]. Deep sequencing of AML by The Cancer Genome Atlas (TCGA) revealed a heterogeneous disease with nearly 2,000 somatically mutated genes observed across 200 patients[6]. Many of the recurrent cytogenetic events and somatic mutations have been shown to carry prognostic significance[3,7,8]. Some of the most frequent somatic variants can also be observed in myelodysplastic syndromes (MDS) and myeloproliferative neoplasms (MPN)[9-11] that can transform into AML. These same mutations have also been observed in healthy individuals exhibiting age-related clonal hematopoiesis, which carries significant risk for the development of MDS, MPN, and AML[12-15].

A small number of therapies targeted to mutational events have been developed for AML patients, with the current standard of care largely unchanged over the past 30-40 years. The first targeted therapy for AML involved use of all-trans retinoic acid (ATRA) in combination with arsenic trioxide for patients with rearrangement of the retinoic acid receptor[16,17]. More recently, FLT3 tyrosine kinase inhibitors have been developed for FLT3 mutational events that occur in ~20-30% of AML patients[18-21]. FLT3 inhibitors deployed as single agents yielded responses of only 2-6 months[22-25]. Midostaurin, a broad-spectrum FLT3 inhibitor, was recently approved for use in newly diagnosed, FLT3-mutated AML patients in combination with standard of care chemotherapy[26]; however, relapse was still prevalent in this setting. Mechanisms underlying relapse on FLT3 inhibitors include acquisition of secondary mutations of FLT3[27], mutations in alternative genes/pathways, such as TET2[28], and tumor-extrinsic signals such as FLT3 ligand and FGF2[29,30]. Targeting of mutant IDH1 and IDH2[31], has shown clinical benefit leading to approval of the IDH2 inhibitor, enasidenib, with approval pending for the IDH1 inhibitor, ivosidenib[32,33] Additional proposed strategies have included inhibition of epigenetic modifiers such as EZH2[34], LSD1[35], and DOT1L[36] based on direct mutation of these targets or synthetic lethality in the context of drug combinations (ATRA and LSD1 inhibitors) or specific genetic features (KMT2A-gene rearrangement for DOT1L inhibitors). Hypomethylating agents have been employed in AML patients with better responses reported for certain genetic subsets, such as those with mutation of TET2[37] or TP53[38]. Most recently, the BCL2 inhibitor, venetoclax, showed a ~20% response rate when used as a single agent in relapsed patients[39] with higher response rates (~60%) reported in combination with hypomethylating agents in newly diagnosed, elderly AML patients[40].

SUMMARY OF THE INVENTION

The present invention provides methods of treatment for Acute Myeloid Leukemia in a human, wherein mutations are present in the genes frequently associated in AML, including mutations in one or more genes selected from the group of NPM1, ASXL1, DNMT3A, NRAS, CBF3.MYH11, IDH1, IDH2, FLT3, FLT3-ITD, MLLT3-KMT2A, MYC, CEBPA, PDS5B, SRSF2, BCOR, RUNX1, RUNX1T1, TET2, WT1, U2AF1, KIT, KRSR2, PML.RARA, SMC1A, CELSR2, PML-RARA, TRIO, and MLLT3.KMT2A.

Also provided are methods of treatment for the mutated conditions above, each generally comprising the steps of: a) obtaining a biological sample from a living human subject or patient with Acute Myeloid Leukemia; detecting whether a particular mutation described herein is present or absent in the biological sample by contacting the biological sample with a probe that binds to the particular mutation; detecting binding between the probe and the protein or gene in question; and, in the presence of binding associated with a particular mutation, administering to the human in need thereof a pharmaceutically or therapeutically effective amount of a specified drug or drugs referenced for the mutation herein.

DETAILED DESCRIPTION OF THE INVENTION

Figure 1:
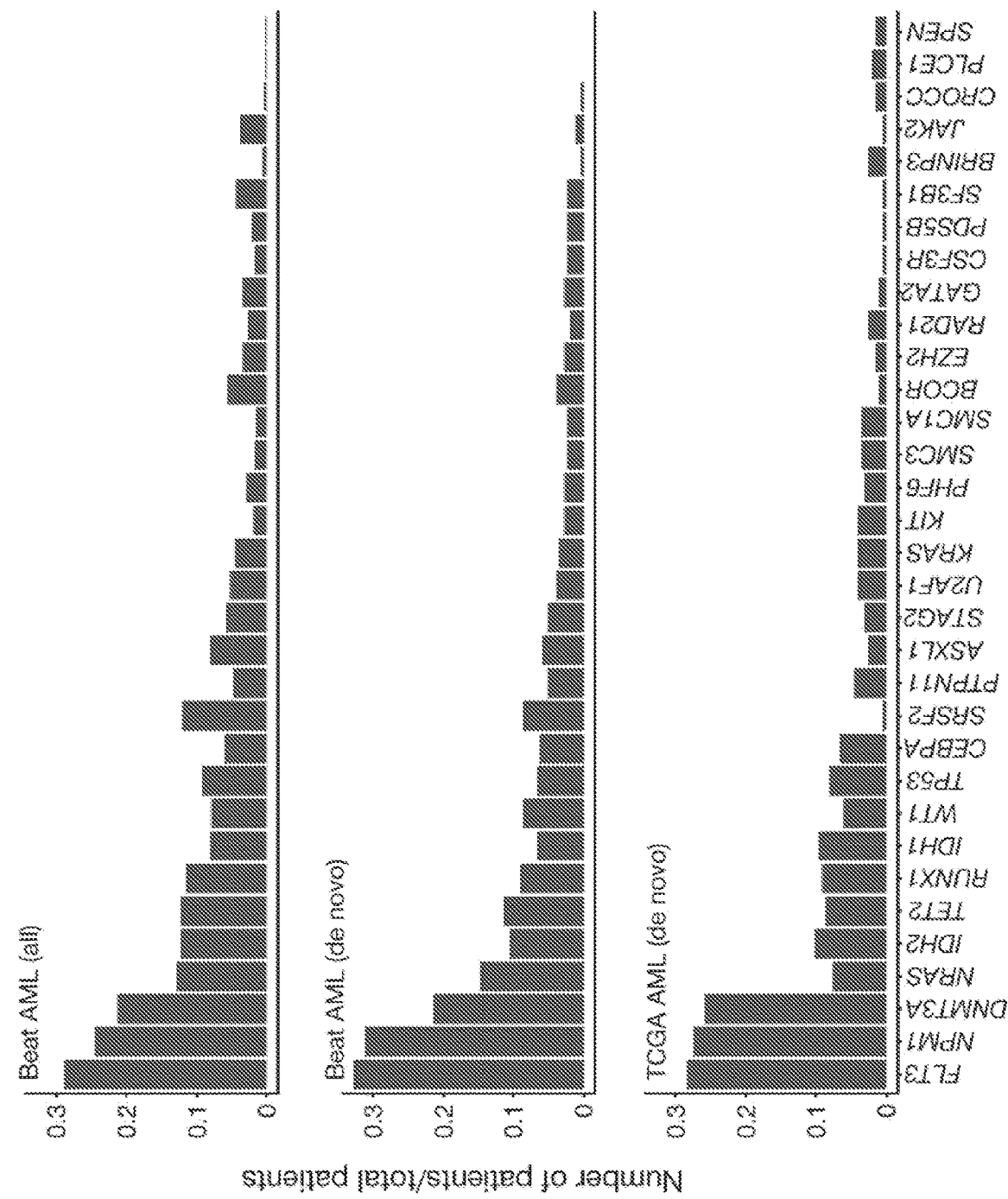
FIG. 1 provides a comparison of the whole Beat AML cohort as well as only the de novo cases in Beat AML with TCGA.

Provided herein are methods for use in the treatment of Acute Myeloid Leukemia in human subjects presenting with AML-associated gene mutations. Included are methods of treatment AML patients who present with mutations to one or more genes selected from the group of NPM1 (nucleophosmin 1), DNMT3A (DNA Methyltransferase 3 Alpha), NRAS (Neuroblastoma RAS), CBFβ.MYH11 (core-binding factor subunit beta.myosin heavy chain 11 fusion); IDH2 (isocitrate dehydrogenase 2); FLT3 (Fms Related Tyrosine Kinase 3); SRSF2 (Serine and Arginine Rich Splicing Factor 2); BCOR (BCL6 Corepressor); RUNX1 (Runt Related Transcription Factor 1); RUNX1T1 (RUNX1 Translocation Partner 1); TET2 (tet methylcytosine dioxygenase 2); WT1 (Wilms tumor 1); U2AF1 (U2 Small Nuclear RNA Auxilliary Factor 1); KIT (KIT proto-oncogene receptor tyrosine kinase); ZRSR2 (zinc finger CCCH-type, RNA binding motif and serine/arginine rich 2); PML.RARA (promyelocytic leukemia.Retinoic acid receptor alpha); MLLT3.KMT2A (myeloid/lymphoid or mixed-lineage leukemia, translocated to 3.Lysine methyltransferase 2A).

NPM1 Mutations

Mutations in NPM1 are usually restricted to exon 12, as shown in an analysis of 52 primary AML patients with cytoplasmic NPM1 (NPM1c), where 98% of the patients had exon 12 mutations. To date, >55 unique mutations have been identified in exon 12 of NPM1. Most mutations consist of a (net) 4 bp insertion with >95% of mutations occurring between nucleotides 960 and 961, however, there have also been cases (<5%) that occur within 10 nucleotides up or downstream. The most common mutation is called type A constituting ~80% of cases; type A mutations involve duplication of TCTG (nucleotides 956-959), creating an insertion at position 960. Type B and D mutations are also fairly common, both producing 4 bp insertions at position 960. Other mutations are rare, occurring in <1% of cases. Additionally, the frequency of nonexon 12 mutations is unknown, as most large studies restrict their analysis to exon 12. Discussion of these NPM1 mutations is discussed by Heath et al., Leukemia (2017) 31, pp. 798-807.

Provided is a method of treating Acute Myeloid Leukemia in a human, wherein the Acute Myeloid Leukemia is characterized by a mutation in the NPM1 gene, the method comprising administering to the human in need thereof a therapeutically effective amount of a drug selected from the group of ibrutinib, vandetanib, lenvatinib, sorafenib, regorafenib, cabozantinib, foretinib, and entospletinib, or a pharmaceutically acceptable salt thereof.

Provided is a method of treating Acute Myeloid Leukemia in a human, wherein the Acute Myeloid Leukemia is characterized by a mutation in the NPM1 gene, the method comprising administering to the human in need thereof a therapeutically effective amount of ibrutinib, or a pharmaceutically acceptable salt thereof.

Provided is a method of treating Acute Myeloid Leukemia in a human, wherein the Acute Myeloid Leukemia is characterized by a mutation in the NPM1 gene, the method comprising administering to the human in need thereof a therapeutically effective amount of vandetanib, or a pharmaceutically acceptable salt thereof.

Provided is a method of treating Acute Myeloid Leukemia in a human, wherein the Acute Myeloid Leukemia is characterized by a mutation in the NPM1 gene, the method comprising administering to the human in need thereof a therapeutically effective amount of lenvatinib, or a pharmaceutically acceptable salt thereof.

Provided is a method of treating Acute Myeloid Leukemia in a human, wherein the Acute Myeloid Leukemia is characterized by a mutation in the NPM1 gene, the method comprising administering to the human in need thereof a therapeutically effective amount of sorafenib, or a pharmaceutically acceptable salt thereof.

Provided is a method of treating Acute Myeloid Leukemia in a human, wherein the Acute Myeloid Leukemia is characterized by a mutation in the NPM1 gene, the method comprising administering to the human in need thereof a therapeutically effective amount of regorafenib, or a pharmaceutically acceptable salt thereof.

Provided is a method of treating Acute Myeloid Leukemia in a human, wherein the Acute Myeloid Leukemia is characterized by a mutation in the NPM1 gene, the method comprising administering to the human in need thereof a therapeutically effective amount of cabozantinib, or a pharmaceutically acceptable salt thereof.

Provided is a method of treating Acute Myeloid Leukemia in a human, wherein the Acute Myeloid Leukemia is characterized by a mutation in the NPM1 gene, the method comprising administering to the human in need thereof a therapeutically effective amount of foretinib, or a pharmaceutically acceptable salt thereof.

Provided is a method of treating Acute Myeloid Leukemia in a human, wherein the Acute Myeloid Leukemia is characterized by a mutation in the NPM1 gene, the method comprising administering to the human in need thereof a therapeutically effective amount of entospletinib, or a pharmaceutically acceptable salt thereof.

Also provided is a method of treating Acute Myeloid Leukemia in a human in need thereof where the Acute Myeloid Leukemia is characterized by a mutation in the NPM1 gene, the method comprising the steps of:
  a) collecting from the human a sample of blood;
  b) detecting the presence of a mutation in NPM1 in the sample;
  c) administering to the human a therapeutically effective amount of one or more drugs selected from the group of ibrutinib, vandetanib, lenvatinib, sorafenib, regorafenib, cabozantinib, foretinib, and entospletinib, or a pharmaceutically acceptable salt thereof.

Within each of the methods herein concerning a mutation in NPM1, there is a further embodiment comprising each of the steps of the individual method in question in which the mutation in NPM1 is a mutation at exon 12.

Within each of the methods herein concerning a mutation in NPM1, there is a further embodiment comprising each of the steps of the individual method in question in which the mutation in NPM1 is a mutation comprising an insertion of from one to four base pairs occurring within 10 nucleotides upstream or downstream of between nucleotides 960 and 961.

Within each of the methods herein concerning a mutation in NPM1, there is a further embodiment comprising each of the steps of the individual method in question in which the mutation in NPM1 is a mutation comprising a duplication of TCTG (nucleotides 956-959), creating an insertion at position 960.

Also provided is one or more drugs selected from the group of ibrutinib, vandetanib, lenvatinib, sorafenib, regorafenib, cabozantinib, foretinib, and entospletinib, or a pharmaceutically acceptable salt thereof, for use in treating Acute Myeloid Leukemia characterized by a mutation in the NPM1 gene. It is understood that each drug in this list may be used separately for use in treating Acute Myeloid Leukemia characterized by a mutation in the NPM1 gene and eight separate embodiments herein concern the use of each drug independently for that use.

NPM1:DNMT3A:NRAS Mutations

Provided is a method of treating acute myeloid leukemia in a human, wherein at least two mutations selected from the group of NPM1, DNMT3A, and NRAS mutations are present, the method comprising administering to the human in need thereof a therapeutically effective amount of ibrutinib, or a pharmaceutically acceptable salt thereof.

Provided is a method of treating acute myeloid leukemia in a human, wherein NPM1, DNMT3A, and NRAS mutations are present, the method comprising administering to the human in need thereof a therapeutically effective amount of ibrutinib, or a pharmaceutically acceptable salt thereof.

Provided is a method of treating acute myeloid leukemia in a human, wherein NPM1 and DNMT3A mutations are present, the method comprising administering to the human in need thereof a therapeutically effective amount of ibrutinib, or a pharmaceutically acceptable salt thereof.

Also provided is a method of treating Acute Myeloid Leukemia in a human in need thereof where the Acute Myeloid Leukemia is characterized by at least two mutations in genes selected from the group of NPM1, DNMT3A, and NRAS gene, the method comprising the steps of:
  a) collecting from the human a sample of blood;
  b) detecting the presence of a mutation in at least two mutations in genes selected from the group of NPM1, DNMT3A, and NRAS in the sample;
  c) administering to the human a therapeutically effective amount of ibrutinib, or a pharmaceutically acceptable salt thereof.

Further provided is a method of treating Acute Myeloid Leukemia in a human in need thereof where the Acute Myeloid Leukemia is characterized by a mutation in each of the NPM1, DNMT3A, and NRAS genes, the method comprising the steps of:
  a) collecting from the human a sample of blood;
  b) detecting the presence of a mutation in in each of the NPM1, DNMT3A, and NRAS genes in the sample;
  c) administering to the human a therapeutically effective amount of ibrutinib, or a pharmaceutically acceptable salt thereof.

Also provided is ibrutinib, or a pharmaceutically acceptable salt thereof, for use in treating Acute Myeloid Leukemia characterized by a mutation in at least two of the genes selected from the group of NPM1, DNMT3A, and NRAS.

Also provided is ibrutinib, or a pharmaceutically acceptable salt thereof, for use in treating Acute Myeloid Leukemia characterized by a mutation in each of the genes selected from the group of NPM1, DNMT3A, and NRAS.

NPM1:DNMT3A:FLT3 or NRAS Mutations

Provided is a method of treating AML in a human, wherein NPM1, DNMT3A, and FLT3 mutations are present, the method comprising administering to the human in need thereof a therapeutically effective amount of ibrutinib, or a pharmaceutically acceptable salt thereof.

Also provided is a method of treating AML in a human, wherein NPM1 and DNMT3A mutations are present and at least one mutation selected from NRAS and FLT3 mutations is present, the method comprising administering to the human in need thereof a therapeutically effective amount of ibrutinib, or a pharmaceutically acceptable salt thereof.

Also provided is a method of treating Acute Myeloid Leukemia in a human in need thereof where the Acute Myeloid Leukemia is characterized by a mutation in each of the NPM1, DNMT3A, and FLT3 genes, the method comprising the steps of:
  a) collecting from the human a sample of blood;
  b) detecting the presence of a mutation in each of the NPM1, DNMT3A, and FLT3 genes in the sample; and
  c) administering to the human a therapeutically effective amount of ibrutinib, or a pharmaceutically acceptable salt thereof.

Further provided is a method of treating Acute Myeloid Leukemia in a human in need thereof where the Acute Myeloid Leukemia is characterized by a mutation in each of the NPM1 and DNMT3A genes and at least one mutation in a gene selected from the group of NRAS and FLT3, the method comprising the steps of:
  a) collecting from the human a sample of blood;
  b) detecting the presence of a mutation in each of the NPM1 and DNMT3A and a mutation in at least one of the NRAS and FLT3 genes in the sample; and
  c) administering to the human a therapeutically effective amount of ibrutinib, or a pharmaceutically acceptable salt thereof.

Also provided is ibrutinib, or a pharmaceutically acceptable salt thereof, for use in treating Acute Myeloid Leukemia characterized by a mutation in each of the genes selected from the group of NPM1 and DNMT3A and characterized by a mutation in at least one of the genes selected from the group of NRAS and FLT3

Also provided is ibrutinib, or a pharmaceutically acceptable salt thereof, for use in treating Acute Myeloid Leukemia characterized by a mutation in each of the genes selected from the group of NPM1, DNMT3A, and FLT3.

Also provided is ibrutinib, or a pharmaceutically acceptable salt thereof, for use in treating Acute Myeloid Leukemia characterized by a mutation in each of the genes selected from the group of NPM1, DNMT3A, NRAS, and FLT3.

NPM1:FLT3 Mutations

Provided is a method of treating acute myeloid leukemia in a human, wherein NPM1 and FLT3 mutations are present, the method comprising administering to the human in need thereof a therapeutically effective amount of a drug selected from the group of sorafenib, cabozantinib, and entospletinib, or a pharmaceutically acceptable salt thereof.

Provided is a method of treating acute myeloid leukemia in a human, wherein NPM1 and FLT3 mutations are present, the method comprising administering to the human in need thereof a therapeutically effective amount of sorafenib, or a pharmaceutically acceptable salt thereof.

Provided is a method of treating acute myeloid leukemia in a human, wherein NPM1 and FLT3 mutations are present, the method comprising administering to the human in need thereof a therapeutically effective amount of cabozantinib, or a pharmaceutically acceptable salt thereof.

Provided is a method of treating acute myeloid leukemia in a human, wherein NPM1 and FLT3 mutations are present, the method comprising administering to the human in need thereof a therapeutically effective amount of entospletinib, or a pharmaceutically acceptable salt thereof.

Also provided is a method of treating Acute Myeloid Leukemia in a human in need thereof where the Acute Myeloid Leukemia is characterized by a mutation in each of the NPM1 and FLT3 genes, the method comprising the steps of:
  a) collecting from the human a sample of blood;
  b) detecting the presence of a mutation in NPM1 and FLT3 genes in the sample; and c) administering to the human a therapeutically effective amount of a drug selected from the group of sorafenib, cabozantinib, and entospletinib, or a pharmaceutically acceptable salt thereof.

Also provided is one or more drugs selected from the group of sorafenib, cabozantinib, and entospletinib, or a pharmaceutically acceptable salt thereof, for use in treating Acute Myeloid Leukemia characterized by a mutation in the NPM1 and FLT3 genes. It is understood that each drug in this list may be used separately for use in treating Acute Myeloid Leukemia characterized by a mutation in the NPM1 and FLT3 genes and three separate embodiments herein concern the use of each drug independently for that use.

NPM1:IDH2 Mutations

Provided is a method of treating acute myeloid leukemia in a human, wherein NPM1 and IDH2 mutations are present, the method comprising administering to the human in need thereof a therapeutically effective amount of vandetanib, or a pharmaceutically acceptable salt thereof.

Further provided is a method of treating acute myeloid leukemia in a human, wherein NPM1 and IDH2 mutations are present, the method comprising administering to the human in need thereof a therapeutically effective amount of NF-kB activation inhibitor, or a pharmaceutically acceptable salt thereof.

Also provided is a method of treating Acute Myeloid Leukemia in a human in need thereof where the Acute Myeloid Leukemia is characterized by a mutation in each of the NPM1 and IDH2 genes, the method comprising the steps of:
  a) collecting from the human a sample of blood;
  b) detecting the presence of a mutation in each of the NPM1 and IDH2 genes in the sample;
  c) administering to the human a therapeutically effective amount of a drug selected from the group of vandetanib and NF-kB activation inhibitor, or a pharmaceutically acceptable salt thereof.

Also provided is one or more drugs selected from the group of vandetanib and NF-kB activation inhibitor, or a pharmaceutically acceptable salt thereof, for use in treating Acute Myeloid Leukemia characterized by a mutation in the NPM1 and IDH2 genes. It is understood that each drug in this list may be used separately for use in treating Acute Myeloid Leukemia characterized by a mutation in the NPM1 and IDH2 genes and two separate embodiments herein concern the use of each drug, vandetanib and NF-kB activation inhibitor, independently for that use.

NPM1:DNMT3A Mutations

Provided is a method of treating acute myeloid leukemia in a human, wherein NPM1 and DNMT3A mutations are present, the method comprising administering to the human in need thereof a therapeutically effective amount of one or more drugs selected from the group of lenvatinib, ibrutinib, saracatinib, and regorafenib, or a pharmaceutically acceptable salt thereof.

Also provided is a method of treating acute myeloid leukemia in a human, wherein NPM1 and DNMT3A mutations are present, the method comprising administering to the human in need thereof a therapeutically effective amount of lenvatinib, or a pharmaceutically acceptable salt thereof.

Further provided is a method of treating acute myeloid leukemia in a human, wherein NPM1 and DNMT3A mutations are present, the method comprising administering to the human in need thereof a therapeutically effective amount of ibrutinib, or a pharmaceutically acceptable salt thereof.

Also provided is a method of treating acute myeloid leukemia in a human, wherein NPM1 and DNMT3A mutations are present, the method comprising administering to the human in need thereof a therapeutically effective amount of saracatinib, or a pharmaceutically acceptable salt thereof.

Provided is a method of treating acute myeloid leukemia in a human, wherein NPM1 and DNMT3A mutations are present, the method comprising administering to the human in need thereof a therapeutically effective amount of regorafenib, or a pharmaceutically acceptable salt thereof.

Also provided is a method of treating Acute Myeloid Leukemia in a human in need thereof where the Acute Myeloid Leukemia is characterized by a mutation in each of the NPM1 and DNMT3A genes, the method comprising the steps of:
  a) collecting from the human a sample of blood;
  b) detecting the presence of a mutation in NPM1 and DNMT3A genes in the sample;
  c) administering to the human a therapeutically effective amount of one or more drugs selected from the group of lenvatinib, ibrutinib, saracatinib, and regorafenib, or a pharmaceutically acceptable salt thereof.

Also provided is one or more drugs selected from the group of lenvatinib, ibrutinib, saracatinib, and regorafenib, or a pharmaceutically acceptable salt thereof, for use in treating Acute Myeloid Leukemia characterized by a mutation in the NPM1 and DNMT3A genes. It is understood that each drug in this list may be used separately for use in treating Acute Myeloid Leukemia characterized by a mutation in the NPM1 and DNMT3A genes and four separate embodiments herein concern the use of each drug, lenvatinib, ibrutinib, saracatinib, and regorafenib, independently for that use.

NPM1:TET2 Mutations

Provided is a method of treating acute myeloid leukemia in a human, wherein NPM1 and TET2 mutations are present, the method comprising administering to the human in need thereof a therapeutically effective amount of ibrutinib, or a pharmaceutically acceptable salt thereof.

Also provided is a method of treating Acute Myeloid Leukemia in a human in need thereof where the Acute Myeloid Leukemia is characterized by a mutation in each of the NPM1 and TET2 genes, the method comprising the steps of:
  a) collecting from the human a sample of blood;
  b) detecting the presence of a mutation in the NPM1 and TET2 genes in the sample;
  c) administering to the human a therapeutically effective amount of ibrutinib, or a pharmaceutically acceptable salt thereof.

Also provided is ibrutinib, or a pharmaceutically acceptable salt thereof, for use in treating Acute Myeloid Leukemia characterized by a mutation in each of the genes selected from the group of NPM1 and TET2.

CBFB.MYH11:NRAS Mutations

Provided is a method of treating acute myeloid leukemia in a human, wherein CBFB.MYH11 and NRAS mutations are present, the method comprising administering to the human in need thereof a therapeutically effective amount of trametinib, or a pharmaceutically acceptable salt thereof.

Provided is a method of treating acute myeloid leukemia in a human, wherein CBFB.MYH11 and NRAS mutations are present, the method comprising administering to the human in need thereof a therapeutically effective amount of YM-155, or a pharmaceutically acceptable salt thereof.

Also provided is a method of treating Acute Myeloid Leukemia in a human in need thereof where the Acute Myeloid Leukemia is characterized by a mutation in each of the CBFB.MYH11 and NRAS genes, the method comprising the steps of:
- a) collecting from the human a sample of blood;
- b) detecting the presence of a mutation in the CBFB.MYH11 and NRAS genes in the sample;
- c) administering to the human a therapeutically effective amount of a compound selected from then group of trametinib and YM-155, or a pharmaceutically acceptable salt thereof.

Also provided is one or more drugs selected from the group of trametinib and YM-155, or a pharmaceutically acceptable salt thereof, for use in treating Acute Myeloid Leukemia characterized by a mutation in the CBFB.MYH11 and NRAS genes. It is understood that each drug in this list may be used separately for use in treating Acute Myeloid Leukemia characterized by a mutation in the CBFB.MYH11 and NRAS genes and two separate embodiments herein concern the use of each drug, trametinib and YM-155, independently for that use.

IDH2:FLT3 Mutations

Provided is a method of treating acute myeloid leukemia in a human, wherein IDH2 and FLT3 mutations are present, the method comprising administering to the human in need thereof a therapeutically effective amount of sorafenib, or a pharmaceutically acceptable.

Also provided is a method of treating Acute Myeloid Leukemia in a human in need thereof where the Acute Myeloid Leukemia is characterized by a mutation in each of the IDH2 and FLT3 genes, the method comprising the steps of:
- a) collecting from the human a sample of blood;
- b) detecting the presence of a mutation in the IDH2 and FLT3 genes in the sample;
- c) administering to the human a therapeutically effective amount of sorafenib, or a pharmaceutically acceptable salt thereof.

Also provided is sorafenib, or a pharmaceutically acceptable salt thereof, for use in treating Acute Myeloid Leukemia characterized by a mutation in each of the genes selected from the group of IDH2 and FLT3.

SRSF2:IDH2 Mutations

Also provided is a method of treating acute myeloid leukemia in a human, wherein SRSF2 and IDH2 mutations are present, the method comprising administering to the human in need thereof a therapeutically effective amount of crizotinib, or a pharmaceutically acceptable salt thereof.

Also provided is a method of treating Acute Myeloid Leukemia in a human in need thereof where the Acute Myeloid Leukemia is characterized by a mutation in each of the SRSF2 and IDH2 genes, the method comprising the steps of:
- a) collecting from the human a sample of blood;
- b) detecting the presence of a mutation in each of the SRSF2 and IDH2 genes in the sample;
- c) administering to the human a therapeutically effective amount of crizotinib, or a pharmaceutically acceptable salt thereof.

Also provided is crizotinib, or a pharmaceutically acceptable salt thereof, for use in treating Acute Myeloid Leukemia characterized by a mutation in each of the genes selected from the group of SRSF2 and IDH2.

BCOR:RUNX1 Mutations

Provided is a method of treating acute myeloid leukemia in a human, wherein BCOR and RUNX1 mutations are present, the method comprising administering to the human in need thereof a therapeutically effective amount of a JAK kinase inhibitor, or a pharmaceutically acceptable salt thereof.

Also provided is a method of treating Acute Myeloid Leukemia in a human in need thereof where the Acute Myeloid Leukemia is characterized by a mutation in the BCOR and RUNX1 genes, the method comprising the steps of:
- a) collecting from the human a sample of blood;
- b) detecting the presence of a mutation in the BCOR and RUNX1 genes in the sample;
- c) administering to the human a therapeutically effective amount of a JAK kinase inhibitor, or a pharmaceutically acceptable salt thereof.

Also provided is a JAK kinase inhibitor, or a pharmaceutically acceptable salt thereof, for use in treating Acute Myeloid Leukemia characterized by a mutation in each of the genes selected from the group of BCOR and RUNX1.

In some embodiments of the methods above, the JAK kinase inhibitor is selected from the group of momelotinib, ruxolitinib, tofacitinib, baricitinib, filgotinib (G-146034, GLPG-0634), gandotinib, lestaurtinib (CEP-701), pacritinib (SB1518), PF-04965842, upadacitinib (ABT-494), peficitinib (ASP015K, JNJ-54781532), fedratinib (SAR302503), cucurbitacin (JSI-1214), and CZ868, or a pharmaceutically acceptable salt thereof. In other embodiments the JAK kinase inhibitor is selected from the group of momelotinib, ruxolitinib, and tofacitinib, or a pharmaceutically acceptable salt thereof.

NRAS Mutations

Provided is a method of treating acute myeloid leukemia in a human, wherein an NRAS mutation is present, the method comprising administering to the human in need thereof a therapeutically effective amount of one or more drugs selected from the group of selumetinib, trametinib, and flavopiridol, or a pharmaceutically acceptable salt thereof.

Also provided is a method of treating acute myeloid leukemia in a human, wherein an NRAS mutation is present, the method comprising administering to the human in need thereof a therapeutically effective amount of selumetinib, or a pharmaceutically acceptable salt thereof.

Additionally provided is a method of treating acute myeloid leukemia in a human, wherein an NRAS mutation is present, the method comprising administering to the human in need thereof a therapeutically effective amount of trametinib, or a pharmaceutically acceptable salt thereof.

Further provided is a method of treating acute myeloid leukemia in a human, wherein an NRAS mutation is present, the method comprising administering to the human in need thereof a therapeutically effective amount of flavopiridol, or a pharmaceutically acceptable salt thereof.

Also provided is a method of treating Acute Myeloid Leukemia in a human in need thereof where the Acute Myeloid Leukemia is characterized by a mutation in the NRAS genes, the method comprising the steps of:
- a) collecting from the human a sample of blood;
- b) detecting the presence of a mutation in the NRAS gene in the sample;
- c) administering to the human a therapeutically effective amount of one or more drugs selected from the group of selumetinib, trametinib, and flavopiridol, or a pharmaceutically acceptable salt thereof.

Also provided is one or more drugs selected from the group of selumetinib, trametinib, and flavopiridol, or a pharmaceutically acceptable salt thereof, for use in treating Acute Myeloid Leukemia characterized by a mutation in the NRAS gene. It is understood that each drug in this list may be used separately for use in treating Acute Myeloid Leukemia characterized by a mutation in the NRAS gene and three separate embodiments herein concern the use of each drug, selumetinib, trametinib, and flavopiridol, independently for that use.

WT1 Mutations

Provided is a method of treating acute myeloid leukemia in a human, wherein a WT1 mutation is present, the method comprising administering to the human in need thereof a therapeutically effective amount of RAF265 (CHIR-265), or a pharmaceutically acceptable salt thereof.

Also provided is a method of treating Acute Myeloid Leukemia in a human in need thereof where the Acute Myeloid Leukemia is characterized by a mutation in the WT1 gene, the method comprising the steps of:
  a) collecting from the human a sample of blood;
  b) detecting the presence of a mutation in the WT1 gene in the sample;
  c) administering to the human a therapeutically effective amount of RAF265 (CHIR-265), or a pharmaceutically acceptable salt thereof.

Also provided is RAF265 (CHIR-265), or a pharmaceutically acceptable salt thereof, for use in treating Acute Myeloid Leukemia characterized by a mutation in the WT1 gene.

RAF265 is also known by the chemical name 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine.

FLT3 Mutations

Provided is a method of treating acute myeloid leukemia in a human, wherein a FLT3 mutation is present, the method comprising administering to the human in need thereof a therapeutically effective amount of one or more drugs selected from the group of sorafenib, quizartinib, cabozantinib, foretinib, sunitinib, and regorafenib, or a pharmaceutically acceptable salt thereof.

Provided is a method of treating acute myeloid leukemia in a human, wherein a FLT3 mutation is present, the method comprising administering to the human in need thereof a therapeutically effective amount of sorafenib, or a pharmaceutically acceptable salt thereof.

Provided is a method of treating acute myeloid leukemia in a human, wherein a FLT3 mutation is present, the method comprising administering to the human in need thereof a therapeutically effective amount of quizartinib, or a pharmaceutically acceptable salt thereof.

Provided is a method of treating acute myeloid leukemia in a human, wherein a FLT3 mutation is present, the method comprising administering to the human in need thereof a therapeutically effective amount of cabozantinib, or a pharmaceutically acceptable salt thereof.

Provided is a method of treating acute myeloid leukemia in a human, wherein a FLT3 mutation is present, the method comprising administering to the human in need thereof a therapeutically effective amount of foretinib, or a pharmaceutically acceptable salt thereof.

Provided is a method of treating acute myeloid leukemia in a human, wherein a FLT3 mutation is present, the method comprising administering to the human in need thereof a therapeutically effective amount of sunitinib, or a pharmaceutically acceptable salt thereof.

Provided is a method of treating acute myeloid leukemia in a human, wherein a FLT3 mutation is present, the method comprising administering to the human in need thereof a therapeutically effective amount of regorafenib, or a pharmaceutically acceptable salt thereof.

Also provided is a method of treating Acute Myeloid Leukemia in a human in need thereof where the Acute Myeloid Leukemia is characterized by a mutation in the FLT3 gene, the method comprising the steps of:
  a) collecting from the human a sample of blood;
  b) detecting the presence of a mutation in the FLT3 gene in the sample;
  c) administering to the human a therapeutically effective amount of one or more drugs selected from the group of sorafenib, quizartinib, cabozantinib, foretinib, sunitinib, and regorafenib, or a pharmaceutically acceptable salt thereof.

Also provided is one or more drugs selected from the group of sorafenib, quizartinib, cabozantinib, foretinib, sunitinib, and regorafenib, or a pharmaceutically acceptable salt thereof, for use in treating Acute Myeloid Leukemia characterized by a mutation in the FLT3 gene. It is understood that each drug in this list may be used separately for use in treating Acute Myeloid Leukemia characterized by a mutation in the FLT3 gene and six separate embodiments herein concern the use of each drug, sorafenib, quizartinib, cabozantinib, foretinib, sunitinib, and regorafenib, independently for that use.

IDH2 Mutations

Provided is a method of treating acute myeloid leukemia in a human, wherein an IDH2 mutation other than a FLT3/ITD mutation is present, the method comprising administering to the human in need thereof a therapeutically effective amount of one or more drugs selected from the group of crizotinib and lenvatinib, or a pharmaceutically acceptable salt thereof.

Provided is a method of treating acute myeloid leukemia in a human, wherein an IDH2 mutation other than a FLT3/ITD mutation is present, the method comprising administering to the human in need thereof a therapeutically effective amount of crizotinib, or a pharmaceutically acceptable salt thereof.

Provided is a method of treating acute myeloid leukemia in a human, wherein an IDH2 mutation other than a FLT3/ITD mutation is present, the method comprising administering to the human in need thereof a therapeutically effective amount of lenvatinib, or a pharmaceutically acceptable salt thereof.

Also provided is a method of treating Acute Myeloid Leukemia in a human in need thereof where the Acute Myeloid Leukemia is characterized by a mutation in the IDH2 gene other than a FLT3/ITD mutation, the method comprising the steps of:
  a) collecting from the human a sample of blood;
  b) detecting the presence of a mutation in the IDH2 gene other than a FLT3/ITD mutation in the sample;
  c) administering to the human a therapeutically effective amount of one or more drugs selected from the group of crizotinib and lenvatinib, or a pharmaceutically acceptable salt thereof.

Also provided is one or more drugs selected from the group of crizotinib and lenvatinib, or a pharmaceutically acceptable salt thereof, for use in treating Acute Myeloid Leukemia characterized by a mutation in the IDH2 gene other than a FLT3/ITD mutation. It is understood that each drug in this list may be used separately for use in treating Acute Myeloid Leukemia characterized by a mutation in the IDH2 gene other than a FLT3/ITD mutation and two separate embodiments herein concern the use of each drug, crizotinib and lenvatinib, independently for that use.

CBFB.MYH11 Mutations

Provided is a method of treating acute myeloid leukemia in a human, wherein a CBFB.MYH11 mutation is present, the method comprising administering to the human in need thereof a therapeutically effective amount of one or more drugs selected from the group of crenolanib, trametinib, saracatinib, and dasatinib, or a pharmaceutically acceptable salt thereof.

Also provided is a method of treating Acute Myeloid Leukemia in a human in need thereof where the Acute Myeloid Leukemia is characterized by a mutation in the CBFB.MYH11 gene, the method comprising the steps of:
a) collecting from the human a sample of blood;
b) detecting the presence of a mutation in the CBFB.MYH11 gene in the sample;
c) administering to the human a therapeutically effective amount of one or more drugs selected from the group of crenolanib, trametinib, saracatinib, and dasatinib, or a pharmaceutically acceptable salt thereof.

Also provided is one or more drugs selected from the group of crenolanib, trametinib, saracatinib, and dasatinib, or a pharmaceutically acceptable salt thereof, for use in treating Acute Myeloid Leukemia characterized by a CBFB.MYH11 mutation. It is understood that each drug in this list may be used separately for use in treating Acute Myeloid Leukemia characterized by a CBFB.MYH11 mutation and four separate embodiments herein concern the use of each drug, crenolanib, trametinib, saracatinib, and dasatinib, independently for that use.

PML.RARA Mutations

Provided is a method of treating acute myeloid leukemia in a human, wherein a PML.RARA mutation is present, the method comprising administering to the human in need thereof a therapeutically effective amount of one or more drugs selected from the group of venetoclax, ABT-737, and YM-155, or a pharmaceutically acceptable salt thereof.

Also provided is a method of treating Acute Myeloid Leukemia in a human in need thereof where the Acute Myeloid Leukemia is characterized by a mutation in the PML.RARA gene, the method comprising the steps of:
a) collecting from the human a sample of blood;
b) detecting the presence of a mutation in the PML.RARA gene in the sample;
c) administering to the human a therapeutically effective amount of one or more drugs selected from the group of venetoclax, ABT-737, and YM-155, or a pharmaceutically acceptable salt thereof.

Within each of the two PML.RARA-related methods above, there are separate individual methods in which the drug administered is a) venetoclax, b) ABT-737, and c) YM-155, or a pharmaceutically acceptable salt thereof.

Also provided is one or more drugs selected from the group of venetoclax, ABT-737, and YM-155, or a pharmaceutically acceptable salt thereof, for use in treating Acute Myeloid Leukemia characterized by a PML.RARA mutation. It is understood that each drug in this list may be used separately for use in treating Acute Myeloid Leukemia characterized by a PML.RARA mutation and three separate embodiments herein concern the use of each drug, venetoclax, ABT-737, and YM-155, independently for that use.

RUNX1:RUNX1T1 Mutations

Provided is a method of treating acute myeloid leukemia in a human, wherein RUNX1 and RUNX1T1 mutations are present, the method comprising administering to the human in need thereof a therapeutically effective amount of pazopanib, or a pharmaceutically acceptable salt thereof.

Also provided is a method of treating Acute Myeloid Leukemia in a human in need thereof where the Acute Myeloid Leukemia is characterized by a mutation in the RUNX1 and RUNX1T1 genes, the method comprising the steps of:
a) collecting from the human a sample of blood;
b) detecting the presence of a mutation in the RUNX1 and RUNX1T1 genes in the sample;
c) administering to the human a therapeutically effective amount of pazopanib, or a pharmaceutically acceptable salt thereof.

Also provided is pazopanib, or a pharmaceutically acceptable salt thereof, for use in treating Acute Myeloid Leukemia characterized by a mutation in each of the genes selected from the group of RUNX1 and RUNX1T1.

DNMT3A Mutations

Provided is a method of treating acute myeloid leukemia in a human, wherein a DNMT3A mutation is present, the method comprising administering to the human in need thereof a therapeutically effective amount of lenvatinib, or a pharmaceutically acceptable salt thereof.

Also provided is a method of treating Acute Myeloid Leukemia in a human in need thereof where the Acute Myeloid Leukemia is characterized by a mutation in the DNMT3A gene, the method comprising the steps of:
a) collecting from the human a sample of blood;
b) detecting the presence of a mutation in the DNMT3A gene in the sample;
c) administering to the human a therapeutically effective amount of pazopanib, or a pharmaceutically acceptable salt thereof.

Also provided is pazopanib, or a pharmaceutically acceptable salt thereof, for use in treating Acute Myeloid Leukemia characterized by a mutation in the DNMT3A gene.

IDH1 Mutations

Provided is a method of treating acute myeloid leukemia in a human, wherein an IDH1 mutation is present, the method comprising administering to the human in need thereof a therapeutically effective amount of YM-155, or a pharmaceutically acceptable salt thereof.

Also provided is a method of treating Acute Myeloid Leukemia in a human in need thereof where the Acute Myeloid Leukemia is characterized by a mutation in the IDH1 gene, the method comprising the steps of:
a) collecting from the human a sample of blood;
b) detecting the presence of a mutation in the IDH1 gene in the sample;
c) administering to the human a therapeutically effective amount of YM-155, or a pharmaceutically acceptable salt thereof.

Also provided is YM-155, or a pharmaceutically acceptable salt thereof, for use in treating Acute Myeloid Leukemia characterized by a mutation in the IDH1 gene.

U2AF1 Mutations

Provided is a method of treating acute myeloid leukemia in a human, wherein a U2AF1 mutation is present, the method comprising administering to the human in need thereof a therapeutically effective amount of cediranib, or a pharmaceutically acceptable salt thereof.

Also provided is a method of treating Acute Myeloid Leukemia in a human in need thereof where the Acute Myeloid Leukemia is characterized by a mutation in the U2AF1 gene, the method comprising the steps of:
a) collecting from the human a sample of blood;
b) detecting the presence of a mutation in the U2AF1 gene in the sample;

c) administering to the human a therapeutically effective amount of cediranib, or a pharmaceutically acceptable salt thereof.

Also provided is cediranib, or a pharmaceutically acceptable salt thereof, for use in treating Acute Myeloid Leukemia characterized by a mutation in the U2AF1 gene.

KIT Mutations

Provided is a method of treating acute myeloid leukemia in a human, wherein a KIT mutation is present, the method comprising administering to the human in need thereof a therapeutically effective amount of one or more drugs selected from the group of imatinib, sorafenib, and pazopanib, or a pharmaceutically acceptable salt thereof.

Also provided is a method of treating Acute Myeloid Leukemia in a human in need thereof where the Acute Myeloid Leukemia is characterized by a mutation in the KIT gene, the method comprising the steps of:
 a) collecting from the human a sample of blood;
 b) detecting the presence of a mutation in the KIT gene in the sample;
 c) administering to the human a therapeutically effective amount of one or more drugs selected from the group of imatinib, sorafenib, and pazopanib, or a pharmaceutically acceptable salt thereof.

Within each of the two KIT-related methods above, there are separate individual methods in which the drug administered is a) imatinib, b) sorafenib, and c) pazopanib, or a pharmaceutically acceptable salt thereof.

Also provided is one or more drugs selected from the group of imatinib, sorafenib, and pazopanib, or a pharmaceutically acceptable salt thereof, for use in treating Acute Myeloid Leukemia characterized by a mutation in the KIT gene. It is understood that each drug in this list may be used separately for use in treating Acute Myeloid Leukemia characterized by a mutation in the KIT gene and three separate embodiments herein concern the use of each drug, imatinib, sorafenib, and pazopanib, independently for that use.

ZRSR2 Mutations

Provided is a method of treating acute myeloid leukemia in a human, wherein a ZRSR2 mutation is present, the method comprising administering to the human in need thereof a therapeutically effective amount of tofacitinib, or a pharmaceutically acceptable salt thereof.

Also provided is a method of treating Acute Myeloid Leukemia in a human in need thereof where the Acute Myeloid Leukemia is characterized by a mutation in the ZRSR2 gene, the method comprising the steps of:
 a) collecting from the human a sample of blood;
 b) detecting the presence of a mutation in the ZRSR2 gene in the sample;
 c) administering to the human a therapeutically effective amount of tofacitinib, or a pharmaceutically acceptable salt thereof.

Also provided is tofacitinib, or a pharmaceutically acceptable salt thereof, for use in treating Acute Myeloid Leukemia characterized by a mutation in the ZRSR2 gene.

BCOR Mutations

Provided is a method of treating acute myeloid leukemia in a human, wherein a BCOR mutation is present, the method comprising administering to the human in need thereof a therapeutically effective amount of one or more drugs selected from the group of RAF265 and crizotinib, or a pharmaceutically acceptable salt thereof.

Provided is a method of treating acute myeloid leukemia in a human, wherein a BCOR mutation is present, the method comprising administering to the human in need thereof a therapeutically effective amount of RAF265, or a pharmaceutically acceptable salt thereof.

Provided is a method of treating acute myeloid leukemia in a human, wherein a BCOR mutation is present, the method comprising administering to the human in need thereof a therapeutically effective amount of crizotinib, or a pharmaceutically acceptable salt thereof.

Also provided is a method of treating Acute Myeloid Leukemia in a human in need thereof where the Acute Myeloid Leukemia is characterized by a mutation in the BCOR gene, the method comprising the steps of:
 a) collecting from the human a sample of blood;
 b) detecting the presence of a mutation in the BCOR gene in the sample;
 c) administering to the human a therapeutically effective amount of one or more drugs selected from the group of RAF265 and crizotinib, or a pharmaceutically acceptable salt thereof.

Also provided is one or more drugs selected from the group of RAF265 and crizotinib, or a pharmaceutically acceptable salt thereof, for use in treating Acute Myeloid Leukemia characterized by a mutation in the BCOR gene. It is understood that each drug in this list may be used separately for use in treating Acute Myeloid Leukemia characterized by a mutation in the BCOR gene and two separate embodiments herein concern the use of each drug, RAF265 and crizotinib, independently for that use.

BCOR Mutation

Provided is a method of treatment of Acute Myeloid Leukemia in a human in need thereof, wherein the Acute Myeloid Leukemia is characterized by the presence of a BCOR mutation, the method comprising administering to the human a therapeutically effective amount of at least one agent selected from the group of 1-methyl-5-[[2-[5-(trifluoromethyl)-1H-imidazol-2-yl]-4-pyridinyl]oxy]-N-[4-(trifluoromethyl)phenyl]-2-benzimidazolamine (also known asRAF265 and CHIR-265), crizotinib, and 3,5,7,8-Tetrahydro-2-[4-(trifluoromethyl)phenyl]-4H-thiopyrano[4,3-d]pyrimidin-4-one (XAV-939), or a pharmaceutically acceptable salt thereof.

Provided is a method of treatment of Acute Myeloid Leukemia in a human in need thereof, wherein the Acute Myeloid Leukemia is characterized by the presence of a BCOR mutation, the method comprising administering to the human a therapeutically effective amount of 1-methyl-5-[[2-[5-(trifluoromethyl)-1H-imidazol-2-yl]-4-pyridinyl]oxy]-N-[4-(trifluoromethyl)phenyl]-2-benzimidazolamine (also known asRAF265 and CHIR-265), or a pharmaceutically acceptable salt thereof.

Provided is a method of treatment of Acute Myeloid Leukemia in a human in need thereof, wherein the Acute Myeloid Leukemia is characterized by the presence of a BCOR mutation, the method comprising administering to the human a therapeutically effective amount of crizotinib (also known as PF-2341066), or a pharmaceutically acceptable salt thereof.

Provided is a method of treatment of Acute Myeloid Leukemia in a human in need thereof, wherein the Acute Myeloid Leukemia is characterized by the presence of a BCOR mutation, the method comprising administering to the human a therapeutically effective amount of 3,5,7,8-Tetrahydro-2-[4-(trifluoromethyl)phenyl]-4H-thiopyrano[4,3-d]pyrimidin-4-one (also known as XAV-939), or a pharmaceutically acceptable salt thereof.

BCOR-ASXL1-DNMT3A-SRSF2

Provided is a method of treatment of Acute Myeloid Leukemia in a human in need thereof, wherein the Acute Myeloid Leukemia is characterized by the presence of a BCOR mutation and the presence of at least one mutation from the group of an ASXL1 mutation, a DNMT3A mutation and an SRSF2 mutation, the method comprising administering to the human a therapeutically effective amount of 3,5,7,8-Tetrahydro-2-[4-(trifluoromethyl)phenyl]-4H-thiopyrano[4,3-d]pyrimidin-4-one (also known as XAV-939), or a pharmaceutically acceptable salt thereof.

Provided is a method of treatment of Acute Myeloid Leukemia in a human in need thereof, wherein the Acute Myeloid Leukemia is characterized by the presence of a BCOR mutation and an ASXL1 mutation, the method comprising administering to the human a therapeutically effective amount of 3,5,7,8-Tetrahydro-2-[4-(trifluoromethyl)phenyl]-4H-thiopyrano[4,3-d]pyrimidin-4-one (also known as XAV-939), or a pharmaceutically acceptable salt thereof.

Provided is a method of treatment of Acute Myeloid Leukemia in a human in need thereof, wherein the Acute Myeloid Leukemia is characterized by the presence of a BCOR mutation and a DNMT3A mutation, the method comprising administering to the human a therapeutically effective amount of 3,5,7,8-Tetrahydro-2-[4-(trifluoromethyl)phenyl]-4H-thiopyrano[4,3-d]pyrimidin-4-one (also known as XAV-939), or a pharmaceutically acceptable salt thereof.

Provided is a method of treatment of Acute Myeloid Leukemia in a human in need thereof, wherein the Acute Myeloid Leukemia is characterized by the presence of a BCOR mutation and a SRSF2 mutation, the method comprising administering to the human a therapeutically effective amount of 3,5,7,8-Tetrahydro-2-[4-(trifluoromethyl)phenyl]-4H-thiopyrano[4,3-d]pyrimidin-4-one (also known as XAV-939), or a pharmaceutically acceptable salt thereof.

CBFβ-MYH11

Provided is a method of treatment of Acute Myeloid Leukemia in a human in need thereof, wherein the Acute Myeloid Leukemia is characterized by the presence of a CBFβ-MYH11 mutation, the method comprising administering to the human a therapeutically effective amount of one or more agents selected from the group of crenolanib, trametinib, N-(3-(5-chloro-1H-pyrrolo[2,3-b]pyridine-3-carbonyl)-2,4-difluorophenyl)propane-1-sulfonamide (also known as PLX-4720 and CAS No.: 918505-84-7), and Saracatinib, or a pharmaceutically acceptable salt thereof.

Provided is a method of treatment of Acute Myeloid Leukemia in a human in need thereof, wherein the Acute Myeloid Leukemia is characterized by the presence of a CBFB-MYH11 mutation, the method comprising administering to the human a therapeutically effective amount of crenolanib, or a pharmaceutically acceptable salt thereof.

Provided is a method of treatment of Acute Myeloid Leukemia in a human in need thereof, wherein the Acute Myeloid Leukemia is characterized by the presence of a CBFB-MYH11 mutation, the method comprising administering to the human a therapeutically effective amount of trametinib, or a pharmaceutically acceptable salt thereof.

Provided is a method of treatment of Acute Myeloid Leukemia in a human in need thereof, wherein the Acute Myeloid Leukemia is characterized by the presence of a CBFB-MYH11 mutation, the method comprising administering to the human a therapeutically effective amount of N-(3-(5-chloro-1H-pyrrolo[2,3-b]pyridine-3-carbonyl)-2,4-difluorophenyl)propane-1-sulfonamide (also known as PLX-4720 and CAS No.: 918505-84-7), or a pharmaceutically acceptable salt thereof.

Provided is a method of treatment of Acute Myeloid Leukemia in a human in need thereof, wherein the Acute Myeloid Leukemia is characterized by the presence of a CBFB-MYH11 mutation, the method comprising administering to the human a therapeutically effective amount of Saracatinib, or a pharmaceutically acceptable salt thereof.

CBFB-MYH11 and NRAS

Provided is a method of treatment of Acute Myeloid Leukemia in a human in need thereof, wherein the Acute Myeloid Leukemia is characterized by the presence of a CBFB-MYH11 mutation and a NRAS mutation, the method comprising administering to the human a therapeutically effective amount of 1-(2-methoxyethyl)-2-methyl-3-(pyrazin-2-ylmethyl)benzo[f]benzimidazol-3-ium-4,9-dione (also known as YM-155), or a pharmaceutically acceptable salt thereof.

CELSR2

Provided is a method of treatment of Acute Myeloid Leukemia in a human in need thereof, wherein the Acute Myeloid Leukemia is characterized by the presence of a CELSR2 mutation, the method comprising administering to the human a therapeutically effective amount of Tivozanib (also known as AV-951), or a pharmaceutically acceptable salt thereof.

DNMT3A

Provided is a method of treatment of Acute Myeloid Leukemia in a human in need thereof, wherein the Acute Myeloid Leukemia is characterized by the presence of a DNMT3A mutation, the method comprising administering to the human a therapeutically effective amount of one or more agents selected from the group of Lenvatinib, ibrutinib, saracatinib, cabozantinib, sorafenib, and entospletinib, and Dasatinib, or a pharmaceutically acceptable salt thereof.

Provided is a method of treatment of Acute Myeloid Leukemia in a human in need thereof, wherein the Acute Myeloid Leukemia is characterized by the presence of a DNMT3A mutation, the method comprising administering to the human a therapeutically effective amount of Lenvatinib, or a pharmaceutically acceptable salt thereof.

Provided is a method of treatment of Acute Myeloid Leukemia in a human in need thereof, wherein the Acute Myeloid Leukemia is characterized by the presence of a DNMT3A mutation, the method comprising administering to the human a therapeutically effective amount of ibrutinib, or a pharmaceutically acceptable salt thereof.

Provided is a method of treatment of Acute Myeloid Leukemia in a human in need thereof, wherein the Acute Myeloid Leukemia is characterized by the presence of a DNMT3A mutation, the method comprising administering to the human a therapeutically effective amount of saracatinib, or a pharmaceutically acceptable salt thereof.

Provided is a method of treatment of Acute Myeloid Leukemia in a human in need thereof, wherein the Acute Myeloid Leukemia is characterized by the presence of a DNMT3A mutation, the method comprising administering to the human a therapeutically effective amount of cabozantinib, or a pharmaceutically acceptable salt thereof.

Provided is a method of treatment of Acute Myeloid Leukemia in a human in need thereof, wherein the Acute Myeloid Leukemia is characterized by the presence of a DNMT3A mutation, the method comprising administering to the human a therapeutically effective amount of sorafenib, or a pharmaceutically acceptable salt thereof.

Provided is a method of treatment of Acute Myeloid Leukemia in a human in need thereof, wherein the Acute Myeloid Leukemia is characterized by the presence of a DNMT3A mutation, the method comprising administering to the human a therapeutically effective amount of, entospletinib, or a pharmaceutically acceptable salt thereof.

Provided is a method of treatment of Acute Myeloid Leukemia in a human in need thereof, wherein the Acute Myeloid Leukemia is characterized by the presence of a DNMT3A mutation, the method comprising administering to the human a therapeutically effective amount of Dasatinib, or a pharmaceutically acceptable salt thereof.

DNMT3A-IDH2

Provided is a method of treatment of Acute Myeloid Leukemia in a human in need thereof, wherein the Acute Myeloid Leukemia is characterized by the presence of a DNMT3A mutation and an IDH2 mutation, the method comprising administering to the human a therapeutically effective amount of entospletinib, or a pharmaceutically acceptable salt thereof.

FLT3-ITD

Provided is a method of treatment of Acute Myeloid Leukemia in a human in need thereof, wherein the Acute Myeloid Leukemia is characterized by the presence of a FLT3-ITD mutation, the method comprising administering to the human a therapeutically effective amount of at least one agent selected from the group of Barasertib (also known as AZD1152-HQPA), bosutinib, roscovitine, 5-(2,6-Dichlorophenyl)-2-[2,4-difluorophenyl)thio]-6H-pyrimido[1,6-b]pyridazin-6-one (also known as Neflamapimod and VX-745), CYT387, saracatinib, and [(3S,5S,6R,7S,8E,10R,11S,12E,14E)-21-(allylamino)-6-hydroxy-5,11-dimethoxy-3,7,9,15-tetramethyl-16,20,22-trioxo-17-azabicyclo[16.3.1]docosa-8,12,14,18,21-pentaen-10-yl] carbamate (also known as tanespimycin and 17AAG), or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation, the method comprising administering to the human a therapeutically effective amount of Barasertib (also known as AZD1152-HQPA), or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation, the method comprising administering to the human a therapeutically effective amount of tanespimycin (also known as 17AAG), or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation, the method comprising administering to the human a therapeutically effective amount of bosutinib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation, the method comprising administering to the human a therapeutically effective amount of roscovitine, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation, the method comprising administering to the human a therapeutically effective amount of VX-745, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation, the method comprising administering to the human a therapeutically effective amount of CYT387, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation, the method comprising administering to the human a therapeutically effective amount of saracatinib, or a pharmaceutically acceptable salt thereof.

FLT3-ITD and IHD2

Provided is a method of treatment of Acute Myeloid Leukemia in a human in need thereof, wherein the Acute Myeloid Leukemia is characterized by the presence of a FLT3-ITD mutation and an IHD2 mutation, the method comprising administering to the human a therapeutically effective amount of at least one agent selected from the group of Barasertib, ruxolitinib, bosutinib, and tanespimycin (a.k.a. 17AAG), or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an IHD2 mutation, the method comprising administering to the human a therapeutically effective amount of Barasertib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an IHD2 mutation, the method comprising administering to the human a therapeutically effective amount of ruxolitinib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an IHD2 mutation, the method comprising administering to the human a therapeutically effective amount of bosutinib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an IHD2 mutation, the method comprising administering to the human a therapeutically effective amount of tanespimycin (a.k.a. 17AAG or 17-AAG), or a pharmaceutically acceptable salt thereof.

FLT3-ITD and ASXL1

Provided is a method of treatment of Acute Myeloid Leukemia in a human in need thereof, wherein the Acute Myeloid Leukemia is characterized by the presence of a FLT3-ITD mutation and an ASXL1 mutation, the method comprising administering to the human a therapeutically effective amount of at least one agent selected from the group of Barasertib, 17-AAG, and VX-745, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an ASXL1 mutation, the method comprising administering to the human a therapeutically effective amount of Barasertib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an ASXL1 mutation, the method comprising administering to the human a therapeutically effective amount of 17-AAG, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an ASXL1 mutation, the method comprising administering to the human a therapeutically effective amount of VX-745, or a pharmaceutically acceptable salt thereof.

FLT3-ITD and DNMT3A

Provided is a method of treatment of Acute Myeloid Leukemia in a human in need thereof, wherein the Acute Myeloid Leukemia is characterized by the presence of a FLT3-ITD mutation and a DNMT3A mutation, the method comprising administering to the human a therapeutically effective amount of at least one agent selected from the group of Barasertib, 17-AAG, and bosutinib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and a DNMT3A mutation, the method comprising administering to the human a therapeutically effective amount of Barasertib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and a DNMT3A mutation, the method comprising administering to the human a therapeutically effective amount of 17-AAG, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and a DNMT3A mutation, the method comprising administering to the human a therapeutically effective amount of bosutinib, or a pharmaceutically acceptable salt thereof.

FLT3-ITD and IDH1

Provided is a method of treatment of Acute Myeloid Leukemia in a human in need thereof, wherein the Acute Myeloid Leukemia is characterized by the presence of a FLT3-ITD mutation and an IDH1 mutation, the method comprising administering to the human a therapeutically effective amount of at least one agent selected from the group of N-[(1S)-2-[[(7S)-6,7-Dihydro-5-methyl-6-oxo-5H-dibenz[b,d]azepin-7-yl]amino]-1-methyl-2-oxoethyl]-3,5-difluorobenzeneacetamide (DBZ) and venetoclax, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an IDH1 mutation, the method comprising administering to the human a therapeutically effective amount of DBZ, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an IDH1 mutation, the method comprising administering to the human a therapeutically effective amount of venetoclax, or a pharmaceutically acceptable salt thereof.

FLT3-ITD and RUNX1

Provided is a method of treatment of Acute Myeloid Leukemia in a human in need thereof, wherein the Acute Myeloid Leukemia is characterized by the presence of a FLT3-ITD mutation and an RUNX1 mutation, the method comprising administering to the human a therapeutically effective amount of at least one agent selected from the group of bosutinib and 17-AAG, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an RUNX1 mutation, the method comprising administering to the human a therapeutically effective amount of bosutinib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and an RUNX1 mutation, the method comprising administering to the human a therapeutically effective amount of 17-AAG, or a pharmaceutically acceptable salt thereof.

FLT3-ITD and TET2

Provided is a method of treatment of Acute Myeloid Leukemia in a human in need thereof, wherein the Acute Myeloid Leukemia is characterized by the presence of a FLT3-ITD mutation and a TET2 mutation, the method comprising administering to the human a therapeutically effective amount of at least one agent selected from the group of barasertib and bosutinib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and a TET2 mutation, the method comprising administering to the human a therapeutically effective amount of barasertib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and a TET2 mutation, the method comprising administering to the human a therapeutically effective amount of bosutinib, or a pharmaceutically acceptable salt thereof.

FLT3-ITD and WT1

Provided is a method of treatment of Acute Myeloid Leukemia in a human in need thereof, wherein the Acute Myeloid Leukemia is characterized by the presence of a FLT3-ITD mutation and a WT1 mutation, the method comprising administering to the human a therapeutically effective amount of at least one agent selected from the group of barasertib and 17-AAG, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and a WT1 mutation, the method comprising administering to the human a therapeutically effective amount of barasertib, or a pharmaceutically acceptable salt thereof.

Provided is a method of treatment of Acute Myeloid Leukemia in a human in need thereof, wherein the Acute Myeloid Leukemia is characterized by the presence of a FLT3-ITD mutation and a WT1 mutation, the method comprising administering to the human a therapeutically effective amount of 17-AAG, or a pharmaceutically acceptable salt thereof.

IDH1

Provided is a method of treatment of Acute Myeloid Leukemia in a human in need thereof, wherein the Acute Myeloid Leukemia is characterized by the presence of an IDH1 mutation, the method comprising administering to the human a therapeutically effective amount of YM-155, or a pharmaceutically acceptable salt thereof.

IDH2

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of at least one agent selected from the group of crizotinib, GW-2580, Vargetef, Lenvatinib, NVP-TAE684, GSK-1838705A, PHA-665752, DBZ, Foretinib, Masitinib, Entospletinib, and (VX-680), or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of crizotinib, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of GW-2580, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of Vargetef, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of Lenvatinib, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of NVP-TAE684, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of GSK-1838705A, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of PHA-665752, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of DBZ, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of Foretinib, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of Masitinib, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of Entospletinib, or a pharmaceutically acceptable salt thereof.

Provided is a method of treatment of Acute Myeloid Leukemia in a human in need thereof, wherein the Acute Myeloid Leukemia is characterized by the presence of an IDH2 mutation, the method comprising administering to the human a therapeutically effective amount of barasertib, or a pharmaceutically acceptable salt thereof.

MLLT3-KMT2A

Provided is a method of treatment of Acute Myeloid Leukemia in a human in need thereof, wherein the Acute Myeloid Leukemia is characterized by the presence of a MLLT3-KMT2A mutation, the method comprising administering to the human a therapeutically effective amount of vatalanib (PTK787), or a pharmaceutically acceptable salt thereof.

MYC

Provided is a method of treatment of Acute Myeloid Leukemia in a human in need thereof, wherein the Acute Myeloid Leukemia is characterized by the presence of a MYC mutation, the method comprising administering to the human a therapeutically effective amount of saracatinib, or a pharmaceutically acceptable salt thereof.

NPM1

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of at least one agent selected from the group of KW-2449, ibrutinib, vandetanib, lenvatinib, sorafenib, regorafenib, cabozantinib, DBZ, entospletinib, foretinib, sunitinib, dovitinib, quizartinib, ponatinib, barasertib, erlotinib, crenolanib, 17-AAG, Gefitinib, NVP-TAE684, and Vargetef, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of KW-2449, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of ibrutinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of vandetanib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of lenvatinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of sorafenib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of regorafenib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of cabozantinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of DBZ, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of entospletinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of foretinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of sunitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of dovitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of quizartinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of ponatinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of barasertib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of erlotinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of crenolanib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of 17-AAG, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of Gefitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of NVP-TAE684, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, the method comprising administering to the human a therapeutically effective amount of Vargetef, or a pharmaceutically acceptable salt thereof.

NPM1 and CEBPA

Provided is a method of treatment of Acute Myeloid Leukemia in a human in need thereof, wherein the Acute Myeloid Leukemia is characterized by the presence of a NPM1 mutation and a CEBPA mutation, the method comprising administering to the human a therapeutically effective amount of at least one agent selected from the group of [4-[2-(1H-Indazol-3-yl)ethenyl]phenyl]-1-piperazinyl-methanone (KW-2449), 6-((6-(1-methyl-1H-pyrazol-4-yl)-[1,2,4]triazolo[4,3-b]pyridazin-3-yl)thio)quinoline (SGX-523), and crizotinib, or a pharmaceutically acceptable salt thereof.

Provided is a method of treatment of Acute Myeloid Leukemia in a human in need thereof, wherein the Acute Myeloid Leukemia is characterized by the presence of a NPM1 mutation and a CEBPA mutation, the method comprising administering to the human a therapeutically effective amount of [4-[2-(1H-Indazol-3-yl)ethenyl]phenyl]-1-piperazinylmethanone (KW-2449), or a pharmaceutically acceptable salt thereof.

Provided is a method of treatment of Acute Myeloid Leukemia in a human in need thereof, wherein the Acute Myeloid Leukemia is characterized by the presence of a NPM1 mutation and a CEBPA mutation, the method comprising administering to the human a therapeutically effective amount of 6-((6-(1-methyl-1H-pyrazol-4-yl)-[1,2,4]triazolo[4,3-b]pyridazin-3-yl)thio)quinoline (SGX-523), or a pharmaceutically acceptable salt thereof.

Provided is a method of treatment of Acute Myeloid Leukemia in a human in need thereof, wherein the Acute Myeloid Leukemia is characterized by the presence of a NPM1 mutation and a CEBPA mutation, the method comprising administering to the human a therapeutically effective amount of crizotinib, or a pharmaceutically acceptable salt thereof.

NPM1 and DNMT3A

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of at least one agent selected from the group of lenvatinib, ibrutinib, saracatinib, regorafenib, foretinib, cabozantinib, sorafenib, KW-2449, PRT062607, entospletinib, crenolanib, gefitinib, dovitinib, 17-AAG, axitinib, gilteritinib, quizartinib, sunitinib, ponatinib, and 4-((5-amino-1-(2,6-difluorobenzoyl)-1H-1,2,4-triazol-3-yl) amino)benzenesulfonamide (JNJ-7706621), or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of lenvatinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of ibrutinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of saracatinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of regorafenib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of foretinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of cabozantinib or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of sorafenib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of KW-2449, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of PRT062607, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of entospletinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of crenolanib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of gefitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of dovitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of 17-AAG, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of axitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of gilteritinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of quizartinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of sunitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of ponatinib or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a DNMT3A mutation, the method comprising administering to the human a therapeutically effective amount of JNJ-7706621, or a pharmaceutically acceptable salt thereof.

NPM1 and FLT3-ITD

Provided is a method of treatment of Acute Myeloid Leukemia in a human in need thereof, wherein the Acute Myeloid Leukemia is characterized by the presence of an NPM1 mutation and a FLT3-ITD mutation, the method comprising administering to the human a therapeutically effective amount of at least one agent selected from the group of barasertib, 17-AAG, cyt387, and bosutinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a FLT3-ITD mutation, the method comprising administering to the human a therapeutically effective amount of barasertib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a FLT3-ITD mutation, the method comprising administering to the human a therapeutically effective amount of 17-AAG, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a FLT3-ITD mutation, the method comprising administering to the human a therapeutically effective amount of cyt387, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a FLT3-ITD mutation, the method comprising administering to the human a therapeutically effective amount of bosutinib, or a pharmaceutically acceptable salt thereof.

NPM1 and FLT3-ITD and DNMT3A

Provided is a method of treatment of Acute Myeloid Leukemia in a human in need thereof, wherein the Acute Myeloid Leukemia is characterized by the presence of an NPM1 mutation, a FLT3-ITD mutation, and a DNMT3A mutation, the method comprising administering to the human a therapeutically effective amount of at least one agent selected from the group of 17-AAG, saracatinib, and bosutinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a FLT3-ITD mutation, and a DNMT3A mutation, the method comprising administering to the human a therapeutically effective amount of 17-AAG, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a FLT3-ITD mutation, and a DNMT3A mutation, the method comprising administering to the human a therapeutically effective amount of saracatinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a FLT3-ITD mutation, and a DNMT3A mutation, the method comprising administering to the human a therapeutically effective amount of bosutinib, or a pharmaceutically acceptable salt thereof.

NPM1 and FLT3-ITD and TET2

Provided is a method of treatment of Acute Myeloid Leukemia in a human in need thereof, wherein the Acute Myeloid Leukemia is characterized by the presence of an NPM1 mutation, a FLT3-ITD mutation, and a TET2 mutation, the method comprising administering to the human a therapeutically effective amount of at least one agent selected from the group of 17-AAG, and barasertib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a FLT3-ITD mutation, and a TET2 mutation, the method comprising administering to the human a therapeutically effective amount of 17-AAG, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a FLT3-ITD mutation, and a TET2 mutation, the method comprising administering to the human a therapeutically effective amount of barasertib, or a pharmaceutically acceptable salt thereof.

NPM1 and IDH1

Provided is a method of treatment of Acute Myeloid Leukemia in a human in need thereof, wherein the Acute Myeloid Leukemia is characterized by the presence of an NPM1 mutation and an IDH1 mutation, the method comprising administering to the human a therapeutically effective amount of at least one agent selected from the group of barasertib, JNJ-7706621, dovitinib, ym-155 (Sepantronium bromide), erlotinib, roscovitine, and entospletinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH1 mutation, the method comprising administering to the human a therapeutically effective amount of barasertib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH1 mutation, the method comprising administering to the human a therapeutically effective amount of JNJ-7706621, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH1 mutation, the method comprising administering to the human a therapeutically effective amount of dovitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH1 mutation, the method comprising administering to the human a therapeutically effective amount of ym-155 (Sepantronium bromide), or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH1 mutation, the method comprising administering to the human a therapeutically effective amount of erlotinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH1 mutation, the method comprising administering to the human a therapeutically effective amount of roscovitine, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH1 mutation, the method comprising administering to the human a therapeutically effective amount of entospletinib, or a pharmaceutically acceptable salt thereof.

NPM1 and IDH2

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of at least one agent selected from the group of DBZ, KW-2449, MLN120B, vandetanib, NVP-TAE684, vargetef, NF-kB activation inhibitor, GSK-1838705A, SGX-523, GW-2580, ibrutinib, barasertib, ponatinib, lapatinib, gefitinib, gilteritinib, ruxolitinib, palbociclib, sorafenib, erlotinib, VX-745, cabozantinib, entospletinib (GS-9973), quizartinib, lenvatinib, regorafenib, and vemurafenib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of DBZ, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of KW-2449, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of MLN120B, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of vandetanib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of NVP-TAE684, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of vargetef, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of NF-kB activation inhibitor, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of GSK-1838705A, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of SGX-523, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of GW-2580, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of ibrutinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of barasertib or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of ponatinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of lapatinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of gefitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of gilteritinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of ruxolitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of palbociclib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of sorafenib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of erlotinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of VX-745, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of cabozantinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of entospletinib (GS-9973), or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of quizartinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of lenvatinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of regorafenib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an IDH2 mutation, the method comprising administering to the human a therapeutically effective amount of vemurafenib, or a pharmaceutically acceptable salt thereof.

NPM1 and SRSF2

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of at least one agent selected from the group of KW-2449, vandetanib, NVP-TAE684, MLN120B, foretinib, sunitinib, Vargetef, barasertib, SGX-523, sorafenib, cabozantinib, entospletinib, NFkB-activation inhibitor, and regorafenib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of KW-2449, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of vandetanib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of NVP-TAE684, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of foretinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of sunitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of Vargetef, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of barasertib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of SGX-523, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of sorafenib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of cabozantinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of entospletinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and an SRSF2 mutation, the method comprising administering to the human a therapeutically effective amount of regorafenib, or a pharmaceutically acceptable salt thereof.

NPM1 and SRSF2 and IDH2

Provided is a method of treatment of Acute Myeloid Leukemia in a human in need thereof, wherein the Acute Myeloid Leukemia is characterized by the presence of an NPM1 mutation, a SRSF2 mutation, and an IDH2 mutation, the method comprising administering to the human a therapeutically effective amount of at least one agent selected from the group of ibrutinib, KW-2449, SGX-523, AZD1480, NVP-TAE684, K120227, and DBZ, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a SRSF2 mutation, and an IDH2 mutation, the method comprising administering to the human a therapeutically effective amount of ibrutinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a SRSF2 mutation, and an IDH2 mutation, the method comprising administering to the human a therapeutically effective amount of KW-2449, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a SRSF2 mutation, and an IDH2 mutation, the method comprising administering to the human a therapeutically effective amount of SGX-523, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a SRSF2 mutation, and an IDH2 mutation, the method comprising administering to the human a therapeutically effective amount of AZD1480, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a SRSF2 mutation, and an IDH2 mutation, the method comprising administering to the human a therapeutically effective amount of NVP-TAE684, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a SRSF2 mutation, and an IDH2 mutation, the method comprising administering to the human a therapeutically effective amount of K120227, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a SRSF2 mutation, and an IDH2 mutation, the method comprising administering to the human a therapeutically effective amount of DBZ, or a pharmaceutically acceptable salt thereof.

NPM1 and TET2

Provided is a method of treatment of Acute Myeloid Leukemia in a human in need thereof, wherein the Acute Myeloid Leukemia is characterized by the presence of an NPM1 mutation and a TET2 mutation, the method comprising administering to the human a therapeutically effective amount of at least one agent selected from the group of sorafenib and sunitinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a TET2 mutation, the method comprising administering to the human a therapeutically effective amount of sorafenib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation and a TET2 mutation, the method comprising administering to the human a therapeutically effective amount of sunitinib, or a pharmaceutically acceptable salt thereof.

NPM1 and TET2 and DNMT3A

Provided is a method of treatment of Acute Myeloid Leukemia in a human in need thereof, wherein the Acute Myeloid Leukemia is characterized by the presence of an NPM1 mutation, a TET2 mutation, and a DNMT3A mutation, the method comprising administering to the human a therapeutically effective amount of at least one agent selected from the group of regorafenib (BAY 73-4506), cabozantinib, lenvatinib, vargetef, and entospletinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a TET2 mutation, and a DNMT3A mutation, the method comprising administering to the human a therapeutically effective amount of regorafenib (BAY 73-4506), or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a TET2 mutation, and a DNMT3A mutation, the method comprising administering to the human a therapeutically effective amount of cabozantinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a TET2 mutation, and a DNMT3A mutation, the method comprising administering to the human a therapeutically effective amount of lenvatinib, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a TET2 mutation, and a DNMT3A mutation, the method comprising administering to the human a therapeutically effective amount of vargetef, or a pharmaceutically acceptable salt thereof.

Provided is a method of treatment of Acute Myeloid Leukemia in a human in need thereof, wherein the Acute Myeloid Leukemia is characterized by the presence of an NPM1 mutation, a TET2 mutation, and a DNMT3A mutation, the method comprising administering to the human a therapeutically effective amount of entospletinib, or a pharmaceutically acceptable salt thereof.

NRAS

Provided is a method of treatment of Acute Myeloid Leukemia in a human in need thereof, wherein the Acute Myeloid Leukemia is characterized by the presence of a NRAS mutation, the method comprising administering to the human a therapeutically effective amount of Flavopiridol, or a pharmaceutically acceptable salt thereof.

PDS5B

Provided is a method of treatment of Acute Myeloid Leukemia in a human in need thereof, wherein the Acute Myeloid Leukemia is characterized by the presence of a PDS5B mutation, the method comprising administering to the human a therapeutically effective amount of N'-(1,8-dimethyl-4-imidazo[1,2-a]quinoxalinyl)ethane-1,2-diamine (BMS-345541), or a pharmaceutically acceptable salt thereof.

PML-RARA

Provided is a method of treatment of Acute Myeloid Leukemia in a human in need thereof, wherein the Acute Myeloid Leukemia is characterized by the presence of a PML-RARA mutation, the method comprising administering to the human a therapeutically effective amount of at least one agent selected from the group of venetoclax, and YM-155, or a pharmaceutically acceptable salt thereof.

Provided is a method of treatment of Acute Myeloid Leukemia in a human in need thereof, wherein the Acute Myeloid Leukemia is characterized by the presence of a PML-RARA mutation, the method comprising administering to the human a therapeutically effective amount of venetoclax, or a pharmaceutically acceptable salt thereof.

Provided is a method of treatment of Acute Myeloid Leukemia in a human in need thereof, wherein the Acute Myeloid Leukemia is characterized by the presence of a PML-RARA mutation, the method comprising administering to the human a therapeutically effective amount of YM-155, or a pharmaceutically acceptable salt thereof.

RUNX1

Provided is a method of treatment of Acute Myeloid Leukemia in a human in need thereof, wherein the Acute Myeloid Leukemia is characterized by the presence of a RUNX1 mutation, the method comprising administering to the human a therapeutically effective amount of at least one agent selected from the group of cediranib and BEZ2345, or a pharmaceutically acceptable salt thereof.

Provided is a method of treatment of Acute Myeloid Leukemia in a human in need thereof, wherein the Acute Myeloid Leukemia is characterized by the presence of a RUNX1 mutation, the method comprising administering to the human a therapeutically effective amount of cediranib, or a pharmaceutically acceptable salt thereof.

Provided is a method of treatment of Acute Myeloid Leukemia in a human in need thereof, wherein the Acute Myeloid Leukemia is characterized by the presence of a RUNX1 mutation, the method comprising administering to the human a therapeutically effective amount of BEZ2345, or a pharmaceutically acceptable salt thereof.

RUNX1 and DNMT3A

Provided is a method of treatment of Acute Myeloid Leukemia in a human in need thereof, wherein the Acute Myeloid Leukemia is characterized by the presence of a RUNX1 mutation and a DNMT3A mutation, the method comprising administering to the human a therapeutically effective amount of MGCD-265, or a pharmaceutically acceptable salt thereof.

SMC1A

Provided is a method of treatment of Acute Myeloid Leukemia in a human in need thereof, wherein the Acute Myeloid Leukemia is characterized by the presence of a SMC1A mutation, the method comprising administering to the human a therapeutically effective amount of at least one agent selected from the group of GDC-0879, vatalanib, GSK-1838705A, BAY 11-7085, masitinib, lapatinib, canertinib, foretinib, and crizotinib, or a pharmaceutically acceptable salt thereof.

Provided is a method of treatment of Acute Myeloid Leukemia in a human in need thereof, wherein the Acute Myeloid Leukemia is characterized by the presence of a SMC1A mutation, the method comprising administering to the human a therapeutically effective amount of GDC-0879, or a pharmaceutically acceptable salt thereof.

Provided is a method of treatment of Acute Myeloid Leukemia in a human in need thereof, wherein the Acute Myeloid Leukemia is characterized by the presence of a SMC1A mutation, the method comprising administering to the human a therapeutically effective amount of vatalanib, or a pharmaceutically acceptable salt thereof.

Provided is a method of treatment of Acute Myeloid Leukemia in a human in need thereof, wherein the Acute Myeloid Leukemia is characterized by the presence of a SMC1A mutation, the method comprising administering to the human a therapeutically effective amount GSK-1838705A, or a pharmaceutically acceptable salt thereof.

Provided is a method of treatment of Acute Myeloid Leukemia in a human in need thereof, wherein the Acute Myeloid Leukemia is characterized by the presence of a SMC1A mutation, the method comprising administering to the human a therapeutically effective amount of BAY 11-7085, or a pharmaceutically acceptable salt thereof.

Provided is a method of treatment of Acute Myeloid Leukemia in a human in need thereof, wherein the Acute Myeloid Leukemia is characterized by the presence of a SMC1A mutation, the method comprising administering to the human a therapeutically effective amount of masitinib, or a pharmaceutically acceptable salt thereof.

Provided is a method of treatment of Acute Myeloid Leukemia in a human in need thereof, wherein the Acute Myeloid Leukemia is characterized by the presence of a SMC1A mutation, the method comprising administering to the human a therapeutically effective amount of lapatinib, or a pharmaceutically acceptable salt thereof.

Provided is a method of treatment of Acute Myeloid Leukemia in a human in need thereof, wherein the Acute Myeloid Leukemia is characterized by the presence of a SMC1A mutation, the method comprising administering to the human a therapeutically effective amount of canertinib, or a pharmaceutically acceptable salt thereof.

Provided is a method of treatment of Acute Myeloid Leukemia in a human in need thereof, wherein the Acute Myeloid Leukemia is characterized by the presence of a SMC1A mutation, the method comprising administering to the human a therapeutically effective amount of foretinib, or a pharmaceutically acceptable salt thereof.

Provided is a method of treatment of Acute Myeloid Leukemia in a human in need thereof, wherein the Acute Myeloid Leukemia is characterized by the presence of a SMC1A mutation, the method comprising administering to the human a therapeutically effective amount of crizotinib, or a pharmaceutically acceptable salt thereof.

TRIO

Provided is a method of treatment of Acute Myeloid Leukemia in a human in need thereof, wherein the Acute Myeloid Leukemia is characterized by the presence of a TRIO mutation, the method comprising administering to the human a therapeutically effective amount of palbociclib, or a pharmaceutically acceptable salt thereof.

U2AF1

Provided is a method of treatment of Acute Myeloid Leukemia in a human in need thereof, wherein the Acute Myeloid Leukemia is characterized by the presence of a U2AF1 mutation, the method comprising administering to the human a therapeutically effective amount of cediranib (AZD2171), or a pharmaceutically acceptable salt thereof.

WT1

Provided is a method of treatment of Acute Myeloid Leukemia in a human in need thereof, wherein the Acute Myeloid Leukemia is characterized by the presence of a WT1 mutation, the method comprising administering to the human a therapeutically effective amount of RAF265 (also known as CHIR-265), or a pharmaceutically acceptable salt thereof.

Uses in the Preparation of Medicaments

Also provided is the use of entospletinib (GS-9973), or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation and an IDH2 mutation; b) an NPM1 mutation and an SRSF2 mutation; c) an NPM1 mutation, a TET2 mutation, and a DNMT3A mutation; d) a DNMT3A mutation; e) a DNMT3A mutation and an IDH2 mutation; f) an IDH2 mutation; g) an NPM1 mutation; h) an NPM1 mutation and a DNMT3A mutation; and i) an NPM1 mutation and an IDH1 mutation.

Also provided is the use of sunitinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation; an NPM1 mutation and a DNMT3A mutation; c) an NPM1 mutation and an SRSF2 mutation; and d) an NPM1 mutation and a TET2 mutation.

Also provided is the use of cabozantinib, or a pharmaceutically acceptable salt thereof, in the preparation of a medicament for the treatment of Acute Myeloid Leukemia in a human, wherein the Acute Myeloid Leukemia is characterized by a DNMT3A mutation.

Also provided is the use of sorafenib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a DNMT3A mutation; b) an NPM1 mutation; c) an NPM1 mutation and a DNMT3A mutation; d) an NPM1 mutation and an IDH2 mutation; e) an NPM1 mutation and an SRSF2 mutation; f) and an NPM1 mutation and a TET2 mutation.

Also provided is the use of crizotinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a BCOR mutation; b) an IDH2 mutation; c) a NPM1 mutation and a CEBPA mutation; and d) a SMC1A mutation.

Also provided is the use of Tivozanib, or a pharmaceutically acceptable salt thereof, in the preparation of a medicament for the treatment of Acute Myeloid Leukemia in a human, wherein the Acute Myeloid Leukemia is characterized by a CELSR2 mutation.

Also provided is the use of crenolanib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a CBFB-MYH11 mutation; b) an NPM1 mutation; and c) an NPM1 mutation and a DNMT3A mutation.

Also provided is the use of ibrutinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) DNMT3A mutation; b) an NPM1 mutation; c) an NPM1 mutation and a DNMT3A mutation; d) an NPM1 mutation and an IDH2 mutation; and e) an NPM1 mutation, a SRSF2 mutation, and an IDH2 mutation.

Also provided is the use of trametinib, or a pharmaceutically acceptable salt thereof, in the preparation of a medicament for the treatment of Acute Myeloid Leukemia in a human, wherein the Acute Myeloid Leukemia is characterized by a CBFB-MYH11 mutation.

Also provided is the use of lenvatinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a DNMT3A mutation; b) an IDH2 mutation; c) an NPM1 mutation; d) an NPM1 mutation and a DNMT3A mutation; e) an NPM1 mutation and an IDH2 mutation; and f) an NPM1 mutation, a TET2 mutation, and a DNMT3A mutation.

Also provided is the use of saracatinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a CBFB-MYH11 mutation; b) a DNMT3A mutation; c) a FLT3-ITD mutation; d) a Myc mutation; e) an NPM1 mutation and a DNMT3A mutation; and f) an NPM1 mutation, a FLT3-ITD mutation, and a DNMT3A mutation.

Also provided is the use of dasatinib, or a pharmaceutically acceptable salt thereof, in the preparation of a medicament for the treatment of Acute Myeloid Leukemia in a human, wherein the Acute Myeloid Leukemia is characterized by a DNMT3A mutation.

Also provided is the use of bosutinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a FLT3-ITD mutation; b) a FLT3-ITD mutation and an IHD2 mutation; c) a FLT3-ITD mutation and a DNMT3A mutation; d) a FLT3-ITD mutation and a TET2 mutation; e) an NPM1 mutation and a FLT3-ITD mutation; and f) an NPM1 mutation, a FLT3-ITD mutation, and a DNMT3A mutation.

Also provided is the use of roscovitine, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a FLT3-ITD mutation; and b) an NPM1 mutation and an IDH1 mutation.

Also provided is the use of ruxolitinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a FLT3-ITD mutation and an IHD2 mutation; and b) an NPM1 mutation and an IDH2 mutation.

Also provided is the use of Vargetef, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an IDH2 mutation; b) an NPM1 mutation and an IDH2 mutation; c) an NPM1 mutation and an SRSF2 mutation; and d) an NPM1 mutation, a TET2 mutation, and a DNMT3A mutation.

Also provided is the use of foretinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an IDH2 mutation; b) an NPM1 mutation; c) an NPM1 mutation and a DNMT3A mutation; d) an NPM1 mutation and an SRSF2 mutation; and e) a SMC1A mutation.

Also provided is the use of Masitinib, or a pharmaceutically acceptable salt thereof, in the preparation of a medicament for the treatment of Acute Myeloid Leukemia in a human, wherein the Acute Myeloid Leukemia is characterized by at least one mutation selected from the group of: a) an IDH2 mutation and b) a SMC1A mutation.

Also provided is the use of dovitinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation; b) an NPM1 mutation and a DNMT3A mutation; and c) an NPM1 mutation and an IDH1 mutation.

Also provided is the use of regorafenib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation; b) an NPM1 mutation and a DNMT3A mutation; c) an NPM1 mutation and an IDH2 mutation; d) an NPM1 mutation and an SRSF2 mutation; and e) an NPM1 mutation, a TET2 mutation, and a DNMT3A mutation.

Also provided is the use of barasertib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a FLT3-ITD mutation; b) a FLT3-ITD mutation and an IHD2 mutation; c) a FLT3-ITD mutation and an ASXL1 mutation; d) a FLT3-ITD mutation and a DNMT3A mutation; e) a FLT3-ITD mutation and a TET2 mutation; f) a FLT3-ITD mutation and a WT1 mutation; g) an IDH2 mutation; h) an NPM1 mutation; i) an NPM1 mutation and a FLT3-ITD mutation; j) an NPM1 mutation, a FLT3-ITD mutation, and a TET2 mutation; k) an NPM1 mutation and an IDH1 mutation; an NPM1 mutation and an IDH2 mutation; and l) an NPM1 mutation and an SRSF2 mutation.

Also provided is the use of gefitinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation; b) an NPM1 mutation and a DNMT3A mutation; and c) an NPM1 mutation and an IDH2 mutation.

Also provided is the use of gilteritinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation and a DNMT3A mutation; and b) an NPM1 mutation and an IDH2 mutation.

Also provided is the use of quizartinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation; b) an NPM1 mutation and a DNMT3A mutation; and c) an NPM1 mutation and an IDH2 mutation.

Also provided is the use of ponatinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation; b) an NPM1 mutation and a DNMT3A mutation; and c) an NPM1 mutation and an IDH2 mutation.

Also provided is the use of vemurafenib, or a pharmaceutically acceptable salt thereof, in the preparation of a medicament for the treatment of Acute Myeloid Leukemia in a human, wherein the Acute Myeloid Leukemia is characterized by an NPM1 mutation and an IDH2 mutation.

Also provided is the use of DBZ, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a FLT3-ITD mutation and an IDH1 mutation; b) an IDH2 mutation; c) an NPM1 mutation; d) an NPM1 mutation and an IDH2 mutation; and e) an NPM1 mutation, a SRSF2 mutation, and an IDH2 mutation.

Also provided is the use of palbociclib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation and an IDH2 mutation; and b) a TRIO mutation.

Also provided is the use of erlotinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation; b) an NPM1 mutation and an IDH1 mutation; and c) an NPM1 mutation and an IDH2 mutation.

Also provided is the use of lapatinib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation and an IDH2 mutation; and b) a SMC1A mutation.

Also provided is the use of venetoclax, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a FLT3-ITD mutation and an IDH1 mutation; and b) a PML-RARA mutation.

Also provided is the use of vandetanib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) an NPM1 mutation; b) an NPM1 mutation and an IDH2 mutation; and c) an NPM1 mutation and an SRSF2 mutation.

Also provided is the use of vatalanib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a MLLT3-KMT2A mutation; and b) a SMC1A mutation.

Also provided is the use of canertinib, or a pharmaceutically acceptable salt thereof, in the preparation of a medicament for the treatment of Acute Myeloid Leukemia in a human, wherein the Acute Myeloid Leukemia is characterized by a SMC1A mutation.

Also provided is the use of cediranib, or a pharmaceutically acceptable salt thereof, in the preparation of a medicament for the treatment of Acute Myeloid Leukemia in a human, wherein the Acute Myeloid Leukemia is characterized by at least one mutation or combination of mutations selected from the group of: a) a RUNX1 mutation; and b) a U2AF1 mutation.

Terms

"Acute myeloid leukemia (AML)" refers to a rapidly progressing cancer of the blood and bone marrow that affects a group of white blood cells called the myeloid cells. AML can also be referred to as acute myelogenous leukemia, acute myeloblastic leukemia, acute granulocytic leukemia and acute nonlymphocytic leukemia.

"Binding": an association between two substances or molecules such as the association of an antibody with a cell surface marker. As described herein, stable binding (or detectable binding) means that a macromolecule such as an antibody can bind to another macromolecule such as a polypeptide in a manner that can be detected. Binding can be detected by any procedure known to one skilled in the art, such as by physical or functional properties. Binding can also be detected by visualization of a label (such as a fluorescent label) conjugated to one of the molecules. Specific binding means that a macromolecule such as an antibody binds to members of a class of macromolecules to the exclusion of macromolecules not in that class (binding to non-specific antibody binding macromolecules such as protein A, Fc receptors, etc. is excepted).

"Biomarker (marker)": Molecular, biological or physical attributes that characterize a physiological, cellular, or disease state and that can be objectively measured to detect or define disease progression or predict or quantify therapeutic responses. A biomarker is a characteristic that is objectively measured and evaluated as an indicator of normal biologic processes, pathogenic processes, or pharmacologic responses to a therapeutic intervention. A biomarker may be any molecular structure produced by a cell or organism. A biomarker may be expressed inside any cell or tissue; accessible on the surface of a tissue or cell; structurally inherent to a cell or tissue such as a structural component, secreted by a cell or tissue, produced by the breakdown of a cell or tissue through processes such as necrosis, apoptosis or the like; or any combination of these. A biomarker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A biomarker can also be a discrete cellular entity such as a circulating leukemia cell expressing particular cell surface markers including CD11b or CD58.

"Chronic lymphocytic leukemia (CLL)": a slower progressing cancer of the blood and bone marrow that affects lymphocytes.

"Contacting": Placing within an environment where direct physical association occurs, including contacting of a solid with a solid, a liquid with a liquid, a liquid with a solid, or either a liquid or a solid with a cell or tissue, whether in vitro or in vivo. Contacting can occur in vitro with isolated cells or tissue or in vivo by administering to a subject.

"Effective Amoun"t: An "effective amount", a "therapeutically effective amount", and/or a "pharmaceutically effective amount" of an agent is an amount that upon administration to a human in need thereof is sufficient to generate a desired response such as reducing or eliminating a sign or symptom of a condition or a disease. An effective amount also encompasses an effective amount of a first agent and an effective amount of a second agent administered in combination with the first agent. In some examples, the effective amount of the two combined agents is less than that of either agent when administered alone.

"Hematological malignancy": a general term for cancers that affects the blood or bone marrow.

"Label": A label can be any substance capable of aiding a machine, detector, sensor, device, column, or enhanced or unenhanced human eye from differentiating a labeled composition from an unlabeled composition. Labels may be used for any of a number of purposes and one skilled in the art will understand how to match the proper label with the proper purpose. Examples of uses of labels include purification of biomolecules, identification of biomolecules, detection of the presence of biomolecules, detection of protein folding, and localization of biomolecules within a cell, tissue, or organism. Examples of labels include: radioactive isotopes or chelates thereof; dyes (fluorescent or nonfluorescent), stains, enzymes, nonradioactive metals, magnets, protein tags, fluorescent proteins, any antibody epitope, any specific example of any of these; any combination between any of these, or any label now known or yet to be disclosed. A label may be covalently attached to a biomolecule or bound through hydrogen bonding, Van Der Waals or other forces. A label may be covalently or otherwise bound to the N-terminus, the C-terminus or any amino acid of a polypeptide or the 5' end, the 3' end or any nucleic acid residue in the case of a polynucleotide.

"Myeloproliferative neoplasms or myelodysplastic syndromes (MPN or MDS/MPN)": blood cancers that are characterized by the overproduction of white blood cells, red blood cell, or platelets. Examples of MPNs include polycythemia vera, essential thrombocythemia, and myelofibrosis.

"Myelodysplastic Syndrome (MDS)" refers to conditions in which blood-forming cells in bone marrow become abnormal or dysplastic, leading to lower numbers of one or more types of blood cells. References herein are understood to include the conditions of MDS with multilineage dysplasia, MDS with single lineage dysplasia (including refractory anemia (RA), refractory neutropenia (RN), and refractory thrombocytopenia (RT)), MDS with ring sideroblasts, MDS with excess blasts (including MDS-EB1 and MDS-EB2), MDS with isolated del(5q), and MDS, unclassified (MDS-U). The methods herein also encompass treatments for the conditions above as primary MDS (cause unknown) and secondary MDS (cause known).

"Subject" or "patient": A living multicellular vertebrate organism, a category that includes, for example, mammals and birds. A "mammal" includes both human and non-human mammals, such as mice. In some examples, a subject is a human patient, such as a patient diagnosed with AML, a myeloproliferative neoplasm, or myelodysplastic syndromes. In other examples, a subject is a human patient yet to be diagnosed with AML, a myeloproliferative neoplasm, or myelodysplastic syndromes.

"Treatment": any therapeutic intervention that ameliorates a sign or symptom of a disease or pathological condition. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other clinical or physiological parameters associated with a particular disease. A "prophylactic" treatment is a treatment administered to a subject who does not exhibit signs of a disease or exhibits only early signs for the purpose of decreasing the risk of developing pathology. A "therapeutic" treatment is a treatment administered after the development of significant signs or symptoms of the disease. The terms "for treatment of", "for use in the treatment of", "for treating", "for use in treating" and the like are understood to be synonymous and may be interchanged in describing and claiming the methods herein.

"Pharmaceutically acceptable salts" include, for example, salts with inorganic acids and salts with an organic acid. Examples of salts may include hydrochloride, phosphate, diphosphate, hydrobromide, sulfate, sulfinate, nitrate, malate, maleate, fumarate, tartrate, succinate, citrate, acetate, lactate, methanesulfonate (mesylate), benzenesufonate (besylate), p-toluenesulfonate (tosylate), 2-hydroxyethylsulfonate, benzoate, salicylate, stearate, and alkanoate (such as acetate, HOOC--(CH$_2$)$_n$--COOH where n is 0-4). In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

Pharmaceutical Compositions

The compounds disclosed herein may be included in pharmaceutical compositions (including therapeutic and prophylactic formulations), typically combined together with one or more pharmaceutically acceptable carriers (known equivalently as vehicles) and, optionally, other therapeutic ingredients.

Such pharmaceutical compositions can formulated for administration to subjects by a variety of mucosal administration modes, including by oral, rectal, intranasal, intrapulmonary, intravitrial, or transdermal delivery, or by topical delivery to other surfaces including the eye. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other examples, the compound can be administered ex vivo by direct exposure to cells, tissues or organs originating from a subject.

To formulate the pharmaceutical compositions, the compound can be combined with various pharmaceutically acceptable additives. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween®-80), solubility enhancing agents (for example, cyclodextrins and derivatives thereof), stabilizers (for example, serum albumin), and reducing agents (for example, glutathione) can be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7. The compound can be dispersed in any pharmaceutically acceptable carrier, which can include a hydrophilic compound having a capacity to disperse the compound, and any desired additives. The carrier can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a carrier, for example, polylactic acid, poly(lactic acid-glycolic acid) copolymer, polyhydroxybutyric acid, poly(hydroxybutyric acidglycolic acid) copolymer and mixtures thereof.

Alternatively or additionally, synthetic fatty acid esters such as polyglycerin fatty acid esters, sucrose fatty acid esters and the like can be employed as carriers. Hydrophilic polymers and other vehicles can be used alone or in combination, and enhanced structural integrity can be imparted to the vehicle by partial crystallization, ionic bonding, cross-linking and the like. The carrier can be provided in a variety of forms, including fluid or viscous solutions, gels, pastes, powders, microspheres, and films for direct application to a mucosal surface.

The compound can be combined with the carrier according to a variety of methods, and release of the compound can be by diffusion, disintegration of the vehicle, or associated formation of water channels. In some circumstances, the compound is dispersed in microcapsules (microspheres) or nanoparticles prepared from a suitable polymer, for example,
5-isobutyl 2-cyanoacrylate (see, for example, Michael et al., *J. Pharmacy Pharmacol.* 43, 1-5, (1991)), and dispersed in a biocompatible dispersing medium, which yields sustained delivery and biological activity over a protracted time.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acidco-glycolic acid), poly(D-lactic acid-coglycolic acid), and poly(L-lactic acid-coglycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(betahydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Treatment

Disclosed are methods of treating a subject with a hematological malignancy using combinations of compositions described herein. The compounds can be administered by any appropriate route including orally or parenterally including buccally, sublingually, sublabially, by inhalation, intra-arterially, intravenously, intraventricularly, intramuscularly, subcutaneously, intraspinally, intraorbitally, intracranially or intrathecally.

The administration of a pharmaceutical composition comprising the disclosed compounds can be for prophylactic or therapeutic purposes. For prophylactic and therapeutic purposes, the treatments can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the treatments for viral infection can be provided as repeated doses within a prolonged prophylaxis or treatment regimen that will yield clinically significant results to alleviate one or more symptoms or detectable conditions associated with a disease or condition.

An effective amount or concentration of the disclosed combinations of compounds can be any amount of the two compounds administered by themselves alone or in combination with additional therapeutic agents, is sufficient to achieve a desired effect in a subject. The effective amount of the agent will be dependent on several factors, including, but not limited to, the subject being treated and the manner of administration of the compositions. In one example, a therapeutically effective amount or concentration is one that is sufficient to prevent advancement, delay progression, or to cause regression of a disease or condition, or which is capable of reducing symptoms caused by any disease or condition.

In one example, a desired effect is to reduce or inhibit one or more symptoms associated with a disease or condition characterized by hematological malignancy. The one or more symptoms do not have to be completely eliminated for the composition to be effective. For example, a composition can decrease the sign or symptom by a desired amount, for example by at least 20%, at least 40%, at least 50%, at least 80%, at least 90%, at least 95%, at least 98%, or even at least 100%, as compared to how the sign or symptom would have progressed in the absence of the composition or in comparison to currently available treatments.

The actual effective amount will vary according to factors such as the type of hematological malignancy to be protected against/therapeutically treated and the particular status of the subject (for example, the subject's age, size, fitness, extent of symptoms, susceptibility factors, and the like) time and route of administration, other drugs or treatments being administered concurrently, as well as the specific pharmacology of treatments for hematological malignancy for eliciting the desired activity or biological response in the subject. Dosage regimens can be adjusted to provide an optimum prophylactic or therapeutic response.

An effective amount is also one in which any toxic or detrimental side effects of the compound and/or other biologically active agent is outweighed in clinical terms by therapeutically beneficial effects. A non-limiting range for a therapeutically effective amount of treatments for hematological malignancy within the methods and formulations of the disclosure is about 0.0001 pg/kg body weight to about 10 mg/kg body weight per dose for one or both compounds in the combination, such as about 0.0001 pg/kg body weight to about 0.001 pg/kg body weight per dose for one or both compounds in the combination, about 0.001 pg/kg body weight to about 0.01 pg/kg body weight per dose for one or both compounds in the combination, about 0.01 pg/kg body weight to about 0.1 pg/kg body weight per dose for one or both compounds in the combination about 0.1 pg/kg body weight to about 10 pg/kg body weight per dose for one or both compounds in the combination, about 1 pg/kg body weight to about 100 pg/kg body weight per dose for one or both compounds in the combination, about 100 pg/kg body weight to about 500 pg/kg body weight per dose for one or both compounds in the combination, about 500 pg/kg body weight per dose to about 1000 pg/kg body weight per dose for one or both compounds in the combination, or about 1.0 mg/kg body weight to about 10 mg/kg body weight per dose for one or both compounds in the combination.

In some embodiments utilizing crenolanib, crizotinib, entospletinib (GS-9973, 6-(1H-indazol-6-yl)-N-(4-morpholin-4-ylphenyl)imidazo[1,2-a]pyrazin-8-amine), fedratinib (SAR302503, TG101348), filgotinib, ibrutinib (Imbruvica®), momelotinib (GS-0387, CYT387), pacritinib, pazopanib, PF-04965842, sorafenib, vandetanib (CAPRELSA®), venetoclax, the drug, or a pharmaceutically acceptable salt thereof, may be administered to a human patient once or twice daily at individual dosages of from about 50 mg to about 1,200 mg. In other separate embodiments, the individual dosages may be administered once or twice daily at individual dosages of from about 50 mg to about 200 mg; from about 50 mg to about 400 mg; from about 100 mg to about 400 mg; from about 200 mg to about 400 mg; from about 200 mg to about 600 mg; from about 400 mg to about 600 mg; from about 400 mg to about 800 mg; from about 600 mg and about 800 mg; from about 600 mg to about 1,000 mg; from about 800 mg to about 1,000 mg; from about 800 mg to about 1,200 mg; from about 1,000 mg to about 1,200 mg. In different embodiments, individual doses given once or twice daily may also be selected from the group of 50 mg, 100 mg, 150 mg, 200 mg, 250 mg, 300 mg, 350 mg, 400 mg, 450 mg, 500 mg, 600 mg, 700 mg, 800 mg, 900 mg, 1,000 mg, 1,100 mg, and 1,200 mg.

In some of the embodiments herein using flavopiridol (alvocidib), the drug may be delivered intravenously at dosages of from about 10 mg/m$^2$/day to about 20 mg/m$^2$/day, with individual dosages falling in the range of from about 10 mg/m$^2$/day to about 40 mg/m$^2$/day, about 10 mg/m$^2$/day to about 60 mg/m$^2$/day, about 10 mg/m$^2$/day to about 100 mg/m$^2$/day, about 50 mg/m$^2$/day to about 150 mg/m$^2$/day, and about 100 mg/m$^2$/day to about 150 mg/m$^2$/day.

In some embodiments herein using baracitinib, lenvatinib, ruxolitinib, YM-155, or a pharmaceutically acceptable salt thereof, the drug may be administered at from about 0.5 mg to about 40 mg once or more times daily. In some embodiments baracitinib, tofacitinib, trametinib, may be administered at dose ranges from about 0.5 mg to about 20 mg; from about 0.5 mg to about 15 mg; from about 0.5 mg to about 10 mg; and about 0.5 mg to about 5 mg. Individual doses administered once or twice daily include 0.5 mg, 1.0 mg, 2 mg, 3 mg, 4 mg, 5 mg, 6 mg, 7 mg, 8 mg, 9 mg, and 10 mg.

In some embodiments herein using cabozantinib, cediranib dasatinib (Sprycel®), foretinib, gandotinib (LY-2784544), lestaurnib (CP-701), peficitinib, quizartinib, RAF265, regorafenib, saracatinib, selumetinib, suntitinib, upadacitinib, or a pharmaceutically acceptable salt thereof, the drug may be administered at from about 0.5 mg to about 250 mg once or more times daily. In some embodiments baracitinib may be administered at dose ranges from about 1 mg to about 20 mg; from about 1 mg to about 40 mg; from about 1 mg to about 60 mg; about 1 mg to about 80 mg; from about 20 mg to about 80 mg; from about 40 mg to about 80 mg; from about 20 mg to about 60 mg; from about 20 mg to about 50 mg; from about 50 mg to about 150 mg; from about 80 mg to about 120 mg; and from about 100 mg to about 200 mg. Individual doses administered once or twice daily include 1.0 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, and 100 mg.

Determination of effective amount is typically based on animal model studies followed up by human clinical trials and is guided by administration protocols that significantly reduce the occurrence or severity of targeted disease or condition symptoms in the subject. Suitable models in this regard include, for example, murine, rat, rabbit, porcine, feline, non-human primate, and other accepted animal model subjects known in the arts. Using such models, only ordinary calculations and adjustments are required to determine an appropriate concentration and dose to administer a therapeutically effective amount of the treatments for hematological malignancies.

Results

To better understand genetic or transcriptional markers and mechanisms of drug sensitivity and resistance in AML, we developed a cohort of 672 primary specimens from 562 unique AML patients on which extensive functional and genomic interrogations were undertaken. The majority of samples (58%) were from patients with an initial diagnosis of AML and the majority of these represented de novo cases of AML (73% of initial diagnoses were de novo). Secondary AML that transformed from MDS or MPN accounted for 16% of the cohort, and a small percentage of cases (4%) were in a state of advanced MPN, MDS, or MDS/MPN overlap.

Comparative Genomic Landscape of AML

We performed exome sequencing on 622 of the specimens from the cohort representing 531 unique patients. We developed customized analytical pipelines that combined published algorithms with novel filtering, curation, and quality control steps.

Figure 2:
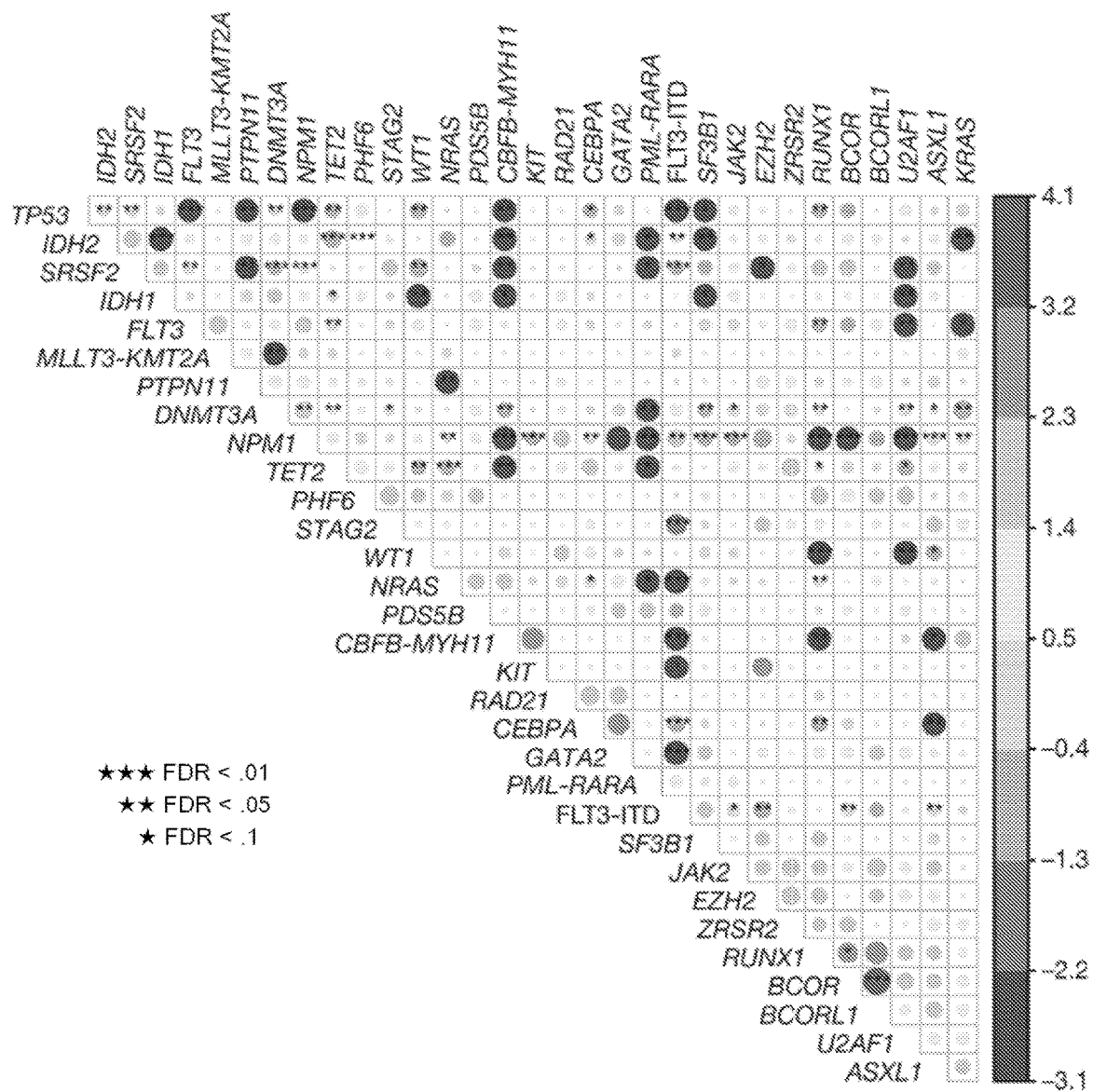
FIG. 2 reveals significant patterns of mutational co-segregation identified suggesting biological cooperativity of mutational events.

The final, high-confidence variant list revealed a diversity of point mutations and small insertion/deletions, with a range of 1-80 somatic variants (cohort median of 13 somatic variants). Comparison of the top 33 most commonly mutated genes across Beat AML and TCGA[6] showed generally similar frequencies. Higher frequency of mutations in SRSF2 were seen in our Beat AML cohort than in TCGA, and this difference was conserved comparing the whole Beat AML cohort as well as only the de novo cases in Beat AML with TCGA (FIG. 1). In contrast, mutational events that were seen at less than 2% cohort frequency across Beat AML and TCGA were much more divergent with variants in 221 mutant genes called in common, 939 mutant genes called only in TCGA, and over 1,500 mutant genes called only in Beat AML. Once again, this divergence in rare mutational events was consistent whether comparing only de novo, only transformed, or all Beat AML cases. Most of these divergent mutational events were observed in only single patients, however, there were mutations in 11 genes that were called in 1% or more of patients in Beat AML, but were not observed in TCGA or any other previous AML sequencing studies (CSMD2, NACAD, TENM2, ACAN, ADAMTS7, IGFN1, NBEAL2, PUF60, ZNF687, CELSR2, and GRIN2B). The pathogenic significance of these novel mutational events merits further study to understand which of these events may carry bona fide leukemogenic capacity. Finally, co-occurrence and exclusivity of the most frequent variants were computed revealing significant patterns of mutational co-segregation suggesting biological cooperativity of certain mutational events (FIG. 2).

Transcriptomic and Drug Sensitivity Landscape of AML

RNA sequencing was performed on 451 specimens from 411 patients to understand patterns of gene expression as they relate to clinical parameters of disease, genetic groups, and drug sensitivity profiles. Analysis of the 2,000 most variably expressed genes across the cohort revealed gene expression signatures that clustered strongly with many of the prominent genetic and cytogenetic disease groups, including chromosomal rearrangements causing gene fusion of RUNX1-RUNX1T1, CBFB-MYH11 or PML-RARA, and mutation of NPM1, DNMT3A and/or FLT3-ITD.

To understand the profile of sensitivity and resistance to a variety of small-molecule inhibitors, we profiled primary tumor cells from 409 specimens derived from 363 patients against a panel of 122 small-molecule inhibitors using an ex vivo drug sensitivity assay[41]. This panel contained graded concentrations of a drugs with activity against two-thirds of the tyrosine kinome as well as other non-tyrosine kinase pathways, including MAPKs, PI3K/AKT/mTOR, AMPK, ATM, Aurora kinases, CAMKs, CDKs, GSK3a/b, IκK, PKA, PKC, PLK1, and RAF. In addition, the library contained small molecule inhibitors with activity against the BCL2 family, BRD4, Hedgehog, HSP90, NOTCH/gamma-secretase, proteasome, survivin, STAT3, and WNT/beta-catenin. Drug sensitivity patterns were analyzed with respect to clinical and genetic features of tumors. We compared the average area-under-the curve (AUC) values for each drug between the de novo and transformed samples via a series of single factor ANOVAs. Generally, transformed cases showed less sensitivity to most drugs than de novo cases. Of the 122 drugs tested, 64 were significantly (FDR<0.1) more sensitive in the de novo samples, while only 1 drug Panobinostat (HDAC inhibitor) was significantly more sensitive in the transformed cases. In addition, we analyzed the concordance of drug sensitivity patterns with respect to predicted target gene, gene family, or pathway for each drug. This analysis revealed drug targets/families that were highly concordant amongst constituent members as well as drug families that were quite discordant. To create a global view of overall sensitivity or resistance of each case, we generated a heatmap of binary sensitive/resistant calls for each sample to each drug. We then annotated the sensitivity or resistance fraction of each case against ELN 2017 (FIG. 3) and WHO 2016 (FIG. 4) classifications.

Gene Signatures that Predict Drug Sensitivity or Resistance

Figure 4:
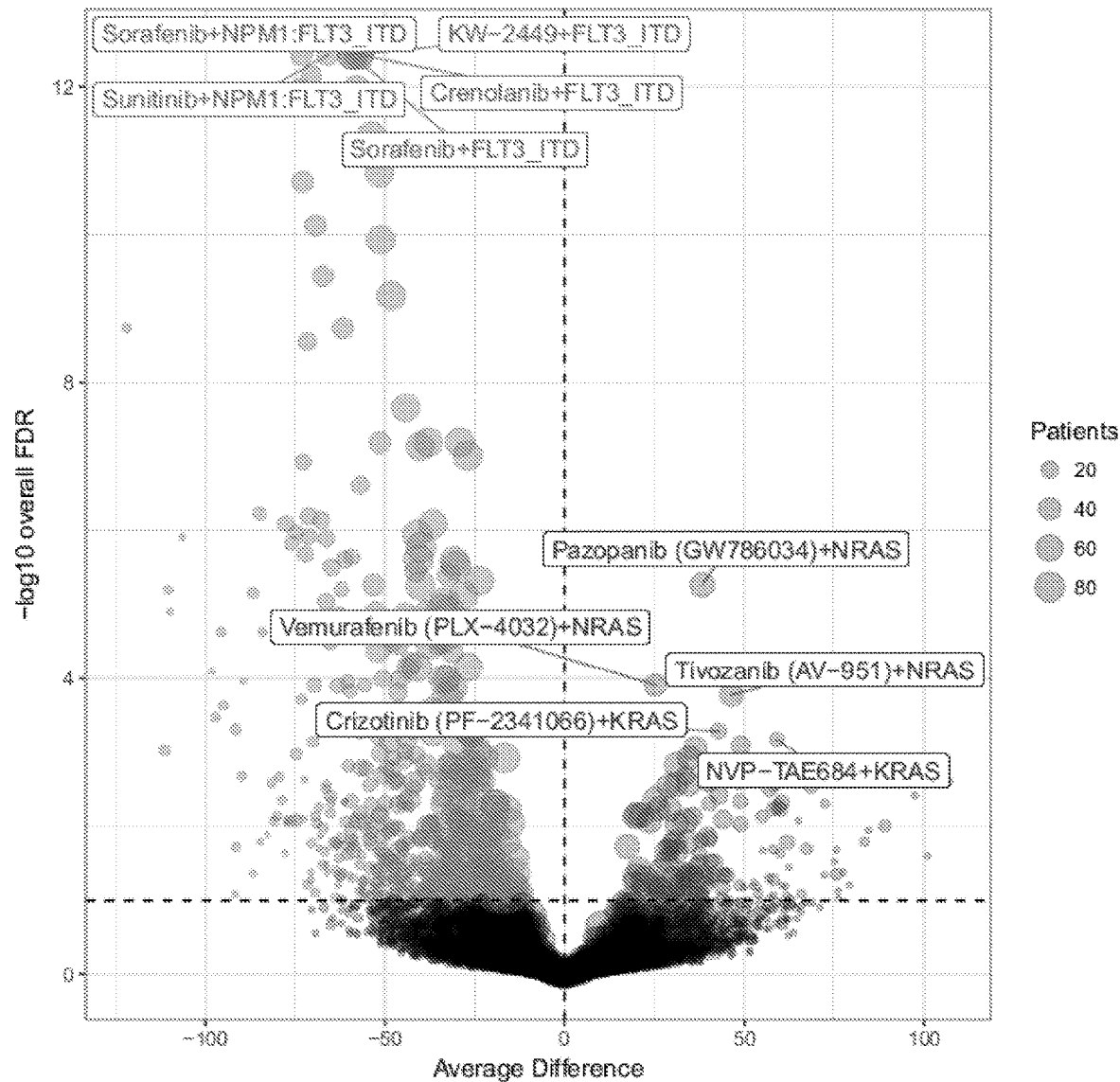
FIG. 4 represents the difference in average drug sensitivity of mutant versus WT cases for each drug/mutation pair plotted on the horizontal axis of a volcano plot with a test for statistical significance of the comparison plotted on the vertical axis.
Figure 5:
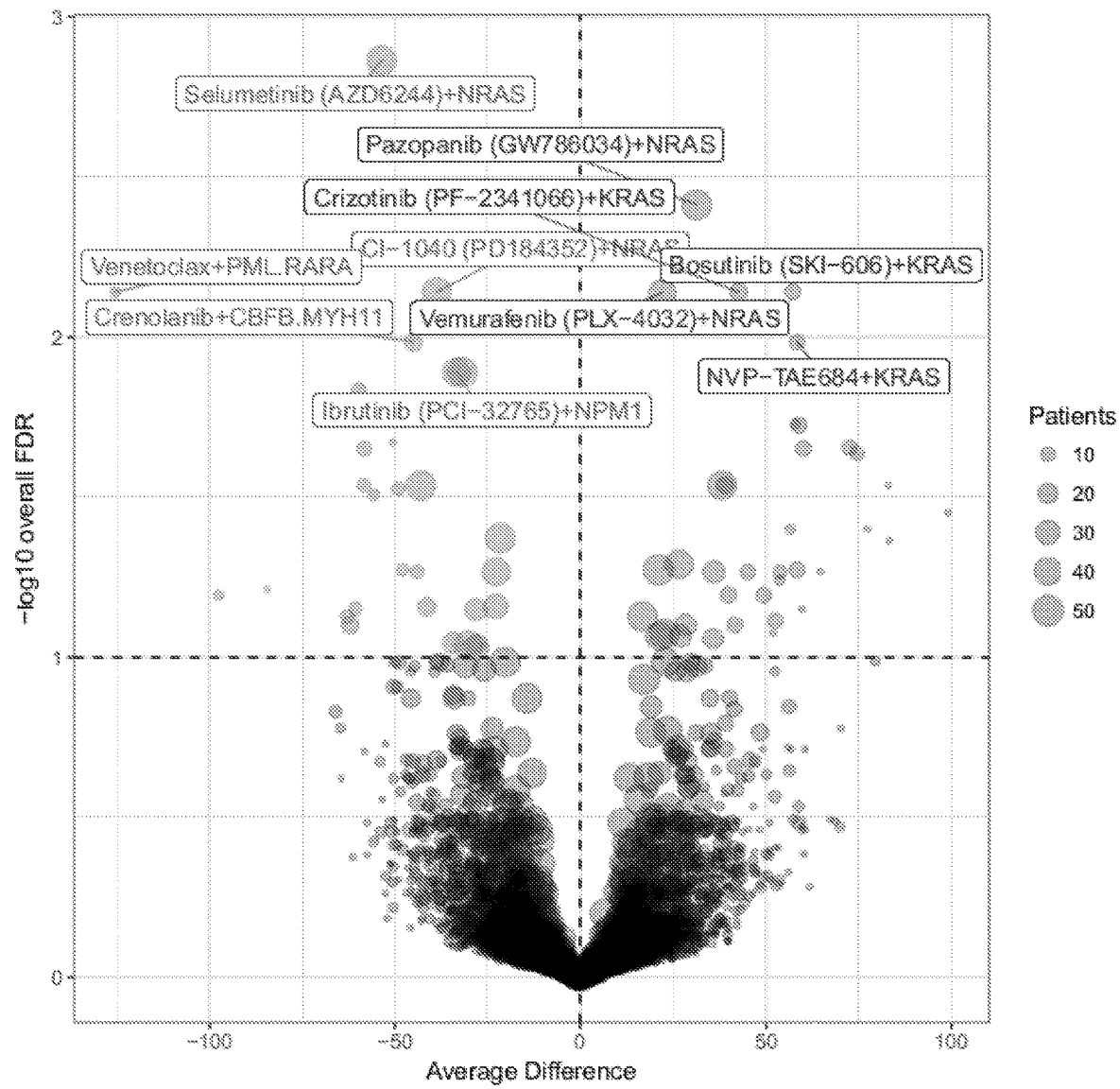
FIG. 5 plots the same analysis from the top panel using only cases that were wild type for FLT3.

In an effort to better understand genetic or transcriptional events that predict for sensitivity to small-molecule inhibitors, we performed a cohort analysis to assess correlation between drug sensitivity patterns and mutational events or gene expression levels. Correlation of drug sensitivity with mutational events was performed by assessing the range of sensitivity of cases with mutation of an individual gene (as well as co-occurring mutational events) versus cases with wild type sequence for that same gene. A broad summary of the full cohort results is displayed in a Circos plot, which shows gene events that correlate with any drug on the panel, and a Manhattan plot, which shows the degree to which each drug can be associated with any mutational event. The difference in average drug sensitivity of mutant versus wild type cases for each drug/mutation pair was plotted on the horizontal axis of a volcano plot with a test for statistical significance of the comparison plotted on the vertical axis (corrected for multiple comparison false discovery rate[42]; FIG. 4). Some of the associations that showed the highest levels of statistical significance involved the most common mutational event, FLT3-ITD, with sensitivity to direct inhibitors of FLT3 or inhibitors that target downstream FLT3 pathway mediators. This served as a proof-of-principle, since FLT3 inhibitors are known to be more effective against FLT3-ITD-positive AML. To reveal drug/mutation associations that were not biased by co-occurrence with FLT3-ITD, we also plotted the same analysis using only cases that were wild type for FLT3 (FIG. 5). To aid in discovery of potential mutational biomarkers of drug sensitivity, we plotted volcano plots that were specific to each individual drug (versus all possible mutational events) and for each individual gene (versus all possible drugs tested).

Figure 6:
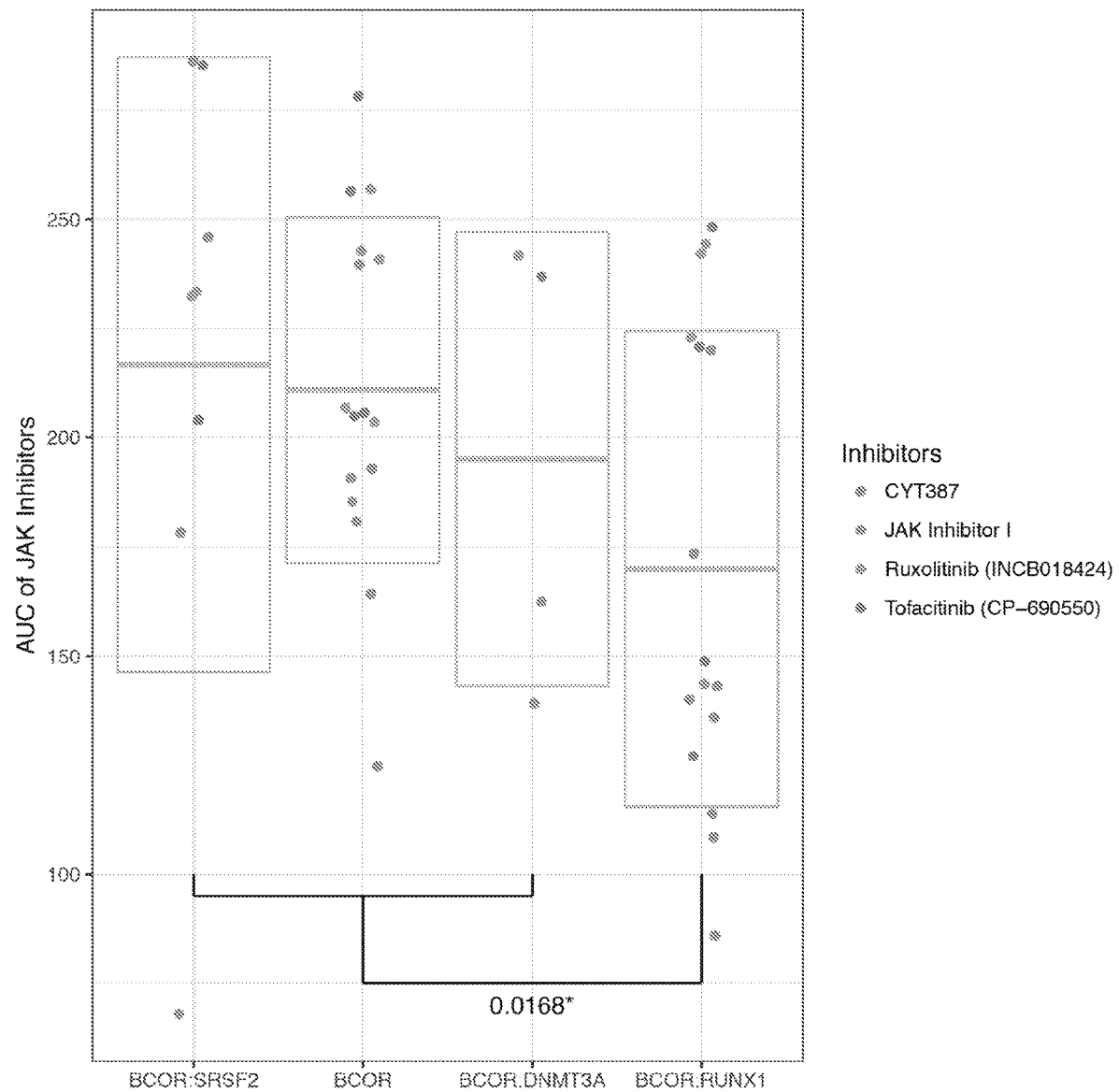
FIG. 6 depicts the AUC of JAK kinase inhibitors tested.

Mutation of several genes, most notably TP53 or ASXL1, were shown to cause a broad pattern of drug resistance. Interestingly, a few drugs trended more sensitive to TP53 mutant (e.g. elesclemol) or ASXL1 mutant (e.g. panobinostat) cases hinting at candidates to explore for these poor prognostic features. Mutation of NRAS or KRAS also correlated largely with resistance to most drugs, though did show the predicted sensitivity to MEK inhibitors. It was interesting to note a stronger association of NRAS than KRAS mutation with MEK sensitivity. IDH2 mutation conferred sensitivity to a broad spectrum of drugs, while mutation of IDH1 conferred resistance to most drugs. Mutation of RUNX1 correlated with sensitivity to PI3K/MTOR inhibitors, such as BEZ235, and to the multi-kinase VEGFR inhibitor, cediranib. Mutation of splicesome components U2AF1 and ZRSR2 correlated with novel sensitivity to several drugs. The mechanisms underlying these latter sensitivity correlations (and many others in the dataset) merit further investigation. A significant association was seen between mutation of FLT3, NPM1, and DNMT3A with sensitivity to the FDA approved drug, ibrutinib. Since these mutations exhibit a significant pattern of co-occurrence, we next examined every combination of single, double, or triple mutation of these genes with respect to ibrutinib. We observed that DNMT3A alone or DNMT3A/FLT3 double mutant cases were not significantly different than wild type, while cases with FLT3-ITD alone or any variation of NPM1 mutation (including cases with all three genes mutated) were significantly more sensitive than wild type. Ibrutinib is an inhibitor of BTK and TEC family kinases, although it can exhibit broad off-target effects when maintained in continuous culture with target cells. We noted that another kinase inhibitor with high specificity for SYK kinase, entospletinib, showed a similarly significant pattern of sensitivity for cases with FLT3-ITD and NPM1, potentially pointing to an operationally important target for this disease subset. Indeed, prior work has suggested SYK as an interacting target of FLT3-ITD in AML[43]. Finally, we wanted to perform an additional analysis that leveraged multiple inhibitors with common targets to see whether this approach could identify additional associations. We focused on correlation of the four selective JAK kinase inhibitors on our drug panel (momelotinib, ruxolitinib, tofacitinib, and JAK Inhibitor I) with mutation of BCOR alone or co-mutation of BCOR with DNMT3A, RUNX1, or SRSF2. By plotting the average difference of each JAK inhibitor between mutant and wild type groups of these four mutational categories and performing a one-way ANOVA analysis of the four groups, we found that co-mutation of BCOR with RUNX1 correlated with increased sensitivity to all four JAK kinase inhibitors, while BCOR mutation alone or co-mutation of BCOR with DNMT3A or SRSF2 showed no difference in sensitivity to the JAK kinase inhibitors, although BCOR mutation alone did show sensitivity to alternative drugs, such as the tankyrase/WNT inhibitor, XAV-939, and the multi-kinase inhibitor, crizotinib (FIG. 6). Collectively, these data suggest that JAK pathway dysregulation may represent a vulnerability within certain, specific combinatorial mutation settings and not in others.

We also performed an integration of drug sensitivity data with respect to patterns of gene expression, comparing the 20% of samples with lowest AUC versus the 20% with highest AUC and assessing the most differentially expressed genes between those sample sets. This analysis revealed significant (FDR<0.05) expression signatures for 78 testable drugs on the panel (78/119-65.5%). As an example, the 20% most and least sensitive cases to ibrutinib could be clearly distinguished by an expression signature of 17 genes as shown on a principle component analysis and heatmap of the 17 genes against the sensitive and resistant sample groups.

Figure 7:
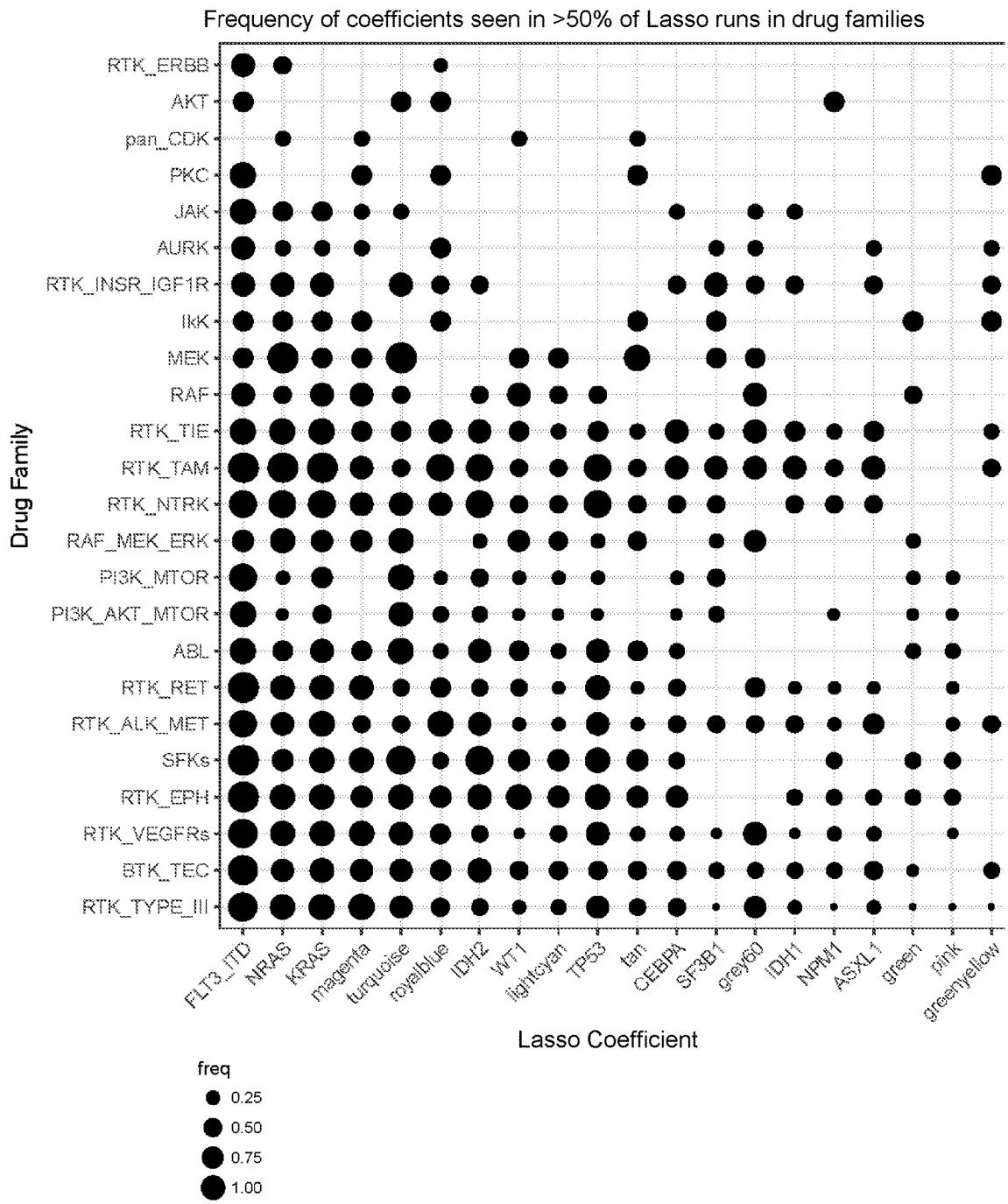
FIG. 7 summarizes frequency with which drug families associated with mutation and gene expression clusters in an iterative regression model.
Figure 7:
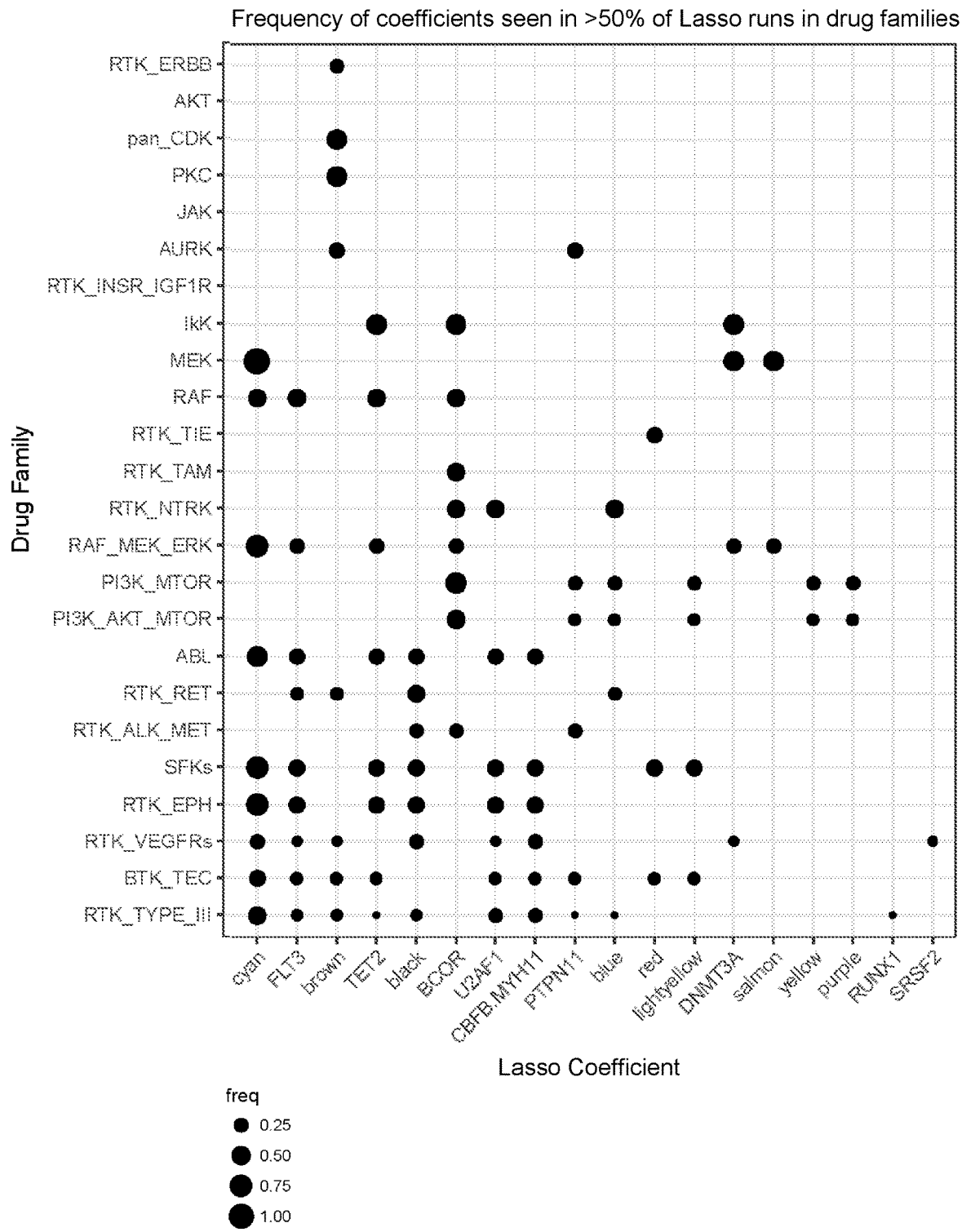

Finally, to assess the joint contributions of both mutation and system-level co-expression patterns (based on de-novo network inference) in predicting drug response, multivariate modeling was performed. This integrated analysis allows us to move beyond the significant associations of single mutations (such as FLT3-ITD and NPM1). We performed a WGCNA analysis of RNA-sequencing data that identified 14 sets of genes where gene expression patterns showed significant clustering across the cohort (clusters contained both elevated and decreased gene expression events). We performed iterative regression modeling (lasso) to understand how strongly any mutational event or any of these 14 gene expression clusters correlated with sensitivity or resistance to any of the drugs on the panel. We identified numerous, novel co-occurrences of mutations and expression clusters that were associated with drug sensitivity or resistance, with co-occurrences to ibrutinib sensitivity. For ibrutinib, these co-occurrences included a co-expression cluster of 345 genes (using a color labeling scheme and indicated as "turquoise") that correlated with drug sensitivity and frequently co-occurred with FLT3-ITD, which also correlated with drug sensitivity. There was significant overlap between this "turquoise" gene expression cluster and the 17-gene signature (indicated by the ratio of observed overlap to expected or representation factor: 13.6; P<1.734e-04). It is important to note that network analysis of this gene expression cluster highlighted enrichment for a number of immune-related pathways, which was not detected within the 17-gene signature, and this observation merits further investigation. We also identified a 110-gene subnetwork, which was associated with resistance to ibrutinib and was significantly associated with adverse ELN 2017 risk. To look more broadly at associations between mutations or gene expression clusters, we summarized the frequency with which drug families associated with mutations and gene expression clusters in our iterative regression modeling (FIG. 7).

Discussion

In sum, here we report the largest functional genomic dataset of primary tumor biopsies to date. We present a cohort of AML patient specimens for which we have performed detailed clinical annotations, genomic and transcriptomic analyses, and ex vivo drug sensitivity studies, and we provide analytical approaches for data integration. Each of these datasets alone has revealed new information about the biology and potential translational approaches in AML, and the integration of these datasets has been revealing of new markers and mechanisms of drug sensitivity and resistance that merit further study. These data have all been made publicly available through the NIH/NCI Genomic Data Commons resource, and we have developed tools to facilitate user interface with the dataset (www.vizome.org). We hope and expect that this public data release will stimulate further use of the data such that novel findings can be derived and parlayed into new clinical approaches for AML.

Methods

Whole Exome, Custom Capture Validation Sequencing and RNA-Sequencing

Whole exome sequencing was performed using Illumina Nextera RapidCapture Exome capture probes. Custom capture validation probes were assembled by Roche Sequencing Solutions. RNA-sequencing was performed using the Agilent SureSelect Strand-Specific RNA Library Preparation Kit. All sequencing was performed on an Illumina HiSeq 2500 System.

Ex Vivo Functional Drug Screens

Ex vivo drug screens were performed on freshly isolated mononuclear cells from AML samples as previously described[41].

REFERENCES

1 Jemal, A., Siegel, R., Xu, J. & Ward, E. Cancer statistics, 2010. *CA: a cancer journal for clinicians* 60, 277-300, doi:10.3322/caac.20073 (2010).

2 *National Cancer Institute: Surveillance, Epidemiology, and End Results Program*, <https://seer.cancer.gov/statfacts/html/amyl.html> (2018).

3 Papaemmanuil, E. et al. Genomic Classification and Prognosis in Acute Myeloid Leukemia. *N Engl J Med* 374, 2209-2221, doi:10.1056/NEJMoa1516192 (2016).

4 Arber, D. A. et al. The 2016 revision to the World Health Organization classification of myeloid neoplasms and acute leukemia. *Blood* 127, 2391-2405, doi:10.1182/blood-2016-03-643544 (2016).

5 Dohner, H. et al. Diagnosis and management of AML in adults: 2017 ELN recommendations from an international expert panel. *Blood* 129, 424-447, doi:10.1182/blood-2016-08-733196 (2017).

6 TCGA. Genomic and epigenomic landscapes of adult de novo acute myeloid leukemia. *N Engl J Med* 368, 2059-2074, doi:10.1056/NEJMoa1301689 (2013).

7 Byrd, J. C. et al. Pretreatment cytogenetic abnormalities are predictive of induction success, cumulative incidence of relapse, and overall survival in adult patients with de novo acute myeloid leukemia: results from Cancer and Leukemia Group B (CALGB 8461). *Blood* 100, 4325-4336, doi:10.1182/blood-2002-03-0772 (2002).

8 Patel, J. P. et al. Prognostic relevance of integrated genetic profiling in acute myeloid leukemia. *N Engl J Med* 366, 1079-1089, doi:10.1056/NEJMoa1112304 (2012).

9 Haferlach, T. et al. Landscape of genetic lesions in 944 patients with myelodysplastic syndromes. *Leukemia* 28, 241-247, doi:10.1038/leu.2013.336 (2014).

10 Lundberg, P. et al. Clonal evolution and clinical correlates of somatic mutations in myeloproliferative neoplasms. *Blood* 123, 2220-2228, doi:10.1182/blood-2013-11-537167 (2014).

11 Deininger, M. W. N., Tyner, J. W. & Solary, E. Turning the tide in myelodysplastic/myeloproliferative neoplasms. *Nat Rev Cancer* 17, 425-440, doi:10.1038/nrc.2017.40 (2017).

12 Busque, L. et al. Recurrent somatic TET2 mutations in normal elderly individuals with clonal hematopoiesis. *Nat Genet* 44, 1179-1181, doi:10.1038/ng.2413 (2012).

13 Genovese, G. et al. Clonal hematopoiesis and blood-cancer risk inferred from blood DNA sequence. *N Engl J Med* 371, 2477-2487, doi:10.1056/NEJMoa1409405 (2014).

14 Jaiswal, S. et al. Age-related clonal hematopoiesis associated with adverse outcomes. *N Engl J Med* 371, 2488-2498, doi:10.1056/NEJMoa1408617 (2014).

15 Xie, M. et al. Age-related mutations associated with clonal hematopoietic expansion and malignancies. *Nat Med* 20, 1472-1478, doi:10.1038/nm.3733 (2014).

16 Huang, M. E. et al. Use of all-trans retinoic acid in the treatment of acute promyelocytic leukemia. *Blood* 72, 567-572 (1988).

17 Shen, Z. X. et al. Use of arsenic trioxide (As2O3) in the treatment of acute promyelocytic leukemia (APL): II. Clinical efficacy and pharmacokinetics in relapsed patients. *Blood* 89, 3354-3360 (1997).

18 Nakao, M. et al. Internal tandem duplication of the flt3 gene found in acute myeloid leukemia. *Leukemia* 10, 1911-1918 (1996).

19 Tse, K. F., Mukherjee, G. & Small, D. Constitutive activation of FLT3 stimulates multiple intracellular signal transducers and results in transformation. *Leukemia* 14, 1766-1776 (2000).

20 Yamamoto, Y. et al. Activating mutation of D835 within the activation loop of FLT3 in human hematologic malignancies. *Blood* 97, 2434-2439 (2001).

21 Yokota, S. et al. Internal tandem duplication of the FLT3 gene is preferentially seen in acute myeloid leukemia and myelodysplastic syndrome among various hematological malignancies. A study on a large series of patients and cell lines. *Leukemia* 11, 1605-1609 (1997).

22 Knapper, S. et al. A phase 2 trial of the FLT3 inhibitor lestaurtinib (CEP701) as first-line treatment for older patients with acute myeloid leukemia not considered fit for intensive chemotherapy. *Blood* 108, 3262-3270, doi: blood-2006-04-015560 [pii]10.1182/blood-2006-04-015560 (2006).

23 O'Farrell, A. M. et al. An innovative phase I clinical study demonstrates inhibition of FLT3 phosphorylation by SU11248 in acute myeloid leukemia patients. *Clin Cancer Res* 9, 5465-5476 (2003).

24 Smith, B. D. et al. Single-agent CEP-701, a novel FLT3 inhibitor, shows biologic and clinical activity in patients with relapsed or refractory acute myeloid leukemia. *Blood* 103, 3669-3676, doi:10.1182/blood-2003-11-37752003-11-3775 [pii] (2004).

25 DeAngelo, D. J. et al. Phase 1 clinical results with tandutinib (MLN518), a novel FLT3 antagonist, in patients with acute myelogenous leukemia or high-risk myelodysplastic syndrome: safety, pharmacokinetics, and pharmacodynamics. *Blood* 108, 3674-3681, doi:10.1182/blood-2006-02-005702 (2006).

26 Stone, R. M. et al. Midostaurin plus Chemotherapy for Acute Myeloid Leukemia with a FLT3 Mutation. *N Engl J Med* 377, 454-464, doi:10.1056/NEJMoa1614359 (2017).

27 Smith, C. C. et al. Validation of ITD mutations in FLT3 as a therapeutic target in human acute myeloid leukaemia. *Nature* 485, 260-263, doi:nature11016 [pii]10.1038/nature11016 (2012).

28 Shih, A. H. et al. Mutational cooperativity linked to combinatorial epigenetic gain of function in acute myeloid leukemia. *Cancer Cell* 27, 502-515, doi:10.1016/j.ccell.2015.03.009 (2015).

29 Sato, T. et al. FLT3 ligand impedes the efficacy of FLT3 inhibitors in vitro and in vivo. *Blood* 117, 3286-3293, doi:10.1182/blood-2010-01-266742 (2011).

30 Traer, E. et al. FGF2 from Marrow Microenvironment Promotes Resistance to FLT3 Inhibitors in Acute Myeloid Leukemia. *Cancer Res*, doi:10.1158/0008-5472.can-15-3569 (2016).

31 Mardis, E. R. et al. Recurring mutations found by sequencing an acute myeloid leukemia genome. *N Engl J Med* 361, 1058-1066, doi:10.1056/NEJMoa0903840 (2009).

32 Wang, F. et al. Targeted inhibition of mutant IDH2 in leukemia cells induces cellular differentiation. *Science* 340, 622-626, doi:10.1126/science.1234769 (2013).

33 Rohle, D. et al. An inhibitor of mutant IDH1 delays growth and promotes differentiation of glioma cells. *Science* 340, 626-630, doi:10.1126/science.1236062 (2013).

34 Fiskus, W. et al. Combined epigenetic therapy with the histone methyltransferase EZH2 inhibitor 3-deazaneplanocin A and the histone deacetylase inhibitor panobinostat against human AML cells. *Blood* 114, 2733-2743, doi:10.1182/blood-2009-03-213496 (2009).

35 Schenk, T. et al. Inhibition of the LSD1 (KDM1A) demethylase reactivates the all-trans-retinoic acid differentiation pathway in acute myeloid leukemia. *Nat Med* 18, 605-611, doi:10.1038/nm.2661 (2012).

36 Daigle, S. R. et al. Selective killing of mixed lineage leukemia cells by a potent small-molecule DOT1L inhibitor. *Cancer Cell* 20, 53-65, doi:10.1016/j.ccr.2011.06.009 (2011).

37 Itzykson, R. et al. Impact of TET2 mutations on response rate to azacitidine in myelodysplastic syndromes and low blast count acute myeloid leukemias. *Leukemia* 25, 1147-1152, doi:10.1038/leu.2011.71 (2011).

38 Welch, J. S. et al. TP53 and Decitabine in Acute Myeloid Leukemia and Myelodysplastic Syndromes. *N Engl J Med* 375, 2023-2036, doi:10.1056/NEJMoa1605949 (2016).

39 Konopleva, M. et al. Efficacy and Biological Correlates of Response in a Phase II Study of Venetoclax Monotherapy in Patients with Acute Myelogenous Leukemia. *Cancer Discov* 6, 1106-1117, doi:10.1158/2159-8290.cd-16-0313 (2016).

40 DiNardo, C. D. et al. Safety and preliminary efficacy of venetoclax with decitabine or azacitidine in elderly patients with previously untreated acute myeloid leukaemia: a non-randomised, open-label, phase 1 b study. *Lancet Oncol*, doi:10.1016/S1470-2045(18)30010-X (2018).

41 Tyner, J. W. et al. Kinase Pathway Dependence in Primary Human Leukemias Determined by Rapid Inhibitor Screening. *Cancer Res* 73, 285-296, doi:0008-5472.CAN-12-1906 [pii]10.1158/0008-5472.CAN-12-1906 (2013).

42 Benjamini, Y. & Hochberg, Y. Controlling the false discovery rate: A practical and powerful approach to multiple testing. *Journal of the Royal Statistical Society, Series B (Methodological)* 57, 289-300 (1995).

43 Puissant, A. et al. SYK is a critical regulator of FLT3 in acute myeloid leukemia. *Cancer Cell* 25, 226-242, doi: 10.1016/j.ccr.2014.01.022 (2014).

FIGURE LEGENDS

FIG. 1—The 33 mutational events that were cumulatively most frequent in the Beat AML and TCGA cohorts (union of 25 most frequent for each cohort) are plotted displaying the frequency of each mutational event in each cohort with the top row representing the full Beat AML cohort and the middle bar representing only the de novo cases in the Beat AML cohort. Note that mutations were summarized by gene as was done by TCGA whereas the internal tandem duplications in FLT3 were kept separate in the rest of the manuscript.

FIG. 2—The extent of co-occurrence or exclusivity of the most recurrent mutational events in the Beat AML cohort were assessed and plotted on a dot plot indicating the odds ratio of co-occurrence (blue) or exclusivity (red) using color-coding and circle size as well as asterisks that indicate FDR-corrected statistical significance of the mutational association pattern.

Figure 3:
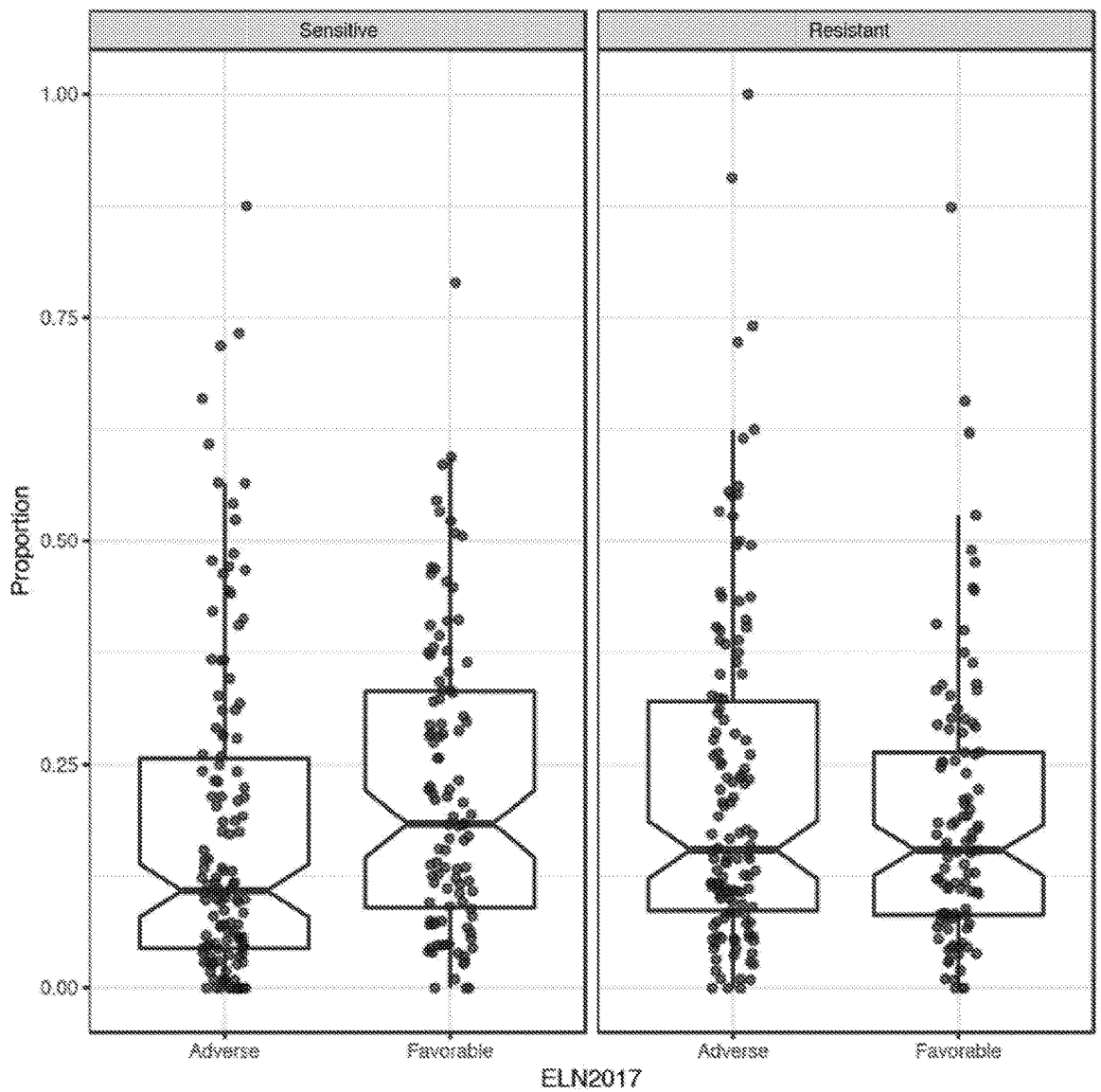
FIG. 3 represents the annotated sensitivity or resistance fraction of each case against ELN 2017 classification.

FIG. 3—Transcriptomic Landscape of the Beat AML Cohort. 451 specimens from 411 unique AML patients were subjected to RNA-sequencing. The 2,000 genes with greatest differential expression across these unique AML patients are displayed on the heatmap. The heatmap is annotated with disease type, ELN risk stratification groups, genetic, and cytogenetic features of disease as noted in the figure legend.

FIG. 4 All mutational and cytogenetic events where at least 5 patient samples with evaluable drug sensitivity data exhibited mutation of the gene were assessed for average difference in area under the curve between mutant and wild type samples. A statistical comparison of the mutant versus wild type drug sensitivity patterns (corrected for multiple comparisons) was also computed. Average difference between mutant and wild type cases is plotted on the horizontal axis with FDR-corrected q-value plotted on the vertical axis.

FIG. 5—The same analysis as described above was conducted for the subset of the cohort that was negative for FLT3-ITD. Volcano plots that are specific to each drug or mutant gene in the dataset are available with interactive features in our online data browser (www.vizome.orq) and conditional "by drug" and "by gene".

SUPPLEMENTAL METHODS

Patient Samples

Mononuclear cells were isolated by Ficoll gradient centrifugation from freshly obtained bone marrow aspirates or peripheral blood draws. Cell pellets were snap frozen in liquid nitrogen for subsequent DNA isolation (Qiagen, DNeasy Blood & Tissue Kit), freshly pelleted cells were lysed immediately in GTC lysate for subsequent RNA isolation (Qiagen, RNeasy Mini Kit), and freshly isolated mononuclear cells were plated into an ex vivo drug sensitivity assays within 24 hours (described in detail below). Skin punch biopsies were collected at the site of Jamshidi needle insertion for subsequent bone marrow biopsies and genomic DNA was isolated for use as matched normal controls for exome sequencing (Qiagen, DNeasy Blood & Tissue Kit). Clinical, prognostic, genetic, cytogenetic, and pathologic lab values as well as treatment and outcome data were manually curated from patient electronic medical records. Patients were assigned a specific diagnosis based on the prioritization of genetic and clinical factors as determined by WHO guidelines. To prevent re-identification, any patient over the age of 90 was placed into a >90 aggregated age bracket. Genetic characterization of the leukemia samples included results of a clinical deep-sequencing panel of genes commonly mutated in hematologic malignancies (Sequenome and GeneTrails® Hematologic Malignancies Gene Panel (OHSU); Foundation Medicine (UTSW); Genoptix; and Illumina).

Whole Exome and Custom Capture Validation Sequencing

For exome sequencing, Illumina Nextera® Rapid Capture Exome capture probes and protocol were utilized, which provided coverage of 37 Mb of genomic DNA coding regions. Briefly, following initial QC on a TapeStation System (Agilent), 50 ng of intact genomic DNA was fragmented and tagged (tagmentation) in a single step. Following clean-up, the tagmented DNA was amplified by 10 cycles of PCR, which added the indexed adaptors for clustering and sequencing. Libraries were hybridized to capture pools in 12 sample sets with two rounds of hybridization performed to increase specificity. Libraries recovered with streptavidin magnetic beads were amplified by 10 cycles of PCR, unincorporated reagents were removed with AMPure beads (Agencourt), and validated on the TapeStation. Quantification of capture pools was done using real time PCR (Kapa). Libraries were denatured, flow cells set up using the cBot (Illumina), and run on a HiSeq 2500 using paired end 100 cycle protocols. For the AML tumor samples, 5 or 6 lanes were run per capture group. For the matched skin biopsy samples, 3 lanes (or equivalent) were run per capture group.

For validation of sequencing results, an 11.9 megabase custom capture library was developed that provided coverage of all variants previously reported in AML as well as all new variants detected from exome sequencing in this study. This capture library was then applied to sequence 96 specimens that had previously been subjected to whole exome sequencing for validation of variant calls.

Whole Exome Sequencing Data Processing

Initial data processing and alignments were performed with commonly used analytical tools. For each flowcell and each sample, the FASTQ format files were aggregated into single files for read 1 and 2. During this process these reads were trimmed by 3 on the 5' end and 5 on the 3' end. BWA MEM version 0.7.10-r789[1] was used to align the read pairs for each sample-lane FASTQ file. As part of this process, the flowcell and lane information was kept as part of the read group of the resulting SAM file. The Genome Analysis Toolkit (v3.3) and the bundled Picard (v1.120.1579) were used[2] for alignment post-processing. The files contained within the Broad's bundle 2.8 were used including their version of the build 37 human genome (These files were downloaded from: ftp://ftp.broadinstitute.org/bundle/2.8/b37/). The following steps were performed per sample-lane SAM file generated for each CaptureGroup:

The SAM files were sorted and converted to BAM via SortSam

MarkDuplicates was run, marking both lane level standard and optical duplicates

The reads were realigned around indels from the reads—RealignerTargetCreator/IndelRealigner.

Base Quality Score Recalibration

The resulting BAM files were then aggregated by sample and an additional round of MarkDuplicates was carried out at the sample level. Quality control reports were generated using the ReportingTools[3] and qrqc[4] Bioconductor R packages along with output files from the sequencing core and the alignment output files. Each AML sample BAM was paired with its skin biopsy pair and an additional round of indel realignment was carried out to ensure consistency of genotypes between the two samples. If an AML sample did not have a pair, the indel realignment was instead done at the sample level.

Whole Exome Sequencing Variant Detection

For genotyping, each AML/skin biopsy pair was realigned at the sample level and then genotyped for single nucleotide variations using Mutect v1.1.7[5] and Varscan2 v2.4.1[6]. Indels were produced using Varscan2. Each VCF file was annotated using the Variant Effect Predictor v83 against GRCh37[7]. The resulting VCF files were filtered to include only those annotated to a gene and were converted to MAF format using the vcf2maf v1.6.6 tool[8].

Mutect v1.1.7[5] was run using default parameters except that no limit was placed on the number or frequency of the alternative allele frequency in the normal to help address normal contamination.

Varscan2 v2.4.1[6] was run in somatic mode with the recommended filtering scheme[9] except as shown in the table below.

| Parameter | Current |
|---|---|
| Initial Calls | |
| Min coverage | 3 |
| Min variant Frequency | .08 |
| Het P-value | .1 |

-continued

| Parameter | Current |
|---|---|
| Somatic Calls | |
| Min tumor frequency | .08 |
| Max normal frequency | 1 |
| High confidence P-value | .1 |
| Post Processing | |
| Max variant avgrl | 0 |
| Max reference avgrl | 0 |

Indels and SNVs were produced for the tumor-only samples again using Mutect without a specified normal for consistency and VarScan2 in mpileup2indel or mpileup2snp mode respectively.

These variants were assigned to their most deleterious effect on Ensembl transcripts using Ensembl VEP v83 on GRCh37. This assignment was done using the same VEP parameters as the vcf2maf (v1.5.0) program.

The TCGA AML variants[10] in MAF form were downloaded from the GDC archive site: https://portal.gdc.cancer.gov/legacy-archive/files/c410d927-d49c-4d4f-8356-601bee563ebe. The MAF was converted to VCF files using the vcf2maf suite[11]. The resulting VCF files were lifted over from NCB136 to GRCh37 of the human genome using CrossMap[12]. Only those variants that successfully lifted over were kept.

Variants from Table S2 in Jaiswal et al 2014[13] were extracted and further processed removing variants that were ambiguous in terms of external sources and could not be found in their WES variants. The unique set of BeatAML variants was annotated relative to RefSeq transcripts using Ensembl VEP similar to above and all consequences were kept. This set of variants and consequences was searched against the set of processed Jaiswal variants.

Using the runs from MuTect and VarScan, these data were next filtered to keep only the protein impacting SNVs and indels from Mutect and VarScan2 and filtered requiring that the variants had at least 5 reads and either not be seen in the exome aggregation consortium (ExAC)[14] or be seen at a frequency <0.01. These data present several additional challenges. First somatic calls cannot be obtained directly from the tumor-only samples, second there is always a possibility of tumor contamination of the skin samples for those samples that were paired. To address these issues and maximize comparability we used an iterative approach. The following was done separately for the two genotypers:

An initial set of higher confidence somatic mutations were retrieved from the paired tumor/normal samples requiring tumor variant allele frequency (VAF)>=8% and normal VAF<=5% in addition to the significance tests already performed by the programs.

A list of all candidate mutations was collated requiring that a mutation was either seen in the high confidence somatic set, the set of variants from Jaiswal et al or from the lifted over set of variants from the TCGA AML paper.

Mutations from the overall set were kept if:

The overall number of calls in the paired samples was not more than twice the number of high confidence somatic calls The tumor-only frequency for the calls was less than 50% greater than the number of calls in the paired samples The mutation was seen in Jaiswal/TCGA list High Confidence somatic mutations were kept regardless The data from the two genotypers were combined along with FLT3-ITD calls from Pindel[15]. Comparing our variant lists from whole exome sequencing versus our custom capture validation sequencing, we noticed, similar to others[16], that low allele frequency C→A variants (<15%) tended to have poor concordance (7.7%; data not shown) between the initial run and the technical validation run. These variants were removed in these data and along with a curated 'blacklist' of known problematic variants/genes including mitochondrial DNA variants. In addition, all variants that were seen in a cumulative list of BeatAML normal samples at a frequency greater than 1% were removed. Cumulatively, of this set, 94% of covered single-nucleotide variants were validated with 82% of insertion/deletion calls also being confirmed with validation sequencing.

Manual review was then carried out in the following steps:

a.) The addition back of all Jaiswal flagged rows.

b.) Reviewed all TCGA flagged rows for VAF pattern that matched or did not match with known drivers in same specimen. Some TCGA variants were added back based on convincing VAF pattern and known pathogenic role, other TCGA variants were kept excluded based on VAF pattern unlike known drivers in same specimens.

c.) Other variants were added back based on other specimens that had the same variant that was still on the include list and VAF pattern looked convincing for inclusion.

d.) All Jaiswal genes with only frameshift/nonsense variants were manually reviewed and missense mutations were manually removed.

e.) Genes/variants that were on both the include and exclude lists were manually reviewed and were removed if c to a with over 15% VAF, did not validate, and/or VAF pattern unlike known drivers in same specimen f.) Further review of all genes in summary sheet with cohort frequency of 8 or more (1% of more). Any that were not familiar from knowledge of AML literature were manually reviewed for VAF patterns that did or did not match known drivers within same specimens. Those that did not match were manually removed.

After this manual review, additional curated mutations from the UnifiedGenotyper run were added back in along with a curated set of variants from tumor-only patients in Jaiswal et al genes. The tumor-only AML samples utilized in Zhang et al were removed and utilized for that study.

Internal FLT3-ITD and NPM1 Mutation Detection

A subset of samples was tested for FLT3-ITD and NPM1 mutation status using an internally run PCR assay and capillary electrophoresis. Genomic DNA was extracted from fresh blood or bone marrow aspirates of AML patients was used to detect the presence or absence of FLT3-ITD and NPM1 4 bp insertion mutations[17,18]. Primers for FLT3 spanned approximately 330 bp to include the common internal duplication site[17]. Primers for NPM1 spanned approximately 170 bp to cover the clustered multiple insertional or insertion/deletion sites[18,19]. Primers were HPLC-purified by the manufacturer. The multiplex PCR reaction solution consisted of 100 ng gDNA, 10 pmol of the respective forward and reverse primers for FLT3 and NPM1, 25 mmol/l MgCl$_2$, 2·5 mmol/l dNTP, 5 µl 10×PCR buffer, 0·2 µl AccuTaq DNA polymerase and water in a total volume of 50 ul[20]. The PCR conditions were: initial denaturing for 5 min at 94° C., followed by 30 cycles at 94° C. for 30 s, 56° C. for 45 s and 72° C. for 30 s with a final cycle of 10 min at 72° C. The PCR products were diluted 1:10 and analyzed by capillary electrophoresis on a QiAxcel high resolution DNA cartridge according to the manufacturer's protocol.

Forward Primer FLT3: 5'-AGCA ATT TAG GTA TGA AAG CCA GCTA-3'
Reverse Primer FLT3: 5'-CTT TCA GCA TTT TGA CGG CAA CC-3'
Forward Primer NPM1: 5'-GTT TCT TTT TTT TTT TTT CCA GGC TAT TCA AG-3'
Reverse Primer NPM1: 5'-CAC GGT AGG GAA AGT TCT CAC TCT GC-3'

Derivation of FLT3-ITD and NPM1 Consensus Calls

Consensus FLT3-ITD and NPM1 mutation calls were determined by comparing the internal capillary PCR test (internal; method described above), the CLIA/CAP laboratory run test (Sequenome, GeneTrails®, Foundation Medicine, Genoptix, Illumina). The internal test was used for the sample consensus call when available as it was performed on the exact sample that was used for further ex vivo drug sensitivity assays. Where discordance existed between the internal test versus the CLIA lab test results, the sample was flagged for manual review. The trace file for the internal test was visually inspected and if discordance with the CLIA/CAP test results persisted, the whole exome sequencing data was then used to help determine the consensus call.

Derivation of CEBPA Biallelic Consensus Calls

N-terminal and C-terminal mutations have been described to occur on opposing alleles and patients harboring CEBPA biallelic mutations have been shown to fall into a favorable risk category[21]. Patients were scored positive for biallelic CEBPA mutation if described in the clinical notes as biallelic or double positive. Patients were also scored as CEBPA biallelic if both N-terminal and C-terminal mutations were identified in the whole exome sequencing data.

RNA-Sequencing and Data Processing

All samples were sequenced using the Agilent SureSelect Strand-Specific RNA Library Preparation Kit on the Bravo robot (Agilent). Briefly, poly(A)+ RNA was chemically fragmented. Double stranded cDNAs were synthesized using random hexamer priming with 3' ends of the cDNA adenylated then indexed adaptors were ligated. Library amplification was performed using three-primer PCR using a uracil DNA glycosylase addition for strandedness. Libraries were validated with the Bioanalyzer (Agilent) and combined to run 4 samples per lane, with a targeted yield of 200 million clusters. Combined libraries were denatured, clustered with the cBot (Illumina), and sequenced on the HiSeq 2500 using a 100-cycle paired end protocol. In addition to the AML samples, there was also a sample of purified CD34+ cells from healthy control bone marrow, which was included in each sample group (for a total of 12 times sequencing this control RNA). This control served as both a healthy comparator and a quality check on inter-group batch effects. 21 additional, individual healthy bone marrow samples were also included, two of which were CD34- selected with the other 19 being whole mononuclear bone marrow cells from healthy donors. For each flowcell and each sample, the FASTQ files were aggregated into single files for read 1 and read 2 (if not already done by the sequencing core). During this process these reads were trimmed by 3 on the 5' end and 5 on the 3' end. Alignments of reads was performed using the subjunc aligner (1.5.0-p2)[22]. BAM files obtained from subjunc were used as inputs into featureCounts (1.5.0-p2)[23] and gene-level read counts were produced. For a reference genome, the GRCh37 build provided by the Broad as part of the GATK bundle was used. Gene assignments were based on the Ensembl build 75 gene models on GRCh37. See the parameters below for software usage.

subjunc -i/path/to/reference/-u -r fastq1 -R fastq2 -o outputBAMFilename -I 5 -T 7 -d 50 -D 600 -S fr
featureCounts -a Homo_sapiens.GRCh37.75.gtf -o output -F GTF -t exon -g gene_id -s 2 -C -T 10 -p -P -d 50 -D 600 -B BAM_files The data was collated from featureCounts matrices and all genes with no counts across the samples were excluded. Genes with duplicate gene symbols and those where the counts were <10 for 90% or more of the samples were additionally removed prior to normalization similar to the approach suggested for weighted gene correlation network analysis (WGNCA)[24]. Samples for which their median expression was less than 2 standard deviations below the average were removed from the dataset (N=10). Normalization was performed using the conditional quantile normalization procedure[25], which produced GC-content corrected log 2 reads per kilobase per million mapped reads (RPKM) values. This procedure produces both offsets to be used in conjunction with edgeR as well as a matrix of log 2 normalized RPKM values for clustering.

In addition, the subjunc BAM files were processed using the RNA-sequencing genotyping protocol (as of GATK v3.3) which was similar to the WES protocol described in the 'Whole Exome Sequencing' section including for each sample:

MarkDuplicates
SplitNCigarReads
RealignerTargetCreator/IndelRealigner.
Base Quality Score Recalibration The resulting BAM files were used to produce RNA genotypes using the UnifiedGenotyper for the purposes of QC and ethnicity estimation. Gene fusion data was additionally generated using the TopHat-Fusion (v2.0.14) program using default parameters[26].

Coexpression Network Formation

We formed coexpression modules using the WGCNA procedure on the RNA-sequencing data from the 'RNA-Sequencing and Data Processing' section. All RNA-sequencing samples were used to form the set of modules. Due to the heterogeneity of clinical expression data we generated 'signed hybrid' networks using 'bicor' correlation setting the max proportion of outliers to 0.1[27]. We ran the procedure multiple times, varying several parameters to choose the most relevant set for further analysis. The WGCNA procedure was run on datasets formed from the top 2,000 and 5,000 most variable genes. For each dataset we set the 'power' variable to either 2 or 3. For each of these runs we varied the module detection parameters of dynamic-TreeCut[24], namely the deepSplit parameter was set to 0 or 2 and the pamStage parameter was set to TRUE or FALSE. For each of these sets of modules we computed a series of module quality statistics[28], mean correlation, mean adjacency, mean MAR, mean KME, proportion of variability explained and the mean cluster coefficient. Significance of modules was determined by computing a Zscore of each of these values relative to the mean and standard deviation of those from 100 random assignment of modules. We chose the set of modules to use in our analyses as those that were most correlated with the 'specimentSpecificDx' using the module quality as a tie-breaker. The analysis set of modules was chosen to be the version using the 5,000 most variable genes, power set to 2 and modules formed using deepSplit=2 and pamStage=F. Of this set of modules only the grey module didn't have a summary Z statistic (median across the 4 density measures) of at least 2. Additionally after correcting the data using the estimated principal components[29], the module structure didn't change appreciably (data not shown).

Quality Control

The UnifiedGenotyper runs for both the WES and RNA-sequencing were combined into a single VCF file using the GATK CombineVCFs functionality. This combined VCF file was converted to a GDS file using SNPRelate (1.12.2)[30]. Note the version is an upper bound as several versions were used across the entire project). The overall similarity of the genotypes of each pair of samples were computed, termed identity by state (IBS) and a hierarchical clustering was performed using one minus this similarity. From this clustering and visualization we had devised hard cutoffs for further inspection based on the types of data being compared. For instance samples not meeting the specified IBS thresholds (DNA-DNA=0.9; RNA-RNA=0.83; DNA-RNA=0.89) were subject to manual review. Based on the dendrogram structure as well as the clinical/lab information, samples were either excluded, assigned to a different patient ID or in rare cases assigned to a different sample. It was observed that bone marrow transplants between sample collections produced a noticeable but milder effect in these dendrograms and such samples were flagged for removal in RNA-sequencing analysis and for treatment as tumor-only samples in the WES analysis as is described in the 'WES Variant Detection' section.

Fusion Annotation for Analysis

Fusions calls were determined from a consensus of three datatypes, a specific diagnosis categorization at the time of sample acquisition, current set of clinical karyotypes and fusions detected in RNA-sequencing data by TopHat-Fusion. All sources were limited to the same set of known fusions: RUNX1-RUNX1T1, CBFB-MYH11, MLLT3-KMT2A, DEK-NUP214, GATA2-MECOM and PML-RARA. It was determined that the RNA-sequencing calls did not provide additional resolution in detecting these known fusions and was not performed on all the samples so the consensus was limited to the clinical karyotype calls as well as the specific diagnosis categorization (which was determined based on karyotype and other cytogenetic clinical tests). Overall the calls were based on the karyotype data except in 10 cases, 3 where the karyotype and diagnosis was sufficiently complex to warrant a separate 'Complex' categorization. The remaining 7 of these cases were set to the specific diagnosis classification. It should be noted there was additional support from the RNA-sequencing data for several of these cases.

Ethnicity

The combined RNA and WES VCF from the 'Quality Control' step was merged with a set of Hapmap genotypes[31] lifted over to build 37. The SNPRelate package was used to convert the VCF to GDS, perform LD pruning using an LD threshold of 0.2, MAF cutoff of 0.05 and allowing a missing rate of 0.3 and calculation of the principal components. The methodology of Zheng and Weir 2015[32] was used to assign admixture proportions relative to the HapMap samples using the principal components. Each sample was assigned to an ethnicity group based on the group with the maximum admixture proportion. If the maximum was 50% or less, we labeled it Admixed. As we have observed previously that the clustering of ethnicities for RNA-sequencing samples are more diffuse than exome sequencing, we assigned the final inferred ethnicity to each patient based on the distinct WES calls if available, deferring to RNA-sequencing only if not available. If multiple exome sequencing samples were present with discrepant calls, the patient was subject to manual review. The only patient where this occurred was a self-identified Hispanic who had 2 RNA samples and an exome sequencing sample inferred as White and one exome sample inferred to be HispNative. Only the White call for the exome sequencing had an admixture proportion over 0.5. The patient was kept consistent with the self-identification and labeled as HispNative.

Sex

For DNA, coverage is first computed over the Y chromosome and the counts for each sample are added up and log 10 transformed (after adding 1 to all the counts). K-means clustering is used to assign samples to 2 clusters with the cluster with the lower mean labeled as the Female cluster. For RNA-sequencing, counts were converted to counts per million (CPM) after applying the Trimmed Mean of M scaling normalization[33]. A set of 28 genes chosen to successfully discriminate the genders via DE analysis over multiple studies (data not shown) were used in conjunction with Kmeans clustering to form two clusters. The Female cluster was labeled based on high XIST expression.

ELN 2017 Classification

This procedure is based off of the categorization in Table 5 of the 2017 ELN update paper[34]

Karyotypes in the clinical file were first cleaned and parsed into clones/subclones and distinct abnormalities using standard conventions[35]. The current representation was corrected for nomenclature type (e.g. idem vs sl) in a basic manner. For instance, ambiguous events such as chromosomal loss (e.g. −15) was not corrected for whether the preceding clone had a counteracting gain. Also, additional +/− symbols in conjunction with valid karyotype operators in a separate clone (e.g. +del(12)(q?15) or -del(12)(q?15))) were treated separately with gains (+) being kept in the unique count of events and losses (−) being removed.

Abnormalities were first checked for the following categories:
 1. RUNX1-RUNX1T1
 2. CBFB-MYH11
 3. MLLT3-KMT2A
 4. DEK-NUP214
 5. KMT2A-*
 6. BCR-ABL1
 7. GATA2-MECOM
 8. −5/del(5q) (termed minus_5)
 9. −7 (termed minus_7)
 10.-17 (termed minus_17)

Note the bold were further considered to be WHO recurrent fusions. The number of unique abnormalities (across clones) was then computed. Whether or not a karyotype was considered to be polyploid was also recorded (at least 60 chrs or '(>=3)n' or label). NPM1, FLT3-ITD, and biallelic CEBPA were derived from consensus calls. FLT3-ITD allelic ratios were determined solely for the samples with an internal assay. The MAF values of the internal assay were converted to a ratio using the formula MAF/(1-MAF). RUNX1, ASXL1 and TP53 were derived from the clinical genotypes. Abn_17 calls were manually curated from the karyotype data and clinical genotype calls respectively. The determination of ELN 2017 categories proceeds by assigning TRUE/FALSE/NA values to one or more of the 5 columns (3 ELN and 2 ambiguous) in the following way:
 1. isFavorable is considered TRUE if a sample has at least one of the following:
  a. RUNX1-RUNX1T1
  b. CBFB-MYH11
  c. Positive NPM1 and negative FLT3-ITD d. Positive NPM1 and positive FLT3-ITD with allelic ratio <0.5
   e. Biallelic CEBPA
 2. isFavorableOrIntermediate
   a. NPM1 is positive and FLT3-ITD is positive but the allelic ratio is not available
 3. isAdverse is considered TRUE if a sample has at least one of the following:
   a. DEK-NUP214
   b. KMT2A-*
   c. BCR-ABL1
   d. GATA2-MECOM
   e. minus_5
   f. minus_7
   g. minus_17
   h. abn_17
   i. 3 or more abnormalities and not a WHO recurrent fusion
   j. One monosomy (autosomal) and at least one additional abnormality except for CBFB-MYH11
   k. Positive RUNX1 or ASXL1 and not considered to be isFavorable or isFavorableOrIntermediate
   l. Positive TP53
 4. isIntermediate is considered TRUE if a sample has at least one of the following:
   a. MLLT3-KMT2A
   b. NPM1 positive and positive FLT3-ITD with allelic ratio >=0.5
   c. NPM1 negative and negative or low allelic ratio (<0.5) FLT3-ITD
   d. At least one abnormality and is not considered isFavorable or isAdverse
 5. isIntermediateOrAdverse
   a. NPM1 negative and FLT3-ITD positive without an allelic ratio NAs occur in the absence of FLT3-ITD or NPM1 calls.
Samples where the specific diagnosis at inclusion indicated 'Acute promyelocytic leukaemia with t(15;17)(q22;q12)' were automatically set to 'Favorable'. Any overlaps of the categories were resolved based on manual expert review.

Ex Vivo Functional Drug Screens

Ex vivo functional drug screens were performed on freshly isolated mononuclear cells from AML samples. Briefly, 10,000 cells per well were arrayed into three, 384-well plates containing 122 small-molecule inhibitors. Drug plates were created using inhibitors purchased from LC Laboratories and Selleck Chemicals and master stocks were reconstituted in DMSO and stored at −80° C. Master plates were created by distributing a single agent per well in a seven-point concentration series, created from three-fold dilutions of the most concentrated stock resulting in a range pf 10 µM to 0.0137 µM for each drug (except dasatinib, ponatinib, sunitinib, and YM-155 which were plated at a concentration range of 1 µM to 0.00137 µM). DMSO control wells and positive control wells containing a drug combination of Flavopiridol, Staurosporine and Velcade were placed on each plate, with the final concentration of DMSO ≤0.1% in all wells. Daughter plates were created using a V&P Scientific 384-well pin tool head operated by the Caliper Sciclone ALH 3000 and equipped with 0.457 mm diameter, 30 nanoliter, slotted stainless steel pins (cat num: FP1NS30). Daughter and destination plates were sealed with pealable thermal seals using a PlateLoc thermal sealer. Destination plates were stored at −20° C. for no more than three months and thawed immediately before use. Primary mononuclear cells were plated across single-agent inhibitor panels within 24 h of collection. Cells were seeded into 384-well assay plates at 10,000 cells per well in RPMI 1640 media supplemented with FBS (10%), 1-glutamine, penicillin/streptomycin, and 3-mercaptoethanol (10-4 M). After 3 d of culture at 37° C. in 5% $CO_2$, MTS reagent (CellTiter96 AQueous One; Promega) was added, optical density was measured at 490 nm, and raw absorbance values were adjusted to a reference blank value and then used to determine cell viability (normalized to untreated control wells).

Ex vivo Functional Drug Screen Data Processing

A given sample was run on one or more panels and within each panel, the majority of drugs were run without within-panel replicates. Two steps were performed to harmonize these data prior to model fitting:
 1. A 'curve-free' AUC (integration based on fine linear interpolation between the 7 data points themselves) was calculated for those runs with within-panel replicates after applying a ceiling of 100 and a floor of 0 for the normalized viability. The maximum change in AUC amongst the replicates was noted and those runs with differences >100 were removed.
 2. Remaining within-plate replicates had their normalized viability averaged and subject to a ceiling of 100 and floor of 0. An additional set of 'curve-free' AUCs was computed for sample-inhibitor pairs run on multiple panels. The maximum change in AUC amongst the across-panel replicates was noted and those runs with differences >75 were removed.

At this point, the within and across plate replicates for the normalized viability were averaged together and a ceiling of 100 was applied. From the steps above, the floor was already at 0.

Based on the methodology used in our prior drug combination study[36], a probit regression was fit to all possible run groups using the model:

(normalized_viability/100)~1+log 10(concentration)

Where for all groups there were N=7 dose-response measurements.

The summary measures of curve fit were inspected and cutoffs were devised removing all runs with an AIC >12 and deviance >2. For inhibitors that were run using multiple concentration ranges, only the latest concentration range was kept. Finally, these data were compared to the AUC values from third order polynomial fits. Those runs that were discrepant in terms of sensitive/resistant calls were manually reviewed as subject to removal.

Ex Vivo Functional Drug Screen Analysis

For all drug analyses requiring a call of sensitivity or resistance (e.g. the gene expression signatures), sensitivity/resistance was determined by the lowest and highest 20% of the AUC values for each drug.

Correlations Between Drugs in Families

For each inhibitor in the study, available data on targets of the inhibitors were pulled from a variety of online resources and published studies, many of which were aggregated in the Cancer-Targetome[37,38]. Activity of each inhibitor for targets was then distilled into a 5-tier system to afford comparison across drugs with differing degrees of potency and/or for which differing assays were used to measure drug/target activity. Well-represented genes, gene families, and pathways were then filtered for drugs having activity in the top 3 tiers for one or more member of the gene family or pathway. These lists were then manually curated to arrive at a final list of high-confidence drug target families. For each inhibitor assigned to at least one drug target family, the Pearson's correlation was computed against all other drugs assigned to at least one drug target family for the AUC values of all available samples shared between the two drugs.

Correlations Between Drugs/Samples

Drugs were first filtered requiring greater than two hundred samples per drug. Additional samples were removed accordingly to allow correlations to be computed between all present samples using available AUC data and between all drugs.

Summary Drug Response Scores

For each patient sample, a binary encoding (1/0) was used for each drug based on same threshold as for the gene signatures (e.g., sensitivity/resistance was determined by the lowest and highest 20% of the AUC values for each drug). Individual scores were computed for resistance and sensitivity separately and represented as the proportion over all drugs screened for each patient sample.

Expression Analysis and Integration with Ex Vivo Functional Drug Screen

For all the below analyses the earliest sample was chosen for each patient.

Expression Heatmap

The top 2,000 most variable genes were extracted. The expression values were centered and scaled across patients and complete-linkage hierarchical clustering was performed using the ComplexHeatmap R package[39].

Sensitive/Resistant Differential Expression

For each drug, it was required that at least 3 sensitive and 3 resistant samples using the 20%/20% criteria outlined in the 'Drug Analysis' section. Patient samples were limited to those labeled as sensitive or resistant. Next, genes were limited based on their expression, where at least half the patients used for analysis had to have greater than one counts per million (an approach suggested in the limma users manual[40]. The normalized expression as in the 'RNA-Seq Processing' section data with the chosen samples and genes was used for differential expression analysis. As the data had not been batch corrected at this point, surrogate variable analysis (SVA)[41] was used to infer covariates for correcting out technical confounders. Next the linear model fitting for each gene was performed using the limma-trend approach[42] testing whether the average expression was different between resistant-sensitive correcting for the SVA covariates. Genes with Benjamini-Hochberg (BH)[43] FDR values of less than 0.05 were kept for the cluster analysis. The expression matrix was corrected with respect to the estimated surrogate variables for consistency with the differential expression procedure using fSVA[44] and Mclust[45] was used to determine optimal number of clusters and parameterization. The results were then visualized using a clusplot[46] which displays the clustering results with respect to the first two principal components of the gene expression for the kept genes.

Mutation Analysis and Integration with Ex Vivo Functional Drug Screen

For all the below analyses where groups of samples were compared, the earliest sample was chosen for each patient.

TCGA Comparison

The lifted over TCGA variants from the 'WES Variant Detection' section were annotated using the VEP from Ensembl build 83, filtered for protein-altering and splice site variants and our 'blacklist' was applied to ensure the variant sets were comparable.

Co-Occurrence/Mutual Exclusivity

Only mutations seen in at least 10 patients were kept. The DISCOVER[47] method was used to determine significant mutual exclusivity and co-occurrence. A plot of the co-occurrences was generated using corrplot[48] with the odds ratio of the pairwise co-occurrence used to color and scale the circle sizes.

Mutation/Drug Association

For each mutated gene in the exome sequencing samples and each recurrent fusion (counting FLT3-ITD as a distinct entity from other FLT3 mutants) we determined all available (at least 5 patients) pairwise and three-way co-occurrence sets. For each gene/set we performed a single-factor ANOVA testing whether there was an average change in AUC between samples possessing a given set of 1, 2 or 3 mutated genes and those without. FDR was computed using the BH over all the drugs.

For the Ibrutinib comparison, the presence and absence of the 3 genes/mutations: NPM1, FLT3_ITD and DNMT3A was collapsed into levels of a single factor. The corresponding single factor ANOVA was carried out with the 'triple negative' category set as the reference. Significance of the p-values of each coefficient were compared to the Bonferroni corrected 0.05 level.

For the JAK-family analysis, the AUC values were pooled for the four JAK inhibitors (CYT387, Tofacitinib (CP-690550), JAK Inhibitor I, Ruxolitinib (INCB018424)) for each gene mutation set (BCOR, BCOR:DNMT3A, BCOR:RUNX1, BCOR:SRSF2). The contrast of the difference between BCOR:RUNX1 samples and the average of the other three mutation groups was tested.

Integration of Both Mutation and RNA-Sequencing with Ex Vivo Functional Drug Screen Mutations (0/1 encoding) and the module eigengenes from the WGCNA analysis were used separately and combined together in regression models with coefficients selected using the lasso approach[49] as implemented in glmnet[50]. For each datatype and the combination, only drugs with at least 200 patients samples were tested. The 3 datasets were initially randomly separated into training (75%) and test (25%) sets. Similar to a previous approach[51], a bootstrap aggregation approach was used where the 1,000 bootstraps of the training dataset was generated and for each one, the lasso trained using 10 fold cross-validation. Predictions were formed for the test dataset over these bootstrap models and the predicted AUC was averaged. $R^2$ values were computed for these aggregated predictions relative to the test AUC values. As performance was seen to be dependent on the initial test/training split, we repeated the entire process 100 times, recording the mean and standard deviation of the $R^2$ value as well as the count non-zero coefficients.

Data Availability

All raw and processed sequencing data, along with relevant clinical annotations are being submitted to dbGaP and Genomic Data Commons. The raw data for clinical annotations, variant calls, gene expression counts, and drug sensitivity that underlie all figures in this manuscript are found in the Supplemental Tables. In addition, all data can be accessed and queried through our online, interactive user interface, Vizome, at www.vizome.orq.

Integration of Genetic and Cytogenetic Events with Patterns of Drug Sensitivity

The table below represents the relationship of genetic and cytogenetic events with patterns of drug sensitivity in the patient samples. All mutational and cytogenetic events where at least 5 patient samples with evaluable drug sensitivity data exhibited mutation of a gene were assessed for average difference in area under the curve between mutant and wild type samples. A statistical comparison of the mutant versus wild type drug sensitivity patterns (corrected for multiple comparisons) was also computed. The dataset was visualized on Volcano plots specific to each drug or mutant gene, where the average difference in area under the curve between mutant and wild type cases (measure of effect of the drug) was plotted on the horizontal axis and FDR-corrected q-value (statistical significance) was plotted on the vertical axis (for example, see FIG. 5). The dataset captured in this table are those found in the top left quadrant of the various volcano plots.

As used herein, a colon ":" between two listed mutations indicates separate mutations, such as BCOR:ASXL1 indicates separate BCOR and ASXL1 mutations present in the same AML experienced by a subject. Two identifiers connected by a hypen "-", underline "_" ~, or a period "." represents gene fusion, such as RUNX1-RUNXIT1 and CBFB-MYH11.

| MUTATION | DRUGS |
| --- | --- |
| ASXL1 | SNS-032 (BMS-387032) |
| BCOR | RAF265 (CHIR-265), Crizotinib (PF-2341066), or XAV-939 |
| BCOR:ASXL1 | XAV-939 |
| BCOR:DNMT3A | XAV-939 |
| BCOR:RUNX1 | JNJ-38877605 |
| BCOR:SRSF2 | XAV-939 |
| CBFB.MYH11 | Crenolanib, Trametinib (GSK1120212), Go6976, PLX-4720, Saracatinib, or Dasatinib |
| CBFB.MYH11:NRAS | Trametinib (GSK1120212) or YM-155 |
| CELSR2 | Tivozanib (AV-951) |
| DNMT3A | Lenvatinib, Ibrutinib (PCI-32765), Saracatinib (AZD0530), Cabozantinib, Sorafenib, or Entospletinib |
| DNMT3A:FLT3 | Crenolanib |
| DNMT3A:IDH2 | Entospletinib (GS-9973) |
| DNMT3A:NRAS | CI-1040 (PD184352) |
| FLT3 | Foretinib (XL880) |
| FLT3_ITD | Barasertib, vargetef, 17-AAG, NVP-TAE684, Tozasertib, ibrutinib, vandetanib, gefitinib, lanvatinib, pazopanib, or canertinib |
| FLT3_ITD (cont'd) | bosutinib, regorafenib (BAY 73-4506), roscovitine, crizotinib, pelitinib, tivozanib, INK-128, vx-745, vatalanib, mgcd-265, or cyt387 |
| FLT3_ITD (cont'd) | NF-kB activation inhibitor, Saracatinib, vemurafenib, imatinib, or axitinib |
| FLT3_ITD_IHD2 | Barasertib, Nvp-TAE684, tozasertib (VX-680), canertinib, masitinib, vandetanib, lapitinib, ruxolitinib, bosutinib, gefitinib, or vatalanib |
| FLT3_ITD_IHD2 (cont'd) | vargetef, axitinib, mgcd-265, 17-AAG, or ibrutinib |
| FLT3_ITD:ASXL1 | Barasertib, 17-AAG, vatalanib, or vx-745 |
| FLT3_ITD:DNMT3A | NVP-TAE684, vargetef, tozasertib (VX-680), pazopanib, barasertib, 17-AAG, erlotinib, axitinib, mgcd-265, bosutinib, or ibrutinib |
| FLT3_ITD:FLT3 | vargetef or nvp-TAE684 |
| FLT3_ITD:IDH1 | DBZ or Venetoclax |
| FLT3_ITD:RUNX1 | bosutinib, nvp-TAE684, 17-AAG (Tanespimycin), mgcd-265, motesanib, cediranib, GDC-0941, or imatinib |
| FLT3_ITD:SRSF2 | Gefitinib, crizotinib (PF-2341066), or Vandetanib |
| FLT3_ITD:TET2 | vandetanib, barasertib, pazopanib (GW786034), vargetef, canertinib, bosutinib, nvp-tae684, mgcd-265, or masitinb |
| FLT3_ITD:TET2:DNMT3A | Vargetef or Foretinib (XL880) |
| FLT3_ITD:WT1 | Barasertib (AZD1152-HQPA), 17-AAG, foretinib, mgcd-265, or vatalanib |
| IDH1 | YM-155 |
| IDH2 | Crizotinib (PF-2341066), GW-2580, Vargetef, Lenvatinib, NVP-TAE684, GSK-1838705A, PHA-665752, DBZ, Foretinib, Masitinib, or Entospletinib |
| IDH2 (cont'd) | Entospletinib, Tozasertib (VX-680), Ruxolitinib (INCB018424), or Barasertib |
| IDH2:FLT3 | NVP-TAE684 |
| MLLT3.KMT2A | GSK690693 or Vatalanib (PTK787) |
| Myc | Saracatinib |
| NPM1 | KW-2449, ibrutinib (PCI-32765), Vandetanib, Levatinib, Sorafenib, Regorafenib, Cabozantinib, DBZ, Entospletinib, SNS-032 (BMS-387032), or Foretinib |
| NPM1 (cont'd) | sunitinib, dovitinib, quizartinib, ponatinib, barasertib, erlotinib, crenolanib, 17-AAG, Gefitinib, NVP-TAE684, or Vagetef |
| NPM1 (cont'd) | DBZ, Gilteritinib, Palbociclib, Tivozanib, Lapatinib, Axitinib, Lenalidomide, Pelitinib, or vemurafenib |
| NPM1:CEBPA | KW-2449, SGX-523, or Crizotinib |
| NPM1:DNMT3A | Lenvatinib, Ibrutinib (PCI-32765), Saracatinib (AZD0530), Regorafenib, foretinib, Cabozantinib, Sorafenib, KW-2449, PRT062607, Entospletinib, or Crenolanib |
| NPM1:DNMT3A (cont'd) | Gefitinib, Dovitinib, 17-AAG, Axitinib, Gilteritinib, Quizartinib, Sunitinib, Ponatinib, or JNJ-7706621 |
| NPM1:DNMT3A:FLT3 | lenvantinib |
| NPM1:DNMT3A:NRAS | CI-1040 (PD184352) or Ibrutinib (PCI-32765) |
| NPM1:FLT3 | Foretinib or NVP-TAE684 |
| NPM1:FLT3_ITD | foretinib, ibrutinib (PCI-32765), barasertib, vargetef, 17-AAG, |

| MUTATION | DRUGS |
|---|---|
| NPM1:FLT3_ITD (cont'd) | nvp-tae684, vandetanib, regorafenib, lapatinib, bosutinib, or gefitinib<br>canertinib, crizotinib (PF-2341066), lenvatinib, pazopanib, pelitinib, vatalanib, ink-128, Tivozanib, MGCD-265, cyt387, or axitinib |
| NPM1:FLT3_ITD:DNMT3A | foretinib, regorafenib (BAY 73-4506), tozasertib (VX-680), vargetef, NVP-TAE684, gefitinib, 17-AAG, pazopanib, erlotinib, vandetanib, or tivozanib |
| NPM1:FLT3_ITD:DNMT3A (cont'd) | axitinib, saracatinib, bosutinib, or ibrutinib |
| NPM1:FLT3_ITD:FLT3 | |
| NPM1:FLT3_ITD:TET2 | Barasertib, vandetanib, erlotinib, vargetef, 17-AAG, or pazopanib |
| NPM1:IDH1 | Barasertib, JNJ-7706621, Dovitinib (CHIR-258), ym-155, erlotinib, roscovitine, or entospletinib |
| NPM1:IDH2 | DBZ, KW-2449, MLN120B, Vandetanib, NVP-TAE684, Vargetef, NF-kB activation inhib, GSK-1838705A, SGX-523, GW-2580, or ibrutinib |
| NPM1:IDH2 (cont'd) | Barasertib, ponatinib, SGX-523, Lapatinib, gefitinib, Gilteritinib, ruxolitinib, palbociclib, sorafenib, erlotinib, or vx-745 |
| NPM1:IDH2 (cont'd) | cabozantinib, entospetinib (GS-9973), quizartinib, lenvatinib, regorafenib, or vemurafenib |
| NPM1:NRAS | CI-1040 (PD184352) |
| NPM1:SRSF2 | KW-2449, vandetanib, DBZ, nvp-TAE684, Tozasertib, lenalidomide, GSK-183705A, MLN120B, Masitinb, Foretinib, or Sunitinib |
| NPM1:SRSF2 (cont'd) | Vargetef, Barasertib, ponatinib, SGX-523, Lapatinib, ibrutinib, gefitinib, Gilteritinib, ruxolitinib, palbociclib, or sorafenib |
| NPM1:SRSF2 (cont'd) | erlotinib, vx-745, gw-2580, cabozantinib, entospetinib, quizartinib, nf-kB activation inhib, lenvatinib, regorafenib, or vemurafenib |
| NPM1:SRSF2:IDH2 | ibrutinib (PCI-32765), KW-2449, SGX-523, AZD1480, NVP-TAE684, KI20227, or DBZ |
| NPM1:TET2 | Ibrutinib (PCI-32765), Sorafenib, or Sunitinib |
| NPM1:TET2: DNMT3A | Regorafenib (BAY 73-4506), Cabozantinib, Lenvatinib, Vargetef, orEntospetinib |
| NRAS | Selumetinib (AZD6244), CI-1040 (PD184352), Trametinib (GSK1120212), or Flavopiridol |
| PDS5B | BMS-345541 |
| PML.RARA | Venetoclax, ABT-737, or YM-155 |
| RUNX1 | Cediranib (AZD2171) or BEZ2345 |
| RUNX1:DNMT3A | MGCD-265 |
| RUNX1:RUNX1T1 | Pazopanib (GW786034) |
| SMC1A | GDC-0879, Vatalanib (PTK787), GSK-1838705A, Bay 11-7085, Masitinib, lapatinib, canertinib, foretinib, or crizotinib |
| SRSF2:IDH2 | Crizotinib (PF-2341066), or GSK-1838705A |
| TRIO | Palbociclib |
| U2AF1 | Cediranib (AZD2171) |
| WT1 | RAF265 (CHIR-265), Vismodegib (GDC-0449), or MK-2206 |
| ZRSR2 | KU-55933, Tofacitinib (CP-690550), or Roscovitine |

SUPPLEMENTAL METHODS REFERENCES

1 Li, H. & Durbin, R. Fast and accurate short read alignment with Burrows-Wheeler transform. *Bioinformatics* 25, 1754-1760, doi: 10.1093/bioinformatics/btp324 (2009).

2 McKenna, A. et al. The Genome Analysis Toolkit: a MapReduce framework for analyzing next-generation DNA sequencing data. *Genome Res* 20, 1297-1303, doi: gr.107524.110 [pii]10.1101/gr.107524.110 (2010).

3 Huntley, M. A. et al. ReportingTools: an automated result processing and presentation toolkit for high-throughput genomic analyses. *Bioinformatics* 29, 3220-3221, doi: 10.1093/bioinformatics/btt551 (2013).

4 Buffalo, V. qrqc: Quick Read Quality Control. R package version 1.22.0, http://github.com/vsbuffalo/qrqc. (2012).

5 Cibulskis, K. et al. Sensitive detection of somatic point mutations in impure and heterogeneous cancer samples. *Nat Biotechnol* 31, 213-219, doi:10.1038/nbt.2514 (2013).

6 Koboldt, D. C. et al. VarScan 2: somatic mutation and copy number alteration discovery in cancer by exome sequencing. *Genome Res* 22, 568-576, doi:10.1101/gr.129684.111 (2012).

7 McLaren, W. et al. Deriving the consequences of genomic variants with the Ensembl API and SNP Effect Predictor. *Bioinformatics* 26, 2069-2070, doi:10.1093/bioinformatics/btq330 (2010).

8 Kandoth, C. https://github.com/ckandoth/vcf2maf.

9 varscan: Variant calling and somatic mutation/CNV detection for next-generation sequencing data (2018).

10 TCGA. Genomic and epigenomic landscapes of adult de novo acute myeloid leukemia. *N Engl J Med* 368, 2059-2074, doi:10.1056/NEJMoa1301689 (2013).

11 vcf2maf: Convert a VCF into a MAF, where each variant is annotated to only one of all possible gene isoforms (Memorial Sloan Kettering, 2018).

12 Zhao, H. et al. CrossMap: a versatile tool for coordinate conversion between genome assemblies. *Bioinformatics* 30, 1006-1007, doi:10.1093/bioinformatics/btt730 (2014).

13 Jaiswal, S. et al. Age-related clonal hematopoiesis associated with adverse outcomes. *N Engl J Med* 371, 2488-2498, doi:10.1056/NEJMoa1408617 (2014).

14 Lek, M. et al. Analysis of protein-coding genetic variation in 60,706 humans. *Nature* 536, 285-291, doi:10.1038/nature19057 (2016).

15 Ye, K., Schulz, M. H., Long, Q., Apweiler, R. & Ning, Z. Pindel: a pattern growth approach to detect break points of large deletions and medium sized insertions from paired-end short reads. *Bioinformatics* 25, 2865-2871, doi:10.1093/bioinformatics/btp394 (2009).

16 Costello, M. et al. Discovery and characterization of artifactual mutations in deep coverage targeted capture sequencing data due to oxidative DNA damage during sample preparation. *Nucleic Acids Research* 41, e67, doi:10.1093/nar/gks1443 (2013).

17 Kottaridis, P. D. et al. The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials. *Blood* 98, 1752-1759 (2001).

18 Dohner, K. et al. Mutant nucleophosmin (NPM1) predicts favorable prognosis in younger adults with acute myeloid leukemia and normal cytogenetics: interaction with other gene mutations. *Blood* 106, 3740-3746, doi:10.1182/blood-2005-05-2164 (2005).

19 Falini, B., Nicoletti, I., Martelli, M. F. & Mecucci, C. Acute myeloid leukemia carrying cytoplasmic/mutated nucleophosmin (NPMc+ AML): biologic and clinical features. *Blood* 109, 874-885, doi:10.1182/blood-2006-07-012252 (2007).

20 Huang, Q. et al. A rapid, one step assay for simultaneous detection of FLT3/ITD and NPM1 mutations in AML with normal cytogenetics. *Br J Haematol* 142, 489-492, doi:10.1111/j.1365-2141.2008.07205.x (2008).

21 Wouters, B. J. et al. Double CEBPA mutations, but not single CEBPA mutations, define a subgroup of acute myeloid leukemia with a distinctive gene expression profile that is uniquely associated with a favorable outcome. *Blood* 113, 3088-3091, doi:10.1182/blood-2008-09-179895 (2009).

22 Liao, Y., Smyth, G. K. & Shi, W. The Subread aligner: fast, accurate and scalable read mapping by seed-and-vote. *Nucleic Acids Res* 41, e108, doi:10.1093/nar/gkt214 (2013).

23 Liao, Y., Smyth, G. K. & Shi, W. featureCounts: an efficient general purpose program for assigning sequence reads to genomic features. *Bioinformatics* 30, 923-930, doi:10.1093/bioinformatics/btt656 (2014).

24 Langfelder, P. & Horvath, S. WGCNA: an R package for weighted correlation network analysis. *BMC bioinformatics* 9, 559, doi:10.1186/1471-2105-9-559 (2008).

25 Hansen, K. D., Irizarry, R. A. & Wu, Z. Removing technical variability in RNA-seq data using conditional quantile normalization. *Biostatistics* 13, 204-216, doi:10.1093/biostatistics/kxr054 (2012).

26 Kim, D. & Salzberg, S. L. TopHat-Fusion: an algorithm for discovery of novel fusion transcripts. *Genome biology* 12, R72, doi:10.1186/gb-2011-12-8-r72 (2011).

27 Langfelder, P. & Horvath, S. Fast *R* Functions for Robust Correlations and Hierarchical Clustering. *Journal of Statistical Software* 46, doi:10.18637/jss.v046.i11 (2012).

28 Langfelder, P., Luo, R., Oldham, M. C. & Horvath, S. Is My Network Module Preserved and Reproducible? *PLoS computational biology* 7, e1001057, doi:10.1371/journal.pcbi.1001057 (2011).

29 Parsana, P. et al. Addressing confounding artifacts in reconstruction of gene co-expression networks. *bioRxiv*, 202903, doi:10.1101/202903 (2017).

30 Zheng, X. et al. A high-performance computing toolset for relatedness and principal component analysis of SNP data. *Bioinformatics* 28, 3326-3328, doi:10.1093/bioinformatics/bts606 (2012).

31 International HapMap, C. The International HapMap Project. *Nature* 426, 789-796, doi:10.1038/nature02168 (2003).

32 Zheng, X. & Weir, B. S. Eigenanalysis of SNP data with an identity by descent interpretation. *Theoretical Population Biology* 107, 65-76, doi:10.1016/j.tpb.2015.09.004 (2016).

33 Robinson, M. D. & Oshlack, A. A scaling normalization method for differential expression analysis of RNA-seq data. *Genome biology* 11, R25, doi:10.1186/gb-2010-11-3-r25 (2010).

34 Dohner, H. et al. Diagnosis and management of AML in adults: 2017 ELN recommendations from an international expert panel. *Blood* 129, 424-447, doi:10.1182/blood-2016-08-733196 (2017).

35 Slovak, M. L., Theisen, A. & Shaffer, L. G. in *The Principles of Clinical Cytogenetics* (eds Steven L. Gersen & Martha B. Keagle) 23-49 (Springer New York, 2013).

36 Kurtz, S. E. et al. Molecularly targeted drug combinations demonstrate selective effectiveness for myeloid- and lymphoid-derived hematologic malignancies. *Proc Natl Acad Sci USA* 114, E7554-E7563, doi:10.1073/pnas.1703094114 (2017).

37 Davis, M. I. et al. Comprehensive analysis of kinase inhibitor selectivity. *Nat Biotechnol* 29, 1046-1051, doi:nbt.1990 [pii]10.1038/nbt.1990 (2011).

38 Blucher, A. S., Choonoo, G., Kulesz-Martin, M., Wu, G. & McWeeney, S. K. Evidence-Based Precision Oncology with the Cancer Targetome. *Trends in pharmacological sciences* 38, 1085-1099, doi:10.1016/j.tips.2017.08.006 (2017).

39 Gu, Z., Eils, R. & Schlesner, M. Complex heatmaps reveal patterns and correlations in multidimensional genomic data. *Bioinformatics* 32, 2847-2849, doi:10.1093/bioinformatics/btw313 (2016).

40 Ritchie, M. E. et al. limma powers differential expression analyses for RNA-sequencing and microarray studies. *Nucleic Acids Research* 43, e47-e47, doi:10.1093/nar/gkv007 (2015).

41 Leek, J. T. & Storey, J. D. Capturing Heterogeneity in Gene Expression Studies by Surrogate Variable Analysis. *PLOS Genetics* 3, e161, doi:10.1371/journal.pgen.0030161(2007).

42 Law, C. W., Chen, Y., Shi, W. & Smyth, G. K. voom: precision weights unlock linear model analysis tools for RNA-seq read counts. *Genome biology* 15, R29, doi:10.1186/gb-2014-15-2-r29 (2014).

43 Benjamini, Y. & Hochberg, Y. Controlling the false discovery rate: A practical and powerful approach to multiple testing. *Journal of the Royal Statistical Society, Series B (Methodological)* 57, 289-300 (1995).

44 Parker, H. S., Bravo, H. C. & Leek, J. T. Removing batch effects for prediction problems with frozen surrogate variable analysis. *PeerJ* 2, e561, doi:10.7717/peerj.561 (2014).

45 Fraley, C. & Raftery, A. E. Enhanced Model-Based Clustering, Density Estimation, and Discriminant Analysis Software: MCLUST. *Journal of Classification* 20, 263-286, doi:10.1007/s00357-003-0015-3 (2003).
46 Pison, G., Struyf, A. & Rousseeuw, P. J. Displaying a clustering with CLUSPLOT. *Computational Statistics & Data Analysis* 30, 381-392, doi:10.1016/S0167-9473(98)00102-9 (1999).
47 Canisius, S., Martens, J. W. M. & Wessels, L. F. A. A novel independence test for somatic alterations in cancer shows that biology drives mutual exclusivity but chance explains most co-occurrence. *Genome biology* 17, 261, doi:10.1186/s13059-016-1114-x (2016).
48 Package corrplot is for visualizing a correlation matrix (2018).
49 Tibshirani, R. Regression Shrinkage and Selection via the Lasso. *Journal of the Royal Statistical Society. Series B (Methodological)* 58, 267-288 (1996).
50 Friedman, J., Hastie, T. & Tibshirani, R. Regularization Paths for Generalized Linear Models via Coordinate Descent. *Journal of Statistical Software* 33, doi:10.18637/jss.v033.i01 (2010).
51 Iorio, F. et al. A Landscape of Pharmacogenomic Interactions in Cancer. *Cell* 166, 740-754, doi:10.1016/j.cell.2016.06.017 (2016).

What is claimed:

1. A method of treating Acute Myeloid Leukemia in a human, wherein the Acute Myeloid Leukemia is characterized by a mutation at least in the NPM1 gene, the method comprising administering to the human in need thereof a therapeutically effective amount of ibrutinib, or a pharmaceutically acceptable salt thereof.

2. The method of claim 1, wherein the Acute Myeloid Leukemia is further characterized by a mutation in the DNMT3A gene.

3. The method of claim 1, wherein the Acute Myeloid Leukemia is further characterized by a mutation in the FLT3 gene.

4. The method of claim 1, wherein the Acute Myeloid Leukemia is further characterized by mutations in the DNMT3A and FLT3 genes.

5. The method of claim 1, wherein ibrutinib is administered to the human in need thereof at a dose of from about 50 mg to about 1200 mg once or twice daily.

* * * * *